United States Patent
Gray et al.

(10) Patent No.: US 12,365,664 B2
(45) Date of Patent: Jul. 22, 2025

(54) SMALL MOLECULE INHIBITORS OF SRC TYROSINE KINASE

(71) Applicants: Dana-Farber Cancer Institute, Inc., Boston, MA (US); Board of Regents of the University of Texas System, Austin, TX (US)

(72) Inventors: Nathanael S. Gray, Boston, MA (US); Guangyan Du, Boston, MA (US); Tinghu Zhang, Brookline, MA (US); Nathaniel Henning, Brookline, MA (US); Suman Rao, Boston, MA (US); Kenneth Westover, Austin, TX (US); Deepak Gurbani, Austin, TX (US)

(73) Assignees: Dana-Farber Cancer Institute, Inc., Boston, MA (US); Board of Regents of the University of Texas System, Austin, TX (US)

( * ) Notice: Subject to any disclaimer, the term of this patent is extended or adjusted under 35 U.S.C. 154(b) by 809 days.

(21) Appl. No.: 17/620,473

(22) PCT Filed: Jun. 18, 2020

(86) PCT No.: PCT/US2020/038325
§ 371 (c)(1),
(2) Date: Dec. 17, 2021

(87) PCT Pub. No.: WO2020/257385
PCT Pub. Date: Dec. 24, 2020

(65) Prior Publication Data
US 2022/0267294 A1 Aug. 25, 2022

Related U.S. Application Data

(60) Provisional application No. 62/864,216, filed on Jun. 20, 2019.

(51) Int. Cl.
*C07D 401/04* (2006.01)
*C07D 239/48* (2006.01)
*C07D 239/50* (2006.01)
*C07D 405/04* (2006.01)
*C07D 409/04* (2006.01)
*C07D 491/048* (2006.01)
*C07D 495/04* (2006.01)

(52) U.S. Cl.
CPC ......... *C07D 401/04* (2013.01); *C07D 239/48* (2013.01); *C07D 239/50* (2013.01); *C07D 405/04* (2013.01); *C07D 409/04* (2013.01); *C07D 491/048* (2013.01); *C07D 495/04* (2013.01)

(58) Field of Classification Search
CPC ... C07D 401/04; C07D 405/04; C07D 409/04
See application file for complete search history.

(56) References Cited

U.S. PATENT DOCUMENTS

2014/0228322 A1  8/2014  Haq et al.
2022/0267294 A1  8/2022  Gray et al.

FOREIGN PATENT DOCUMENTS

| CN | 106243044 A | 12/2016 |
|---|---|---|
| CN | 109836428 A | 6/2019 |
| WO | WO-2010/129053 A2 | 11/2010 |
| WO | WO-2011/162515 A2 | 12/2011 |
| WO | WO-2015/117547 A1 | 8/2015 |
| WO | WO-2015/164614 A1 | 10/2015 |
| WO | WO-2016/130920 A2 | 8/2016 |
| WO | WO-2018/230934 A1 | 12/2018 |
| WO | WO-2020/257385 A1 | 12/2020 |

OTHER PUBLICATIONS

Lala, et al. Cancer and Metastasis Reviews (1998), 17(1), 91-106.*
Golub, et al. Science 286, 531 (1999).*
Cancer [online], [retrieved on Aug. 11, 2023]. Retrieved from the internet, URL https://medlineplus.gov/cancer.html#>.*
No new references.*
International Search Report and Written Opinion for International Application No. PCT/US 20/38325 mailed Oct. 5, 2020.
Invitation to Pay Additional Fees for International Application No. PCT/US2020/038325 dated Sep. 8, 2020.
PubChem CID 134130572 <https://pubchem.ncbi.nlm.nih.gov/compound/134130572> Create Date: Jun. 6, 2018.
Rao et al., "A multitargeted probe-based strategy to identify signaling vulnerabilities in cancers," J Biol Chem, 294(1):8664-8673 (2019).
Tan et al., "Structure-guided development of covalent TAK1 inhibitors," Bioorganic and Medicinal Chemistry, 25(3): 838-846 (2017).
Tan et al., "Studies of TAK1-centered polypharmacology with novel covalent TAK1 inhibitors," Bioorganic Medicinal Chemistry, (25)4: 1320-1328 (2017).
Extended European Search Report for EP Application No. 208265694 dated Jul. 5, 2023.

* cited by examiner

*Primary Examiner* — Shawquia Jackson
(74) *Attorney, Agent, or Firm* — Foley Hoag LLP; Deann F. Smith; Lucas P. J. Watkins D.

(57) ABSTRACT

Disclosed herein are compounds of Formula (I) and pharmaceutically acceptable salts thereof. Also disclosed herein are methods of using the compounds of Formula (I) in the treatment of certain diseases (e.g., cancer).

24 Claims, 5 Drawing Sheets

SMALL MOLECULE INHIBITORS OF SRC TYROSINE KINASE

RELATED APPLICATIONS

This application is the U.S. National Stage of PCT/US2020/038325, filed Jun. 18, 2020, which claims the benefit of U.S. Provisional Patent Application No. 62/864,216, filed on Jun. 20, 2019; the contents of each of these applications are hereby incorporated by reference in their entirety.

BACKGROUND

Kinases play a vital role in cell physiology, for example proto-oncogene tyrosine-protein kinase sarcoma (c-SRC) is involved in regulating cell division, motility, adhesion, angiogenesis, and survival. SRC was the first proto-oncogene discovered and is frequently overexpressed in certain cancerous tumors. The extent of c-SRC overexpression typically correlates with the metastatic potential of the malignant tumor, and inhibiting c-SRC has been shown to decrease breast cancer metastases in mice. Elevated c-SRC activity has recently been identified as a main cause of resistance to Herceptin, a first-line treatment for Her2-positive breast cancer. Efforts to better understand c-SRC in the context of oncogenic growth, metastasis, and/or drug resistance have been complicated by a lack of selective c-SRC inhibitors. Thus, there exists a need for new compounds that selectively inhibit kinases such as c-SRC.

SUMMARY OF THE INVENTION

In one aspect, the present disclosure provides compounds of Formula (I):

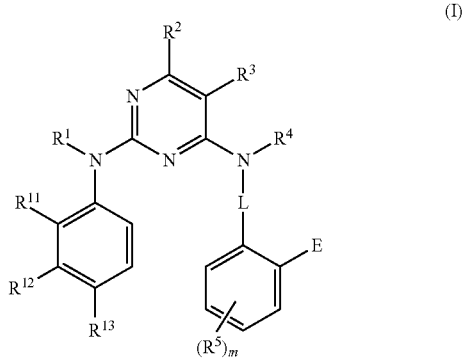

(I)

or a pharmaceutically acceptable salt thereof, wherein:
E is an electrophile;
L is a bond or alkylenyl;
each $R^1$ is independently selected from hydrogen and alkyl;
$R^2$ is selected from hydrogen and amino;
$R^3$ is selected from alkyl, —C(=O)$NR^1$-alkyl, —C(=O)$NR^1$-aryl, alkoxy, aryl, heteroaryl, cycloalkyl, halogen, and aralkyloxy; or $R^2$ and $R^3$, taken together with the carbon atoms to which they are attached, combine to form a heteroaryl;
$R^4$ is selected from hydrogen and alkyl;
each $R^5$ is independently selected from alkyl and halogen;
m is 0 or 1;
two of $R^{11}$, $R^{12}$, and $R^{13}$ are independently hydrogen or alkyl;
one of $R^{11}$, $R^{12}$, and $R^{13}$ is selected from

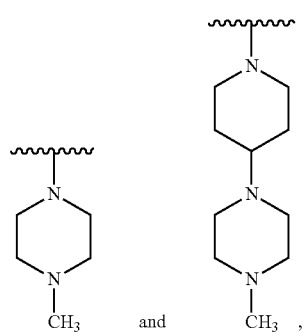

provided that if $R^1$ is hydrogen, $R^2$ is hydrogen, $R^3$ is chloro, $R^4$ is hydrogen, m is 0, E is

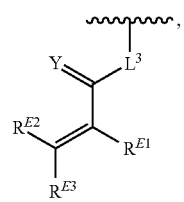

L is a bond, Y is O, $L^3$ is —$NR^{L3a}$—, $R^{L3a}$, $R^{E1}$, $R^{E2}$, and $R^{E3}$ are hydrogen,
$R^{11}$ is hydrogen, and $R^{12}$ is hydrogen, then $R^{13}$ is not

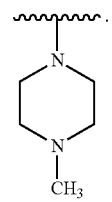 [SMILES: *N1CCN(C)CC1]

In certain aspects, the present disclosure provides methods using the compounds disclosed herein for the treatment of certain diseases (e.g., cancer).

DETAILED DESCRIPTION OF THE INVENTION

Figure 1:
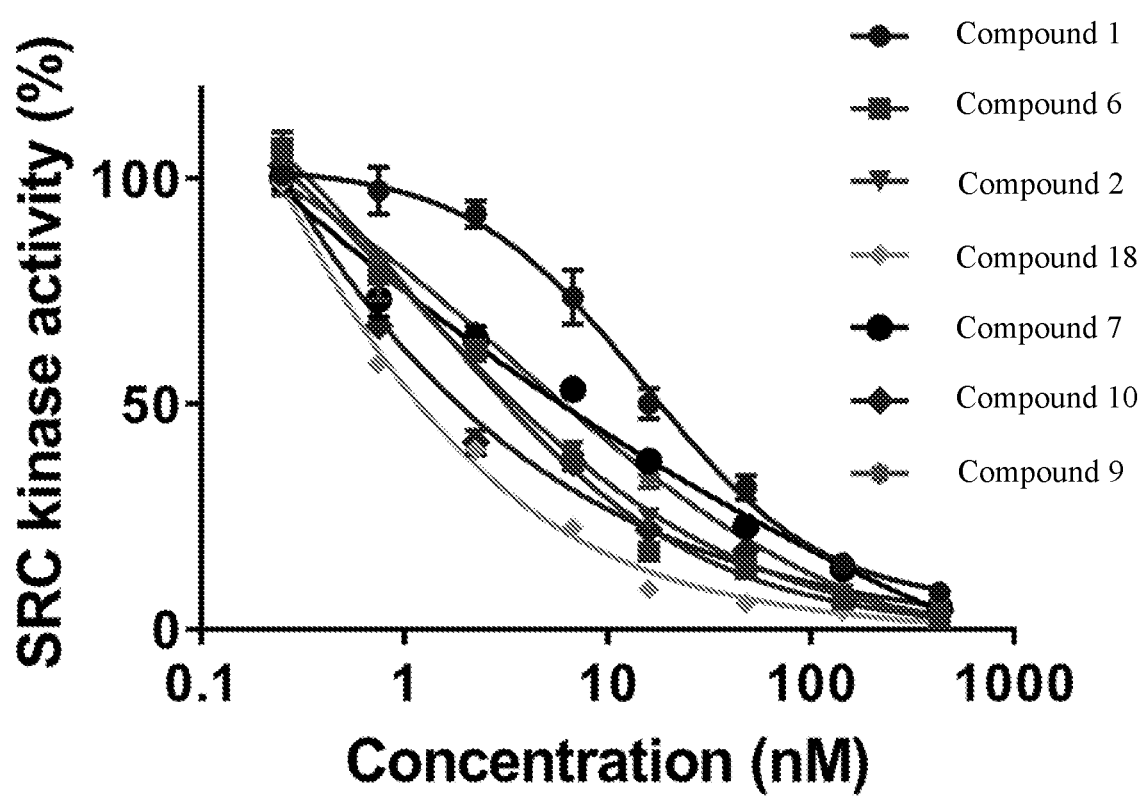
FIG. 1. shows dose response curves for exemplary compounds of the disclosure against SRC in a mobility shift assay.
Figure 2:
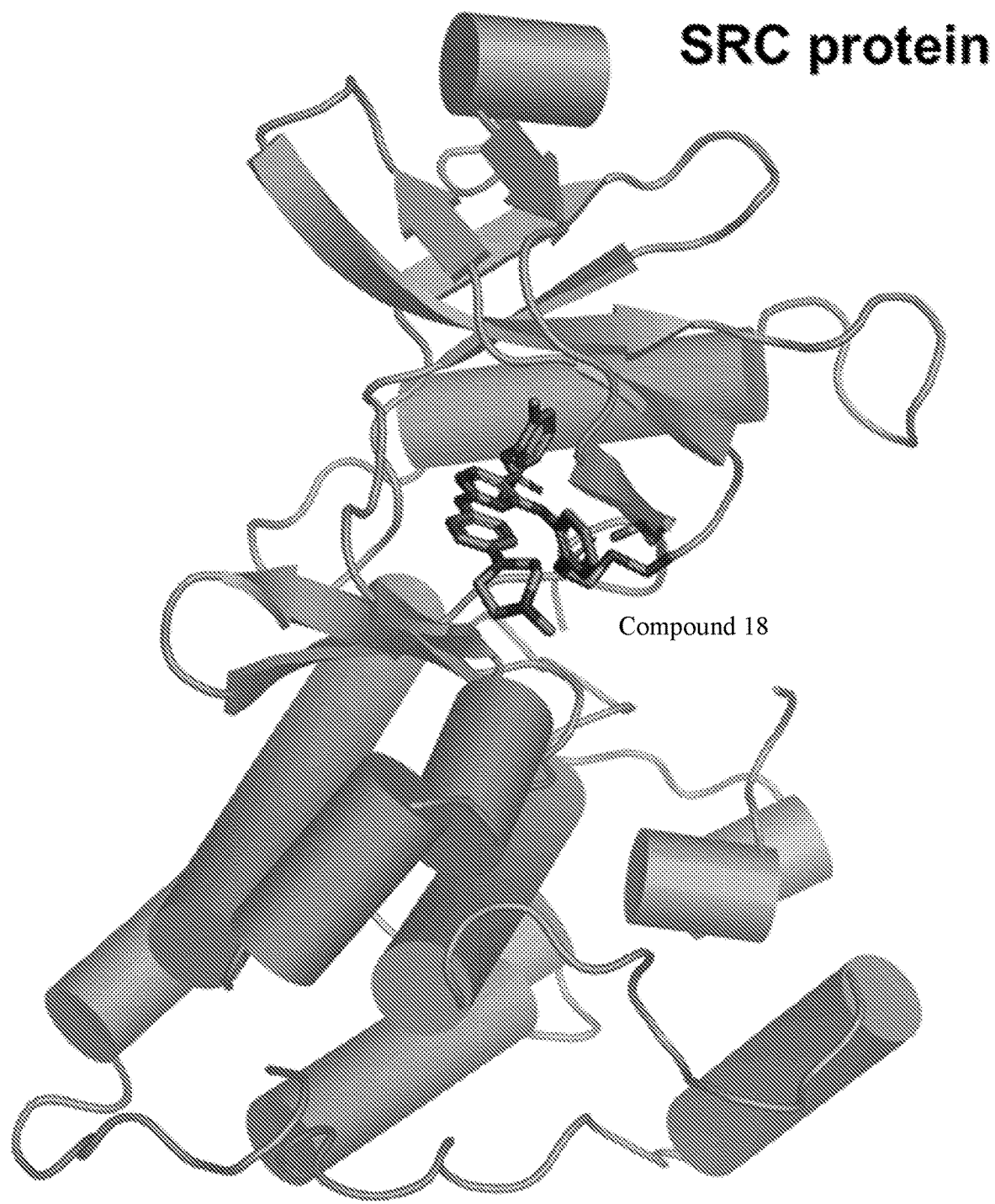
FIG. 2. depicts the crystal structure of compound 18 against SRC protein.

The physiological Src proto-oncogene is a protein-tyrosine kinase that plays key roles in cell growth, division, migration, and survival signaling pathways. From the N- to C-terminus, Src contains a unique domain, an SH3 domain, an SH2 domain, a protein-tyrosine kinase domain, and a regulatory tail. The chief phosphorylation sites of human Src include an activating pTyr419 that results from phosphorylation in the kinase domain by an adjacent Src molecule and an inhibitory pTyr530 in the regulatory tail that results from phosphorylation by C-terminal Src kinase (Csk) or Chk (Csk homologous kinase). In a variety of human cancers including melanoma, breast, and colorectal cancers, SRC family kinases (SFKs) are activated by various cues such as growth factors and cell-cell contact. SFKs are linked to malignant progression of human cancers, and in particular, their activity is frequently associated with metastatic potential. As such they serve as attractive therapeutic targets.

While reversible small molecule inhibitors of protein kinases have been extensively investigated, irreversible kinase inhibitors remain underexplored. Compared to their reversible counterparts, irreversible kinase inhibitors offer significant advantages, including increased potency and selectivity, longer residence times, the ability to inhibit kinases with existing resistance mutations, and non ATP-competitive modes of action. Despite these advantages, irreversible kinase inhibitors have only been developed for a handful of kinases. Disclosed herein are irreversible inhibitors of certain kinases, such as SRC kinase.

In one aspect, the present disclosure provides compounds of Formula (I):

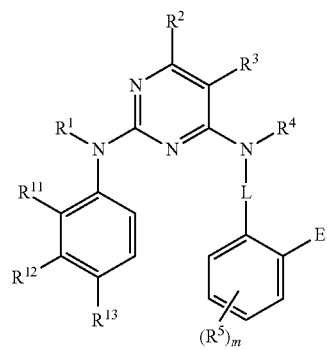

(I)

or a pharmaceutically acceptable salt thereof, wherein:

E is an electrophile;

L is a bond or alkylenyl;

each $R^1$ is independently selected from hydrogen and alkyl;

$R^2$ is selected from hydrogen and amino;

$R^3$ is selected from alkyl, —C(=O)NR$^1$-alkyl, —C(=O)NR$^1$-aryl, alkoxy, aryl, heteroaryl, cycloalkyl, halogen, and aralkyloxy; or $R^2$ and $R^3$, taken together with the carbon atoms to which they are attached, combine to form a heteroaryl;

$R^4$ is selected from hydrogen and alkyl;

each $R^5$ is independently selected from alkyl and halogen;

m is 0 or 1;

two of $R^{11}$, $R^{12}$, and $R^{13}$ are independently hydrogen or alkyl;

one of $R^{11}$, $R^{12}$, and $R^{13}$ is selected from

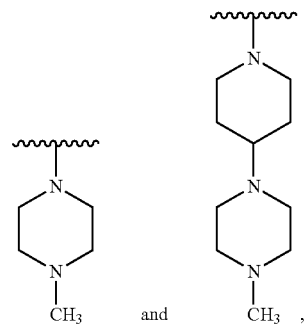

and provided that if $R^1$ is hydrogen, $R^2$ is hydrogen, $R^3$ is chloro, $R^4$ is hydrogen, m is 0, E is

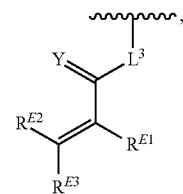

L is a bond, Y is O, $L^3$ is —NR$^{L3a}$—, $R^{L3a}$, $R^{E1}$, $R^{E2}$, and $R^{E3}$ are hydrogen, $R^{11}$ is hydrogen, and $R^{12}$ is hydrogen, then $R^{13}$ is not

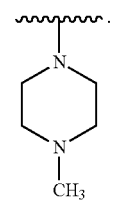 [SMILES: *N1CCN(C)CC1]

In certain embodiments, the electrophile is selected from structures (i-1) through (i-15).

-continued
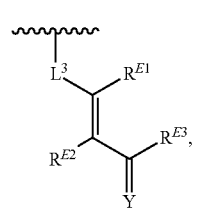 (i-16)
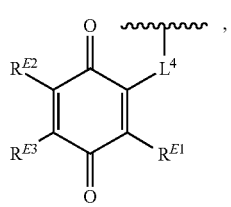 (i-17)
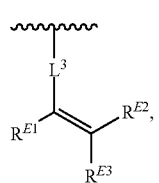 (i-18)
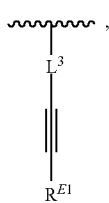 (i-19)
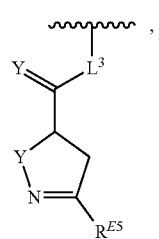 (i-20)
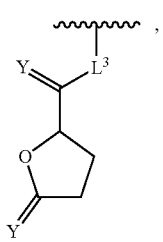 (i-21)
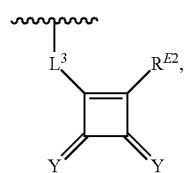 (i-22)
-continued
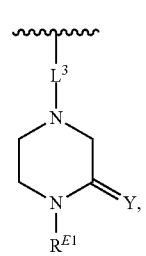 (i-23)
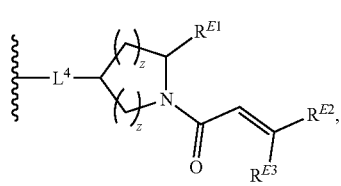 (i-24)
(i-25)
(i-26)
(i-27)
(i-28)
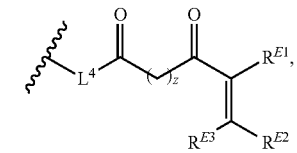 (i-29)
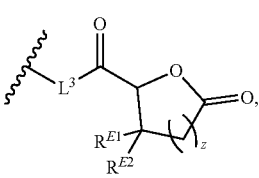 (i-30)

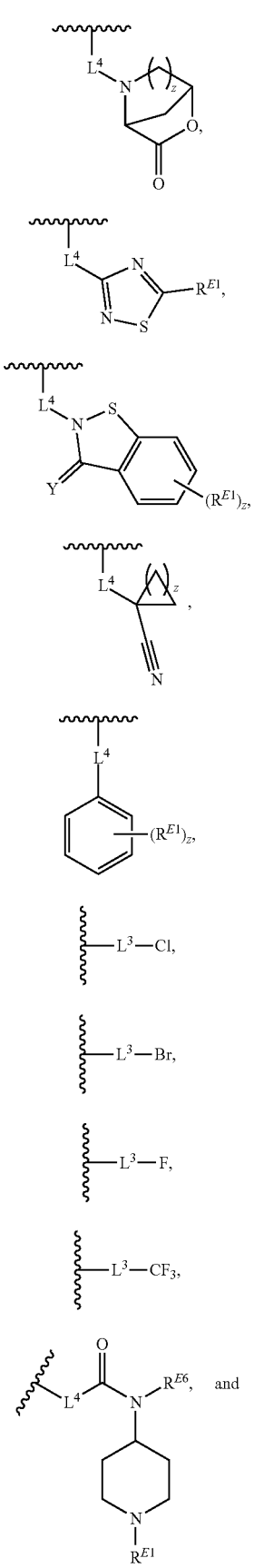

-continued (i-41)

wherein,

§ indicates the position of attachment to the compound of Formula (I);

$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

$L^4$ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group or alkyl;

R$^{E5}$ is halogen;

R$^{E6}$ is hydrogen, substituted or unsubstituted $C_{1-6}$ alkyl, or a nitrogen protecting group; each instance of Y is independently O, S, or NR$^{E7}$, wherein R$^{E7}$ is hydrogen, substituted or unsubstituted $C_{1-6}$ alkyl, or a nitrogen protecting group;

a is 1 or 2;

each instance of z is independently 0, 1, 2, 3, 4, 5, or 6, as valency permits; and each instance of $R^8$, if present, is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{D1}$, —$N(R^{D1a})_2$, and —$SR^{D1}$, wherein each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of $R^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of $R^{D1a}$ are taken together with their intervening atoms to form a substituted or unsubstituted heterocyclic or substituted or unsubstituted heteroaryl ring; or two $R^8$ groups are joined to form an optionally substituted carbocyclyl, optionally substituted heterocyclyl, optionally substituted aryl, or optionally substituted heteroaryl ring.

In certain preferred embodiments, the electrophile is of formula:

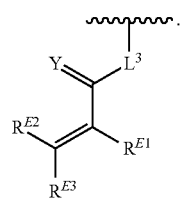

(i-1)

In certain embodiments, $R^{E1}$, $R^{E2}$, and $R^{E3}$ are each hydrogen. In other embodiments, $R^{E1}$ and $R^{E2}$ are each hydrogen; and $R^{E3}$ is aminoalkyl (e.g., dimethylamino alkyl). In certain embodiments $R^{E3}$ is dimethylaminoethyl. In certain embodiments, Y is O. In certain embodiments, $L^3$ is —$NR^{L3a}$—. In certain embodiments, $R^{L3a}$ is hydrogen.

In other preferred embodiments, the electrophile is of formula:

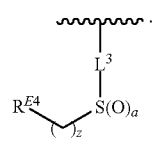

(i-10)

In certain embodiments, a is 2. In certain embodiments, $L^3$ is a bond. In certain embodiments, z is 0. In certain embodiments, $R^{E4}$ is alkyl (e.g., isopropyl).

In yet other embodiments, wherein the electrophile is of formula:

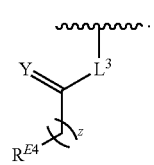

(i-9)

In certain embodiments, z is 1. In certain embodiments, $R^{E4}$ is alkyl (e.g., methyl). In other embodiments, $R^{E4}$ is halo (e.g., chloro). In certain embodiments, $L^3$ is a bond.

In yet other embodiments, wherein the electrophile is of formula:

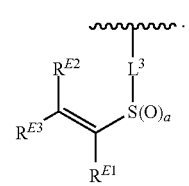

(i-2)

In certain embodiments, $L^3$ is a bond. In certain embodiments, a is 2. In certain embodiments, $R^{E1}$, $R^{E2}$, and $R^{E3}$ are each hydrogen.

In certain embodiments, L is alkylenyl (e.g., —$CH_2$—).

In certain embodiments, wherein the compound is represented by Formula (Ia) or (Ib):

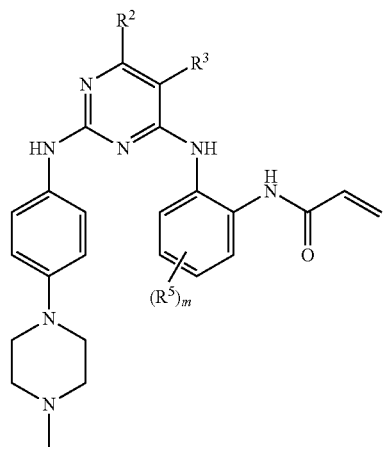

(Ia)

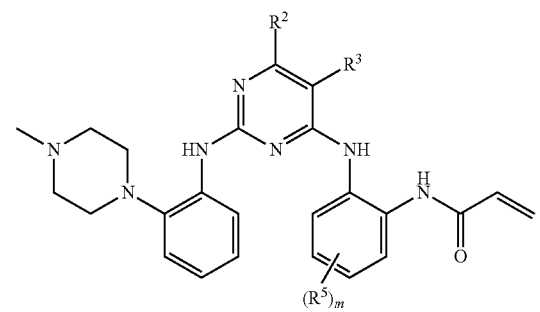

(Ib)

or a pharmaceutically acceptable salt thereof.

In other embodiments, the compound is represented by Formula (Ic) or (Id):

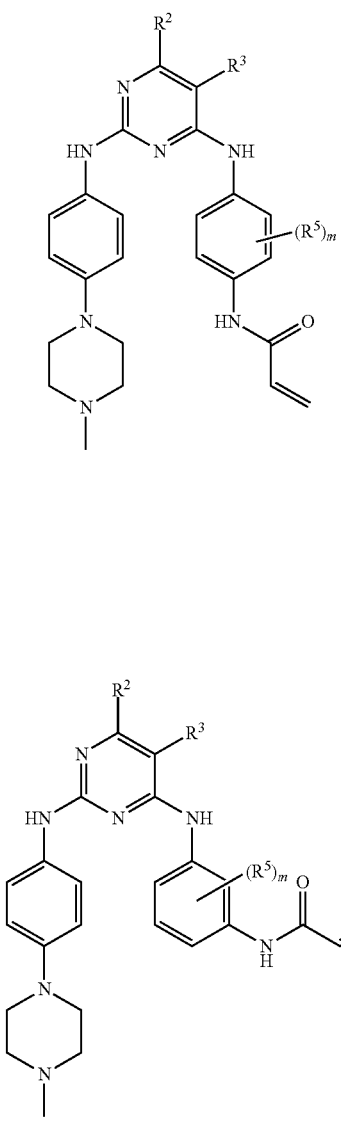

(Ic)

(Id)

or a pharmaceutically acceptable salt thereof.

In certain embodiments, $R^2$ is hydrogen. In certain embodiments, $R^2$ is amino.

In certain embodiments, $R^3$ is halo (e.g., chloro, iodo, bromo), alkyl (e.g., methyl, ethyl), cycloalkyl (e.g., cyclopropyl), aryl (e.g., phenyl), aryloxy (e.g., phenoxy), heteroaryl (e.g., thiophenyl, pyridyl, furanyl), or aralkyloxy (e.g., benzyloxy). In certain embodiments, the alkyl, cycloalkyl, aryl, heteroaryl, or aralkyloxy of $R^3$ is further substituted with alkyl, carboxyl, hydroxyl, hydroxyalkyl, alkoxy, halogen, nitro, acyl, acyloxy, amino, aminoalkyl, or cyano. In certain embodiments the alkyl, cycloalkyl, aryl, heteroaryl, or aralkyloxy of $R^3$ is substituted with alkyl (e.g., methyl), acyl (e.g., acetyl), aryloxy (e.g., phenyloxy), or halo (e.g., chloro).

In other embodiments, $R^2$ and $R^3$ combine to form a heteroaryl (e.g., furanyl or thiophenyl).

In certain embodiments, the compound is represented by Formula (Ie) or (If):

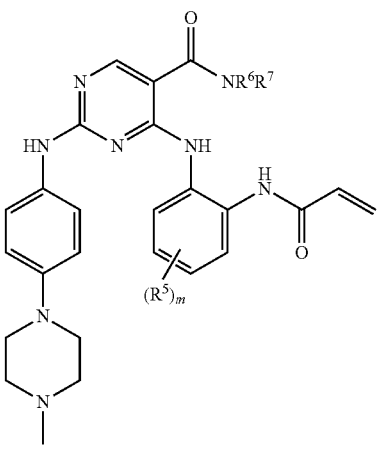

(Ie)

(If)

or a pharmaceutically acceptable salt thereof, wherein:
$R^6$ is hydrogen or alkyl; and
$R^7$ is alkyl or aryl.

In certain embodiments, $R^6$ is hydrogen.

In certain embodiments, $R^7$ is aryl (e.g., phenyl). In certain embodiments, $R^7$ is substituted with alkyl, carboxyl, hydroxyl, hydroxyalkyl, alkoxy, halogen, nitro, acyl, acyloxy, amino, aminoalkyl, aralkyl, aralkyloxy, or cyano. In certain embodiments, $R^7$ is substituted with alkyl (e.g., methyl or ethyl), aryloxy (e.g., phenyloxy), halo (e.g., chloro), carboxyl, alkoxy (e.g., methoxy), or cyano.

In certain preferred embodiments, m is 1.

In certain embodiments, $R^5$ is alkyl (e.g., methyl or isopropyl) or halo (e.g., fluoro).

In certain embodiments, the compound is not

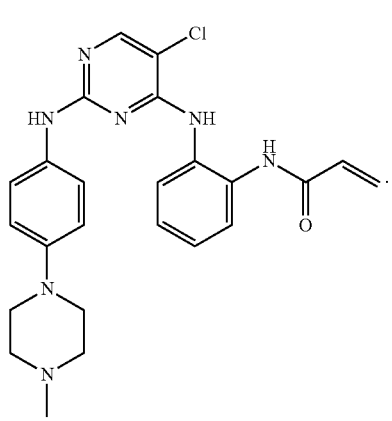

(SM1-71)

In certain embodiments, the compound is a compound of Table 1:
TABLE 1
Exemplary Compounds of the Present Disclosure
| Compound ID | Structure |
| --- | --- |
| 1 | 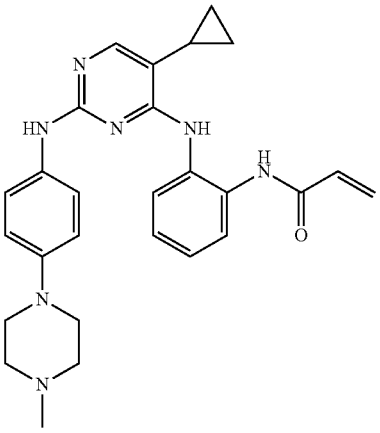 [SMILES: C=CC(=O)Nc1ccccc1Nc1nc(Nc2ccc(N3CCN(C)CC3)cc2)ncc1C1CC1] |
| 2 | 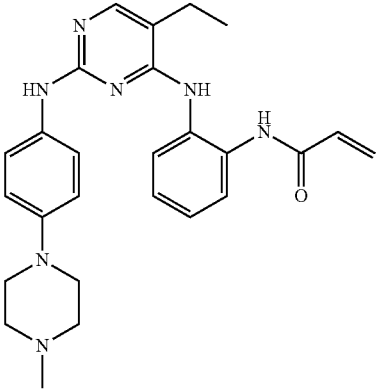 [SMILES: C=CC(=O)Nc1ccccc1Nc1nc(Nc2ccc(N3CCN(C)CC3)cc2)ncc1CC] |
| 3 | 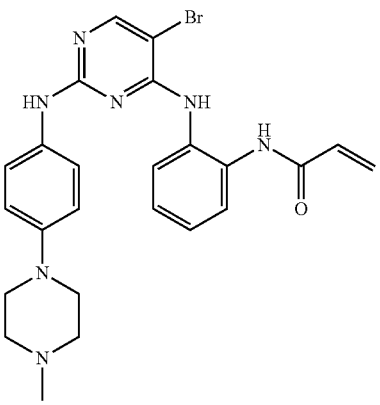 [SMILES: C=CC(=O)Nc1ccccc1Nc1nc(Nc2ccc(N3CCN(C)CC3)cc2)ncc1Br] |

TABLE 1-continued

Exemplary Compounds of the Present Disclosure

| Compound ID | Structure |
|---|---|
| 4 | *N-(2-((2-((4-(4-methylpiperazin-1-yl)phenyl)amino)-5-methylpyrimidin-4-yl)amino)phenyl)acrylamide* |
| 5 | *N-(2-((2-((4-(4-methylpiperazin-1-yl)phenyl)amino)-5-iodopyrimidin-4-yl)amino)phenyl)acrylamide* |
| 6 | *N-(2-((2-((4-(4-methylpiperazin-1-yl)phenyl)amino)-5-(thiophen-2-yl)pyrimidin-4-yl)amino)phenyl)acrylamide* |

TABLE 1-continued

Exemplary Compounds of the Present Disclosure

| Compound ID | Structure |
|---|---|
| 7 | 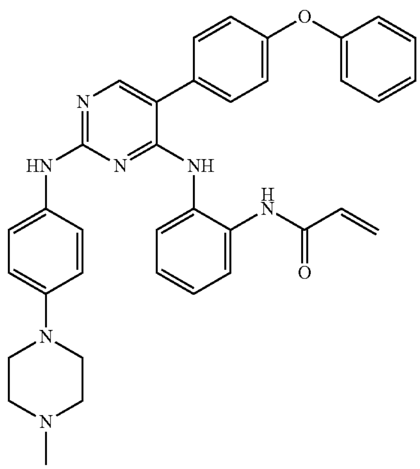 [SMILES: C=CC(=O)Nc1ccccc1Nc1nc(Nc2ccc(N3CCN(C)CC3)cc2)ncc1-c1ccc(Oc2ccccc2)cc1] |
| 8 | 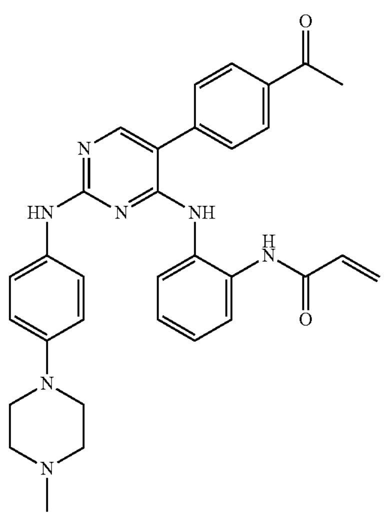 [SMILES: C=CC(=O)Nc1ccccc1Nc1nc(Nc2ccc(N3CCN(C)CC3)cc2)ncc1-c1ccc(C(C)=O)cc1] |
| 9 | 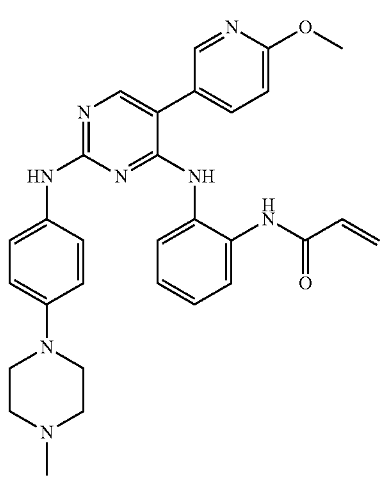 [SMILES: C=CC(=O)Nc1ccccc1Nc1nc(Nc2ccc(N3CCN(C)CC3)cc2)ncc1-c1ccc(OC)nc1] |

TABLE 1-continued
Exemplary Compounds of the Present Disclosure
| Compound ID | Structure |
|---|---|
| 10 | 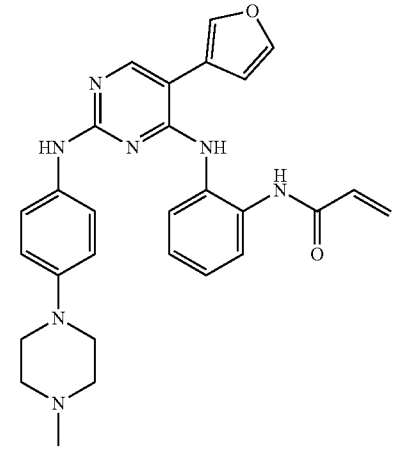 [SMILES: C=CC(=O)Nc1ccccc1Nc1nc(Nc2ccc(N3CCN(C)CC3)cc2)ncc1-c1ccoc1] |
| 11 | 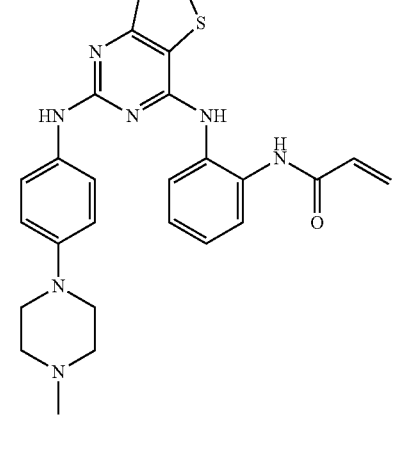 |
| 12 | 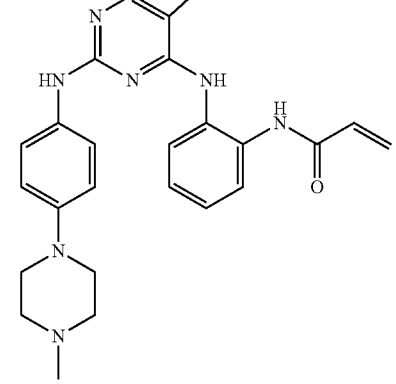 |

TABLE 1-continued
Exemplary Compounds of the Present Disclosure
| Compound ID | Structure |
|---|---|
| 13 | 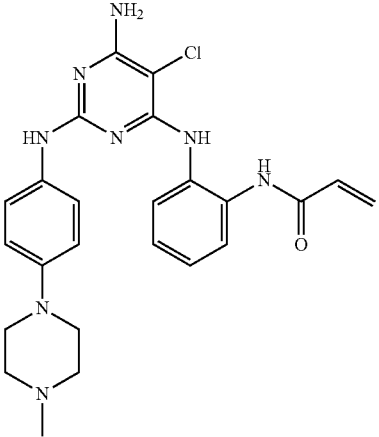 [SMILES: C=CC(=O)Nc1ccccc1Nc1nc(Nc2ccc(N3CCN(C)CC3)cc2)nc(N)c1Cl] |
| 14 | 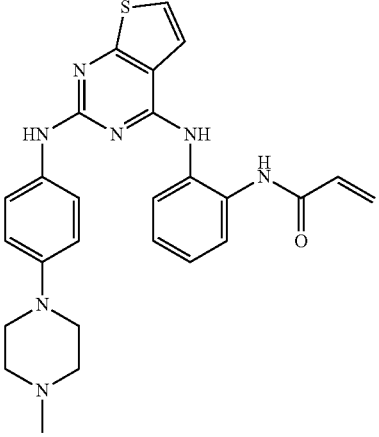 [SMILES: C=CC(=O)Nc1ccccc1Nc1nc(Nc2ccc(N3CCN(C)CC3)cc2)nc2sccc12] |
| 15 | 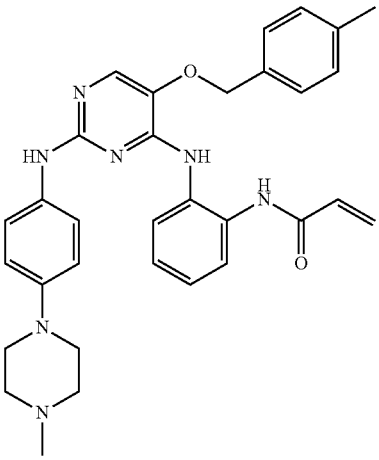 [SMILES: C=CC(=O)Nc1ccccc1Nc1nc(Nc2ccc(N3CCN(C)CC3)cc2)ncc1OCc1ccc(C)cc1] |

TABLE 1-continued

Exemplary Compounds of the Present Disclosure

| Compound ID | Structure |
|---|---|
| 16 | 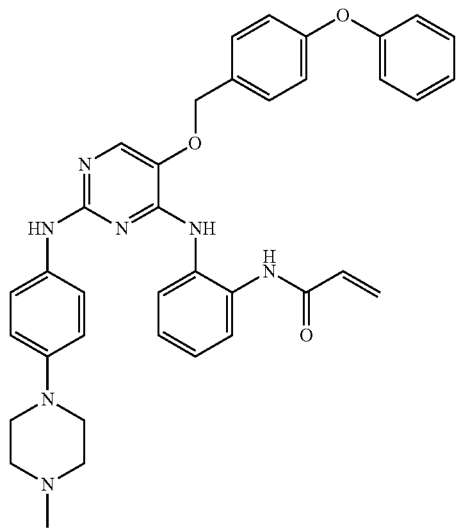 [SMILES: C=CC(=O)Nc1ccccc1Nc1nc(Nc2ccc(N3CCN(C)CC3)cc2)ncc1OCc1ccc(Oc2ccccc2)cc1] |
| 17 | 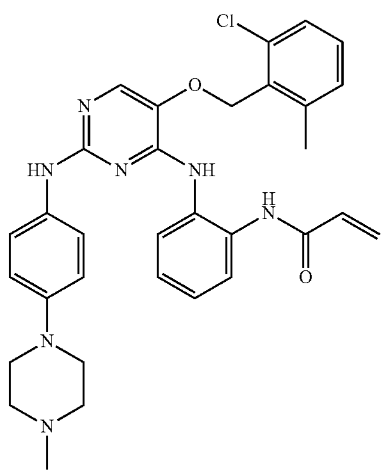 [SMILES: C=CC(=O)Nc1ccccc1Nc1nc(Nc2ccc(N3CCN(C)CC3)cc2)ncc1OCc1c(C)cccc1Cl] |
| 18 | 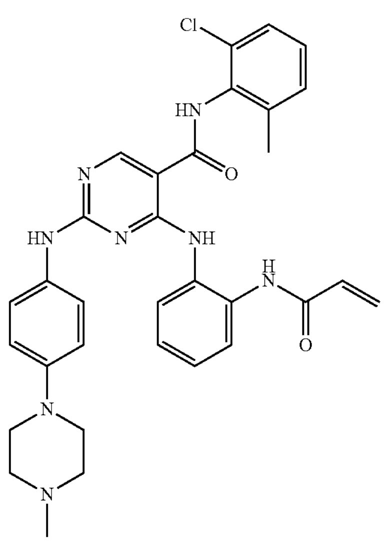 |

TABLE 1-continued
Exemplary Compounds of the Present Disclosure
| Compound ID | Structure |
|---|---|
| 19 | 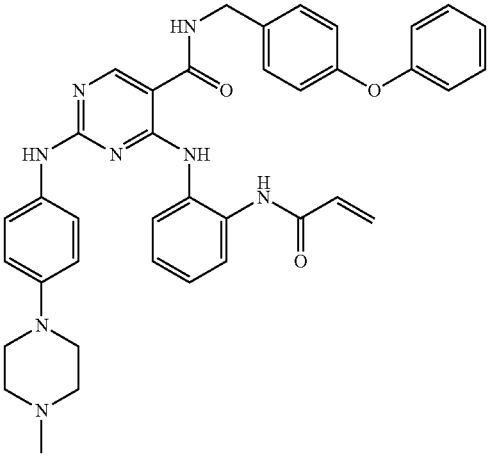 [SMILES: C=CC(=O)Nc1ccccc1Nc1nc(Nc2ccc(N3CCN(C)CC3)cc2)ncc1C(=O)NCc1ccc(Oc2ccccc2)cc1] |
| 20 | 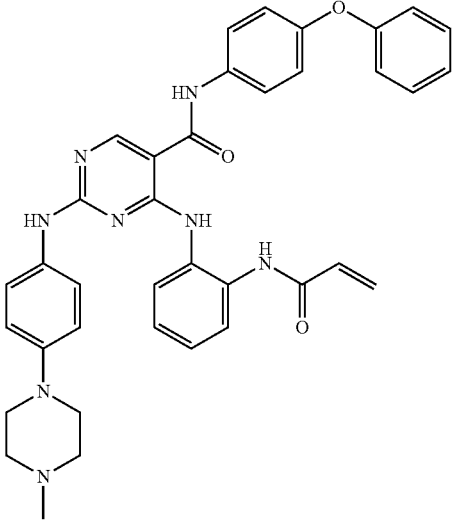 [SMILES: C=CC(=O)Nc1ccccc1Nc1nc(Nc2ccc(N3CCN(C)CC3)cc2)ncc1C(=O)Nc1ccc(Oc2ccccc2)cc1] |
| 21 | 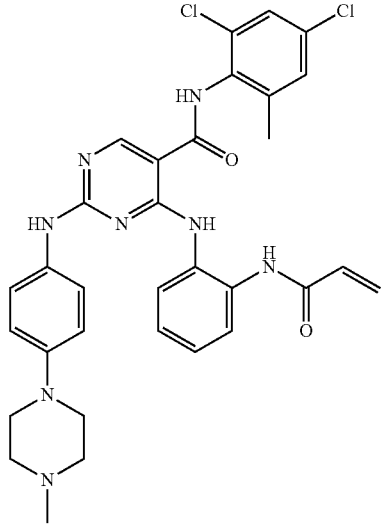 |

TABLE 1-continued
Exemplary Compounds of the Present Disclosure
| Compound ID | Structure |
|---|---|
| 22 | 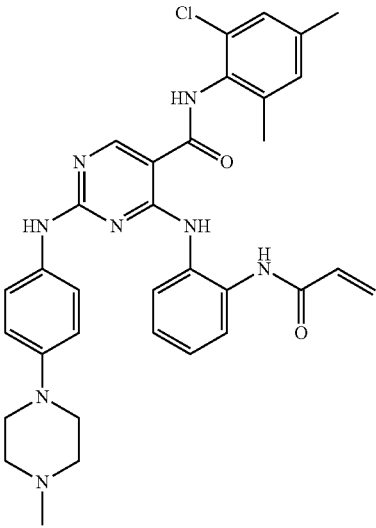 |
| 23 | 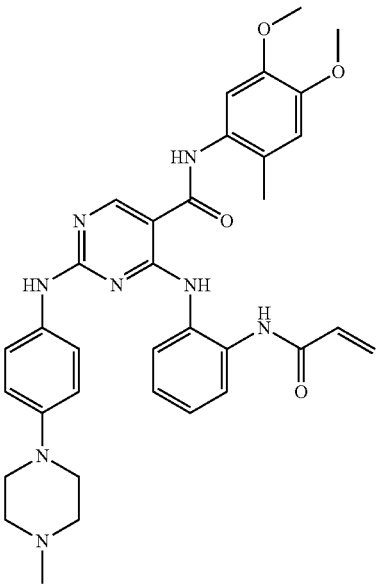 [SMILES: C=CC(=O)Nc1ccccc1Nc1nc(Nc2ccc(N3CCN(C)CC3)cc2)ncc1C(=O)Nc1cc(OC)c(OC)cc1C] |

TABLE 1-continued
Exemplary Compounds of the Present Disclosure
| Compound ID | Structure |
|---|---|
| 24 | 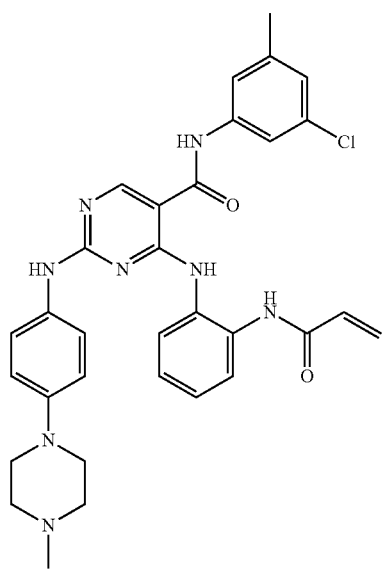 [SMILES: C=CC(=O)Nc1ccccc1Nc1nc(Nc2ccc(N3CCN(C)CC3)cc2)ncc1C(=O)Nc1cc(C)cc(Cl)c1] |
| 25 | 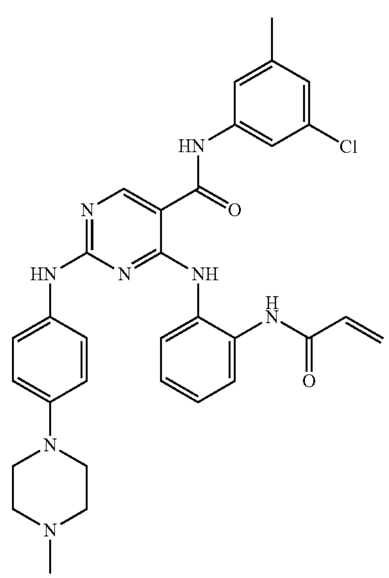 |

TABLE 1-continued
Exemplary Compounds of the Present Disclosure
| Compound ID | Structure |
|---|---|
| 26 | 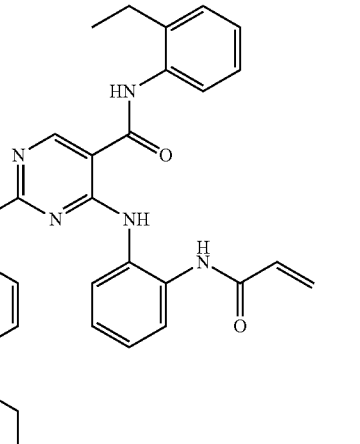 |
| 27 | 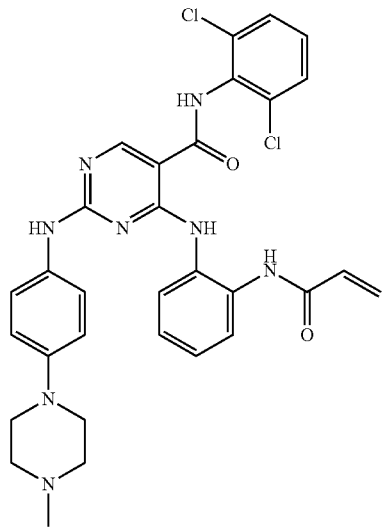 |

TABLE 1-continued
Exemplary Compounds of the Present Disclosure
| Compound ID | Structure |
|---|---|
| 28 | 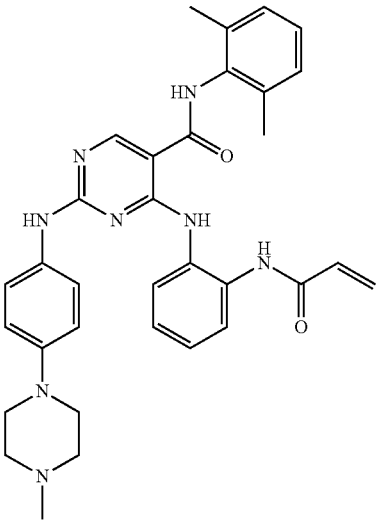 |
| 29 | 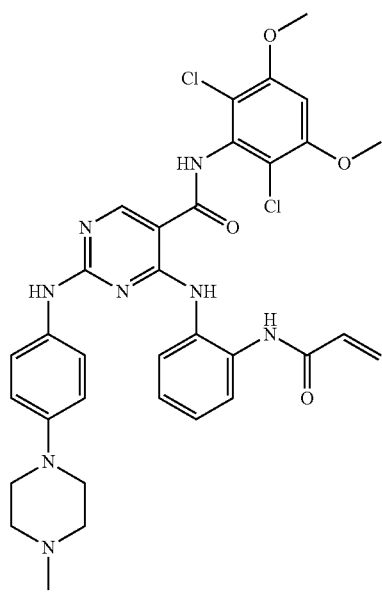 [SMILES: C=CC(=O)Nc1ccccc1Nc1nc(Nc2ccc(N3CCN(C)CC3)cc2)ncc1C(=O)Nc1c(Cl)c(OC)cc(OC)c1Cl] |

TABLE 1-continued

Exemplary Compounds of the Present Disclosure

| Compound ID | Structure |
|---|---|
| 30 | 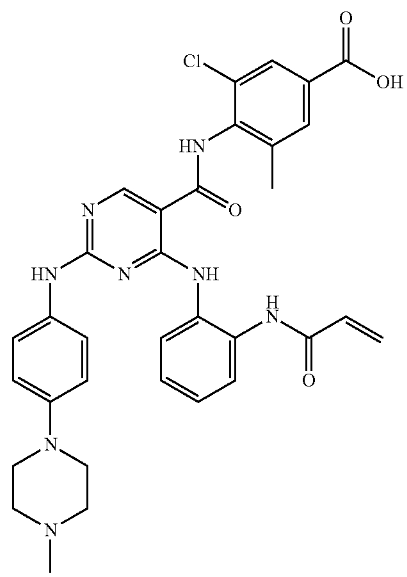 [SMILES: C=CC(=O)Nc1ccccc1Nc1nc(Nc2ccc(N3CCN(C)CC3)cc2)ncc1C(=O)Nc1c(C)cc(C(=O)O)cc1Cl] |
| 31 | 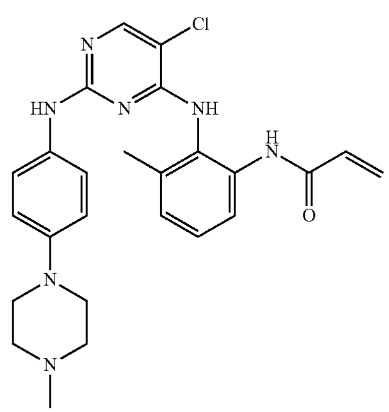 [SMILES: C=CC(=O)Nc1cccc(C)c1Nc1nc(Nc2ccc(N3CCN(C)CC3)cc2)ncc1Cl] |
| 32 | 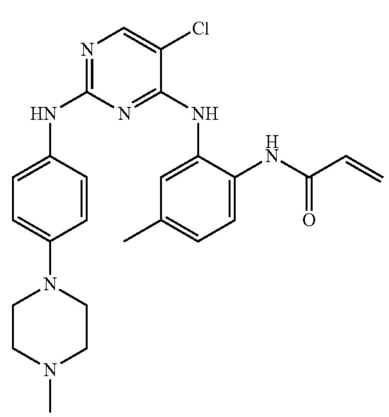 [SMILES: C=CC(=O)Nc1ccc(C)cc1Nc1nc(Nc2ccc(N3CCN(C)CC3)cc2)ncc1Cl] |

TABLE 1-continued
Exemplary Compounds of the Present Disclosure
| Compound ID | Structure |
|---|---|
| 33 | 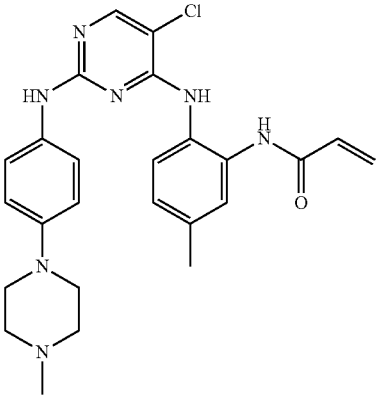 [SMILES: C=CC(=O)Nc1cc(C)ccc1Nc1nc(Nc2ccc(N3CCN(C)CC3)cc2)ncc1Cl] |
| 34 | 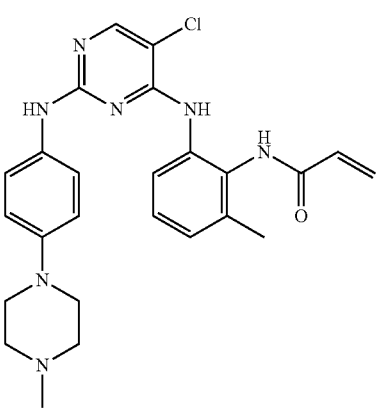 [SMILES: C=CC(=O)Nc1c(C)cccc1Nc1nc(Nc2ccc(N3CCN(C)CC3)cc2)ncc1Cl] |
| 35 | 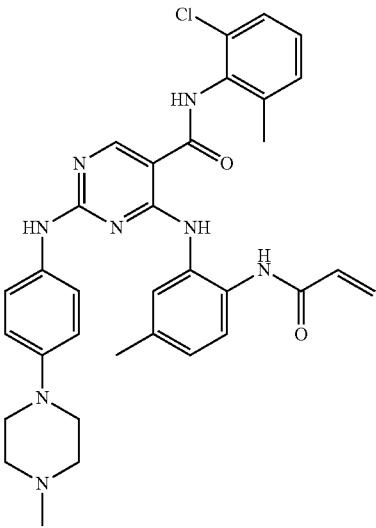 |

TABLE 1-continued
Exemplary Compounds of the Present Disclosure
| Compound ID | Structure |
|---|---|
| 36 | 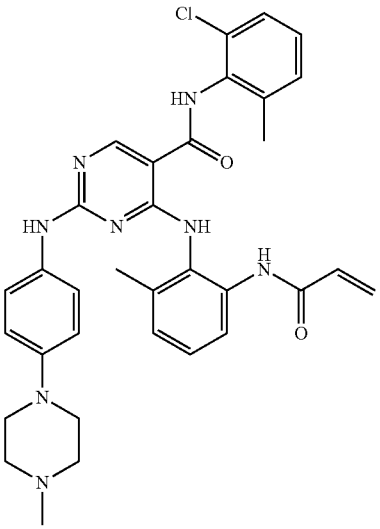 |
| 37 | 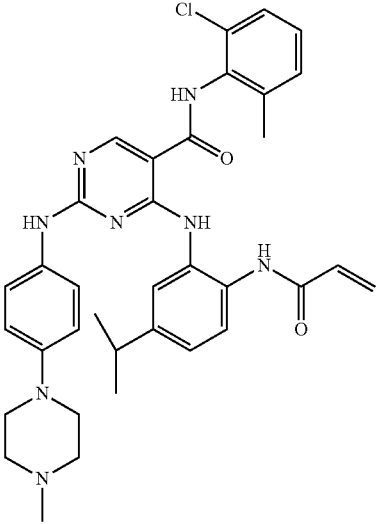 [SMILES: C=CC(=O)Nc1ccc(C(C)C)cc1Nc1nc(Nc2ccc(N3CCN(C)CC3)cc2)ncc1C(=O)Nc1c(C)cccc1Cl] |
| 38 | 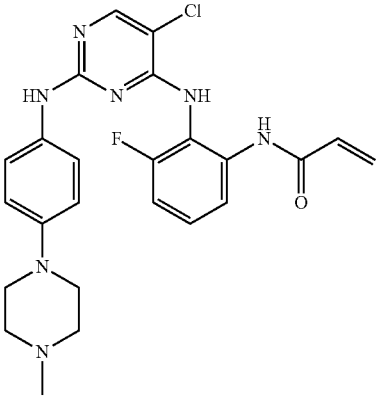 |

TABLE 1-continued
Exemplary Compounds of the Present Disclosure
| Compound ID | Structure |
|---|---|
| 39 | 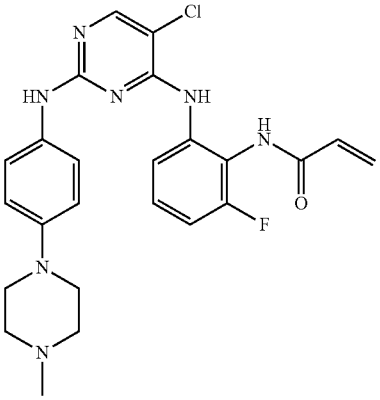 |
| 40 | 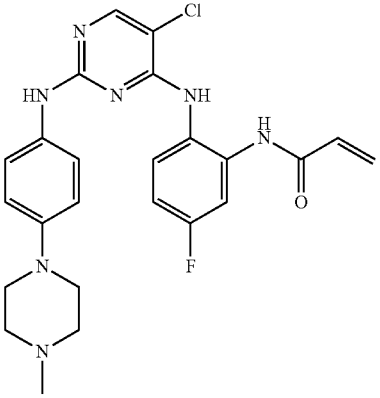 |
| 41 | 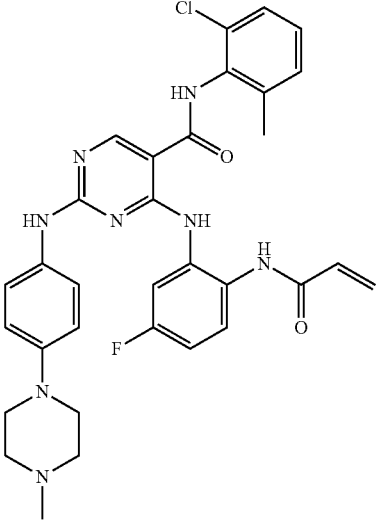 |

TABLE 1-continued
Exemplary Compounds of the Present Disclosure
| Compound ID | Structure |
|---|---|
| 42 | 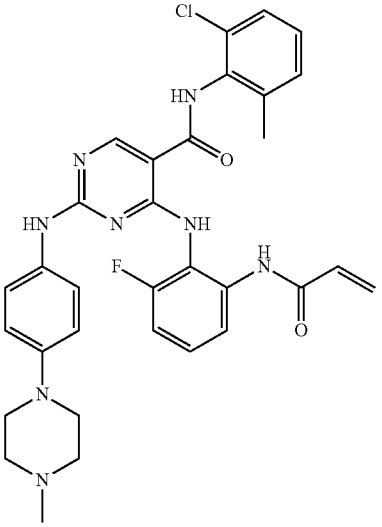 |
| 43 | 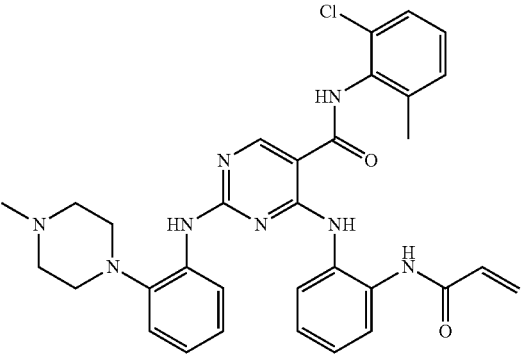 [SMILES: C=CC(=O)Nc1ccccc1Nc1nc(Nc2ccccc2N2CCN(C)CC2)ncc1C(=O)Nc1c(C)cccc1Cl] |
| 44 | 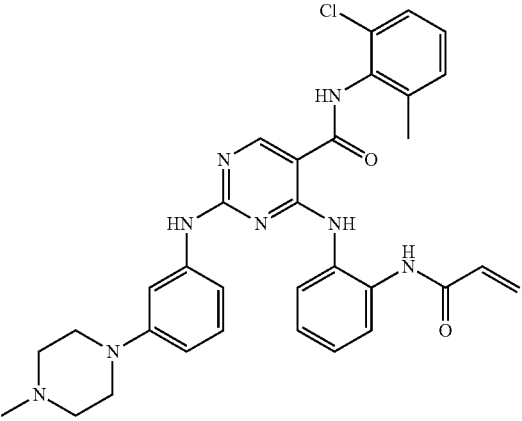 [SMILES: C=CC(=O)Nc1ccccc1Nc1nc(Nc2cccc(N3CCN(C)CC3)c2)ncc1C(=O)Nc1c(C)cccc1Cl] |

TABLE 1-continued
Exemplary Compounds of the Present Disclosure
| Compound ID | Structure |
|---|---|
| 45 | 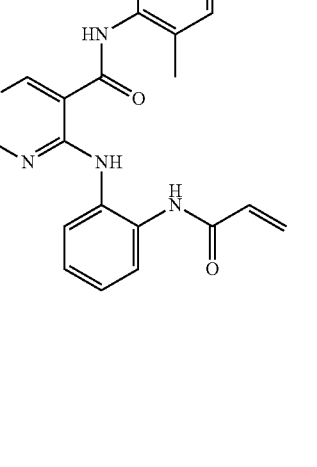 |
| 46 | 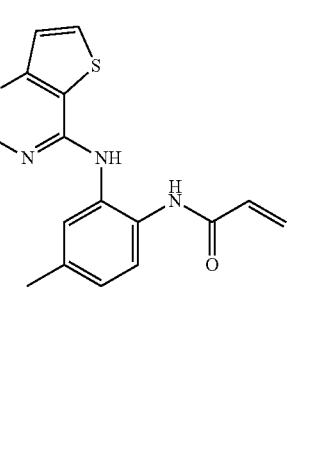 |
| 47 | 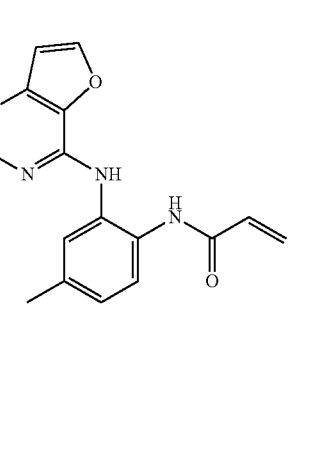 |

TABLE 1-continued
Exemplary Compounds of the Present Disclosure
| Compound ID | Structure |
|---|---|
| 48 | 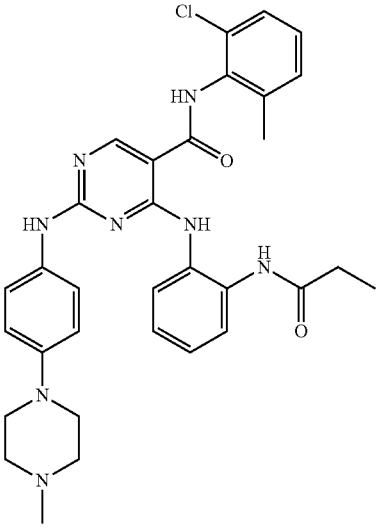 [SMILES: CCC(=O)Nc1ccccc1Nc1nc(Nc2ccc(N3CCN(C)CC3)cc2)ncc1C(=O)Nc1c(C)cccc1Cl] |
| 49 | 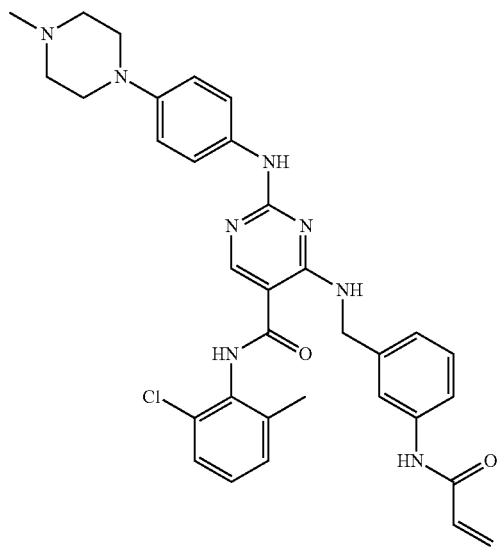 [SMILES: C=CC(=O)Nc1cccc(CNc2nc(Nc3ccc(N4CCN(C)CC4)cc3)ncc2C(=O)Nc2c(C)cccc2Cl)c1] |

TABLE 1-continued
Exemplary Compounds of the Present Disclosure
| Compound ID | Structure |
|---|---|
| 50 | 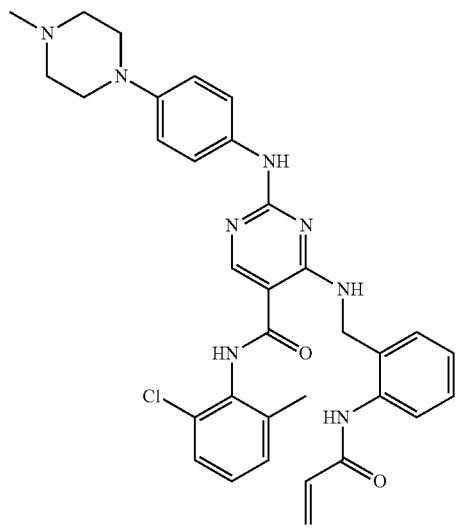 [SMILES: C=CC(=O)Nc1ccccc1CNc1nc(Nc2ccc(N3CCN(C)CC3)cc2)ncc1C(=O)Nc1c(C)cccc1Cl] |
| 51 | 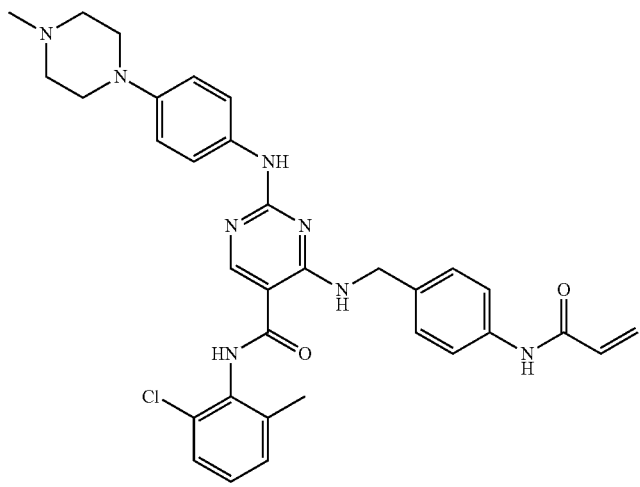 [SMILES: C=CC(=O)Nc1ccc(CNc2nc(Nc3ccc(N4CCN(C)CC4)cc3)ncc2C(=O)Nc2c(C)cccc2Cl)cc1] |
| 52 | 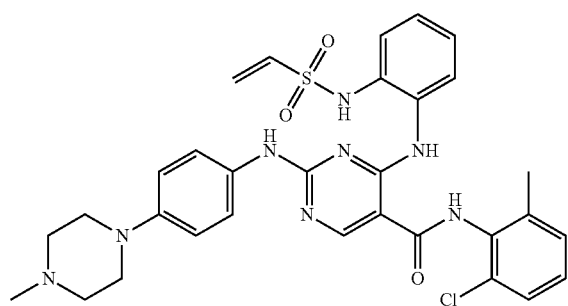 [SMILES: C=CS(=O)(=O)Nc1ccccc1Nc1nc(Nc2ccc(N3CCN(C)CC3)cc2)ncc1C(=O)Nc1c(C)cccc1Cl] |

TABLE 1-continued
Exemplary Compounds of the Present Disclosure
| Compound ID | Structure |
|---|---|
| 53 | 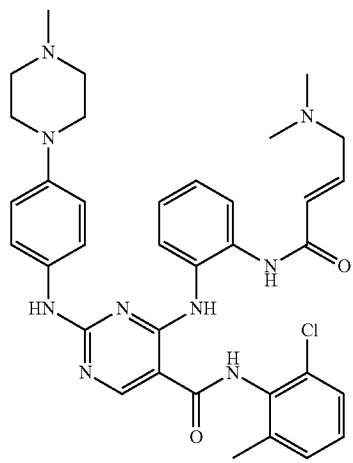 [SMILES: Cc1cccc(Cl)c1NC(=O)c1cnc(Nc2ccc(N3CCN(C)CC3)cc2)nc1Nc1ccccc1NC(=O)/C=C/CN(C)C] |
| 54 | 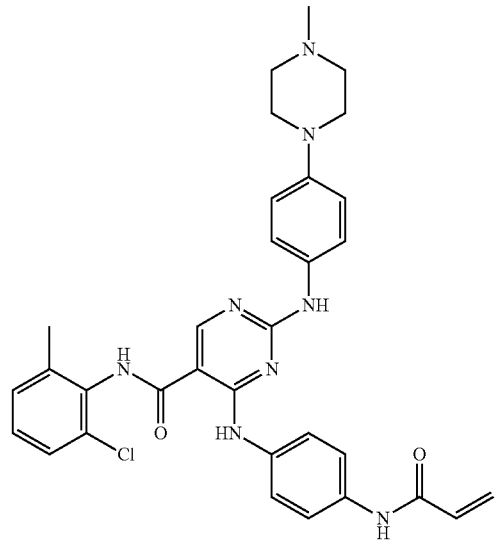 [SMILES: C=CC(=O)Nc1ccc(Nc2nc(Nc3ccc(N4CCN(C)CC4)cc3)ncc2C(=O)Nc2c(C)cccc2Cl)cc1] |

TABLE 1-continued

Exemplary Compounds of the Present Disclosure

| Compound ID | Structure |
|---|---|
| 55 | 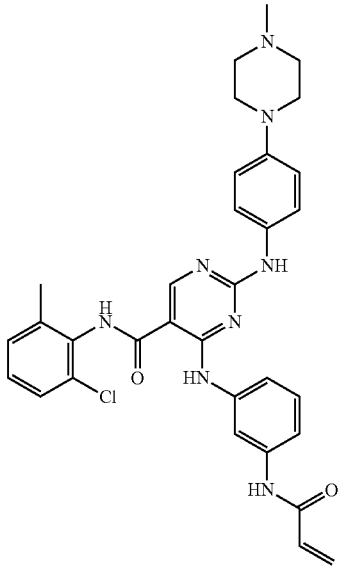 [SMILES: C=CC(=O)Nc1cccc(Nc2nc(Nc3ccc(N4CCN(C)CC4)cc3)ncc2C(=O)Nc2c(C)cccc2Cl)c1] |
| 56 | 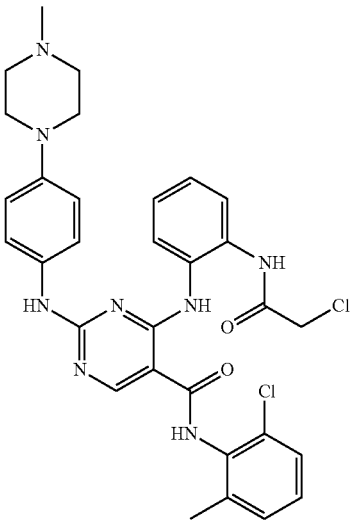 [SMILES: Cc1cccc(Cl)c1NC(=O)c1cnc(Nc2ccc(N3CCN(C)CC3)cc2)nc1Nc1ccccc1NC(=O)CCl] |

In certain embodiments, the compound is not compound 48.

In certain embodiments, the compound is a pharmaceutically acceptable salt of a compound of Table 1.

In one aspect, the present disclosure provides a pharmaceutical composition comprising a compound of Formula (I) and at least one pharmaceutically acceptable excipient.

In one aspect, the present disclosure provides a method of inhibiting a kinase in a cell comprising contacting the cell with a compound of Formula (I) or a composition thereof.

In certain embodiments, the kinase is selected from SRC, YES1, LYN A, HCK, TNK(ACK), and FGFR1. In certain preferred embodiments, the kinase is SRC.

In one aspect, the present disclosure provides a method of treating cancer in a subject in need thereof comprising administering to the subject an effective amount of a compound of Formula (I) or a composition thereof.

In certain embodiments, the cancer over expresses a kinase is selected from SRC, YES1, LYN A, HCK, TNK (ACK), and FGFR1. In certain preferred embodiments, the cancer over expresses SRC.

In certain embodiments, the cancer is selected from a solid tumor, benign or malignant tumor, carcinoma of the brain, kidney, liver, stomach, vagina, ovaries, gastric tumors, breast, bladder, colon, prostate, pancreas, lung, cervix, testis, skin, bone or thyroid; sarcoma, glioblastoma, neuroblastoma, gastrointestinal cancer, a tumor of the neck and head, an epidermal hyperproliferation, psoriasis, prostate hyperplasia, a neoplasia, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, papillary carcinoma, seminoma, melanoma; hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulinemia (WM), splenic marginal zone lymphoma, intravascular large B-cell lymphoma, plasmacytoma and multiple myeloma.

In certain preferred embodiments, the cancer is breast, colon, or lung cancer.

In certain embodiments, the cancer is refractory. In certain embodiments, the cancer is refractory to treatment with Trastuzumab.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino) ethanol, ethanolamine, ethylenediamine, N-methylglucamine, hydrabamine, 1H-imidazole, lithium, L-lysine, magnesium, 4-(2-hydroxyethyl) morpholine, piperazine, potassium, 1-(2-hydroxyethyl) pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

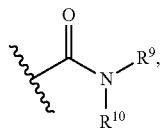

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

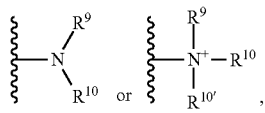

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

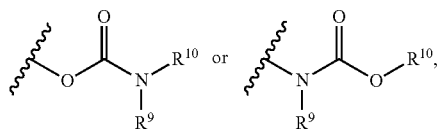

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —$C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

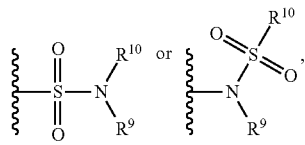

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

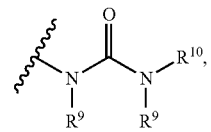

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds

General Procedure 1A—4-chloropyrimidine substitution: substituted 4-chloropyrimidine (1.0 eq.) was suspended in n-BuOH at rt, followed by the addition of DIEA (2.0 eq.) and substituted aniline (1.0 eq). The mixture was the refluxed for 3 hours, the solvent evaporated, and crude residue purified by silica gel chromatography to provide the substituted 4-aminopyrimidine.

General Procedure 1B—4-chloropyrimidine substitution: substituted 4-chloropyrimidine (1.0 eq.) was suspended in n-BuOH at rt, followed by the addition of DIEA (2.0 eq.) and 4-(4-methylpiperazin-1-yl) aniline (1.0 eq). The mixture was stirred at rt for 3 hours, the solvent evaporated, and crude residue purified by silica gel chromatography to provide the substituted 4-aminopyrimidine.

General Procedure 2—2-chloropyrimidine substitution: substituted 2-chloro-4-aminopyrimidine (1.0 eq.) was suspended in 2-BuOH (0.2 M), and TFA (1.5 eq.) was added followed by aniline (1.0 eq.). The mixture was then refluxed for 3 hours, the solvent evaporated, and crude residue purified by silica gel chromatography to provide the substituted 2,4-diaminopyrimidine.

General Procedure 3—Acrylamide formation: Aniline was dissolved in a 1:1 mixture of THF and sat. aqueous NaHCO$_3$. At 0° C., a solution of acryloyl chloride dissolved in THF was slowly titrated in until the aniline was consumed. The mixture was then diluted with water and extracted with EtOAc. Combined extracts were washed with brine, dried with Na$_2$SO$_4$, concentrated and purified by HPLC to obtain the products.

General Procedure 4—Suzuki coupling: aryl bromide (1 eq.), boronic acid (1.5 eq.), PdCl$_2$(dppf)·DCM (0.2 eq.), and K$_3$PO$_4$ (6.0 eq.) were added to a mixture of dioxane: water (4:1, ~0.1 M bromide). The mixture was degassed by sonication and sparged with N$_2$, then stirred at 80° C. for 3 hours. The reaction was then filtered, diluted with water and extracted with EtOAc. Combined extracts were washed with brine, dried with Na$_2$SO$_4$, concentrated and purified by silica gel chromatography to provide the biaryl products.

Synthesis of N-{2-[(5-cyclopropyl-2-{[4-(4-methylpiperazin-1-yl)phenyl]amino}pyrimidin-4-yl)amino]phenyl}prop-2-enamide (1)

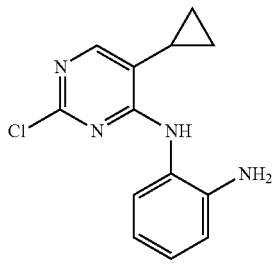 [SMILES: Nc1ccccc1Nc1nc(Cl)ncc1C1CC1]

N₁-(2-chloro-5-cyclopropylpyrimidin-4-yl)benzene-1,2-diamine: 2,4-dichloro-5-cyclopropylpyrimidine and 1,2-diaminobenzene were reacted as described in General Procedure 1A. LC/MS: m/z calculated for [M+H]+261.08, found 260.97.

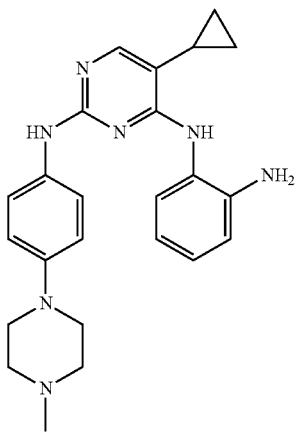 [SMILES: CN1CCN(c2ccc(Nc3ncc(C4CC4)c(Nc4ccccc4N)n3)cc2)CC1]

N4-(2-aminophenyl)-5-cyclopropyl-N2-(4-(4-methylpiperazin-1-yl)phenyl)pyrimidine-2,4-diamine: N1-(2-chloro-5-cyclopropylpyrimidin-4-yl)benzene-1,2-diamine and 4-(4-methylpiperazin-1-yl) aniline were reacted as described in General Procedure 2. LC/MS: m/z calculated for [M+H]+ 416.25, found 416.17.

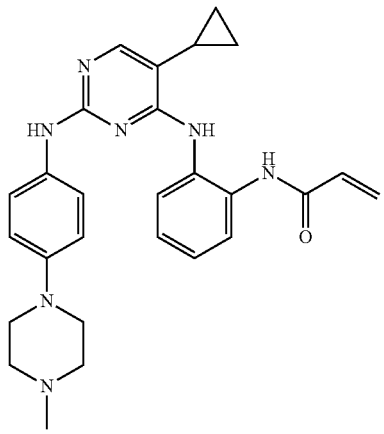 [SMILES: C=CC(=O)Nc1ccccc1Nc1nc(Nc2ccc(N3CCN(C)CC3)cc2)ncc1C1CC1]

N-{2-[(5-cyclopropyl-2-{[4-(4-methylpiperazin-1-yl)phenyl]amino}pyrimidin-4-yl)amino]phenyl}prop-2-enamide (1): The acrylamide was installed on N4-(2-aminophenyl)-5-cyclopropyl-N2-(4-(4-methylpiperazin-1-yl)phenyl)pyrimidine-2,4-diamine as described in General Procedure 3, and the products purified by HPLC to obtain the title compound. LC/MS: m/z calculated for [M+H]+470.26, found 470.08.

Synthesis of N-{2-[(5-ethyl-2-{[4-(4-methylpiperazin-1-yl)phenyl]amino}pyrimidin-4-yl)amino]phenyl}prop-2-enamide (2)

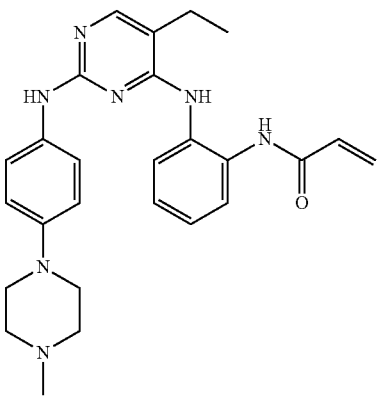

N-{2-[(5-ethyl-2-{[4-(4-methylpiperazin-1-yl)phenyl]amino}pyrimidin-4-yl)amino]phenyl}prop-2-enamide (2) was synthesized using the same synthetic route as used for (1). LC/MS: m/z calculated for [M+H]+458.26, found 457.98.

Synthesis of N-{2-[(5-bromo-2-{[4-(4-methylpiperazin-1-yl)phenyl]amino}pyrimidin-4-yl)amino]phenyl}prop-2-enamide (3)

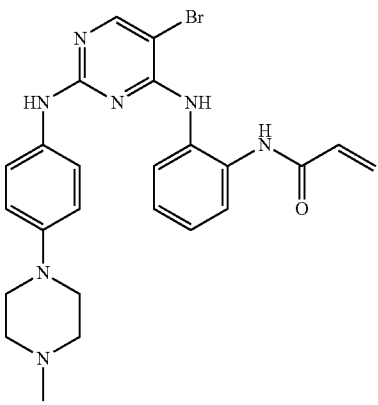

N-{2-[(5-bromo-2-{[4-(4-methylpiperazin-1-yl)phenyl]amino}pyrimidin-4-yl)amino]phenyl}prop-2-enamide (3) was synthesized using the same synthetic route as used for (1). LC/MS: m/z calculated for [M+H]+508.14, found 508.28.

Synthesis of N-{2-[(5-methyl-2-{[4-(4-methylpiperazin-1-yl)phenyl]amino}pyrimidin-4-yl)amino]phenyl}prop-2-enamide (4)

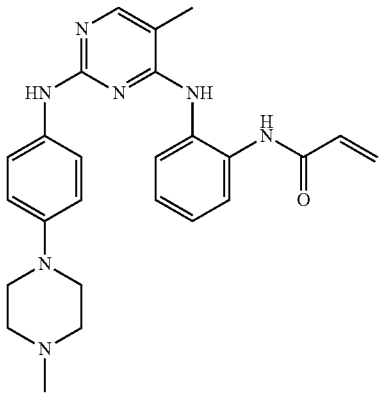 [SMILES: C=CC(=O)Nc1ccccc1Nc1nc(Nc2ccc(N3CCN(C)CC3)cc2)ncc1C]

N-{2-[(5-methyl-2-{[4-(4-methylpiperazin-1-yl)phenyl]amino}pyrimidin-4-yl)amino]phenyl}prop-2-enamide (4) was synthesized using the same synthetic route as used for (1). LC/MS: m/z calculated for [M+H]+444.24, found 444.38.

Synthesis of N-{2-[(5-iodo-2-{[4-(4-methylpiperazin-1-yl)phenyl]amino}pyrimidin-4-yl)amino]phenyl}prop-2-enamide (5)

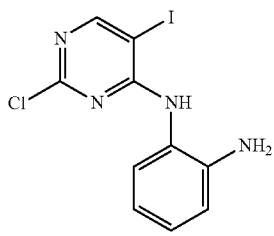 [SMILES: Nc1ccccc1Nc1nc(Cl)ncc1I]

N1-(2-chloro-5-iodopyrimidin-4-yl)benzene-1,2-diamine: 1,2-diaminobenzene was added to a solution of 2,4-dichloro-5-iodo-pyrmidine (100 mg, 0.36 mmol) and DIEA (126 µL, 0.72 mmol) in THF (2 mL). The mixture was stirred for 2 days at rt, the solvent evaporated and the crude residue purified by silica gel chromatography to provide the title compound (107 mg, 0.31 mmol, 86%). LC/MS: m/z calculated for [M+H]+346.95, found 347.09.

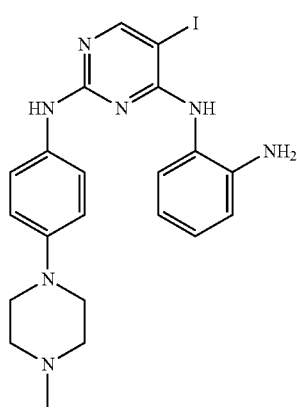 [SMILES: CN1CCN(c2ccc(Nc3ncc(I)c(Nc4ccccc4N)n3)cc2)CC1]

N4-(2-aminophenyl)-5-iodo-N2-(4-(4-methylpiperazin-1-yl)phenyl)pyrimidine-2,4-diamine: 4-(4-methylpiperazin-1-yl) aniline (59 mg, 0.31 mmol) was added to N1-(2-chloro-5-iodopyrimidin-4-yl)benzene-1,2-diamine (107 mg, 0.31 mmol) in 2-butanol (2 mL) and TFA (47 µL, 0.62 mmol). The reaction was stirred for 3 hours at 50° C. The solvent was removed and the residue purified by silica gel chromatography to provide the title compound (105 mg, 0.21 mmol, 66%). LC/MS: m/z calculated for [M+H]+ 502.11, found 502.38.

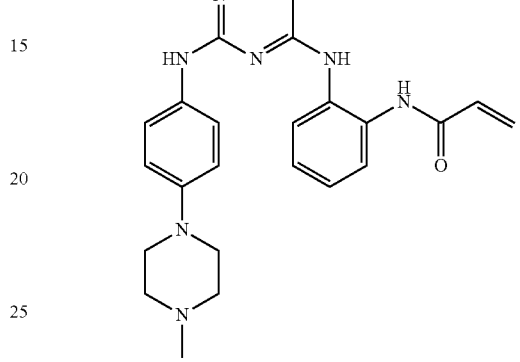

N-{2-[(5-iodo-2-{[4-(4-methylpiperazin-1-yl)phenyl]amino}pyrimidin-4-yl)amino]phenyl}prop-2-enamide (5): The acrylamide was installed on N4-(2-aminophenyl)-5-iodo-N2-(4-(4-methylpiperazin-1-yl)phenyl)pyrimidine-2,4-diamine as described in General Procedure 3, and the products purified by HPLC to obtain the title compound (23%). LC/MS: m/z calculated for [M+H]+556.12, found 556.29.

Synthesis of N-(2-((2-((4-(4-methylpiperazin-1-yl)phenyl)amino)-5-(thiophen-2-yl)pyrimidin-4-yl)amino)phenyl)acrylamide (6)

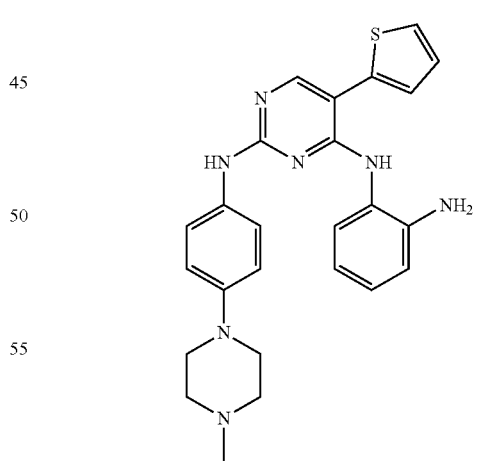

N4-(2-aminophenyl)-N2-(4-(4-methylpiperazin-1-yl)phenyl)-5-(thiophen-2-yl)pyrimidine-2,4-diamine: N4-(2-aminophenyl)-5-bromo-N2-(4-(4-methylpiperazin-1-yl)phenyl)pyrimidine-2,4-diamine and thiophen-2-ylboronic acid were reacted and purified as described in General Procedure 4. LC/MS: m/z calculated for [M+H]+457.20, found 456.88.

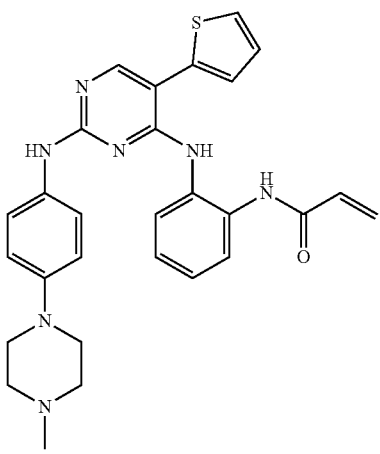 [SMILES: C=CC(=O)Nc1ccccc1Nc1nc(Nc2ccc(N3CCN(C)CC3)cc2)ncc1-c1cccs1]

N-(2-((2-((4-(4-methylpiperazin-1-yl)phenyl)amino)-5-(thiophen-2-yl)pyrimidin-4-yl)amino)phenyl)acrylamide (6): The acrylamide moiety was installed on N4-(2-aminophenyl)-N2-(4-(4-methylpiperazin-1-yl)phenyl)-5-(thiophen-2-yl)pyrimidine-2,4-diamine as described by General Procedure 3, and the products purified by HPLC to afford the title compound. LC/MS: m/z calculated for [M+H]+512.22, found 511.88. $^1$H NMR (500 MHz, DMSO-$d_6$) δ 10.18 (s, 1H), 9.80 (s, 2H), 8.53 (s, 1H), 8.03 (s, 1H), 7.84 (d, J=7.9 Hz, 1H), 7.69 (dd, J=4.9, 1.4 Hz, 1H), 7.40 (d, J=8.5 Hz, 2H), 7.38-7.31 (m, 2H), 7.30-7.25 (m, 1H), 7.23-7.17 (m, 2H), 6.87 (d, J=8.6 Hz, 2H), 6.41 (dd, J=17.0, 10.2 Hz, 1H), 6.15 (dd, J=17.0, 2.0 Hz, 1H), 5.78 (dd, J=10.1, 2.0 Hz, 1H), 3.75 (d, J=13.2 Hz, 2H), 3.53 (d, J=12.1 Hz, 2H), 3.18 (s, 2H), 2.96-2.84 (m, 5H).

Synthesis of N-(2-((2-((4-(4-methylpiperazin-1-yl)phenyl)amino)-5-(4-phenoxyphenyl)pyrimidin-4-yl)amino)phenyl)acrylamide (7)

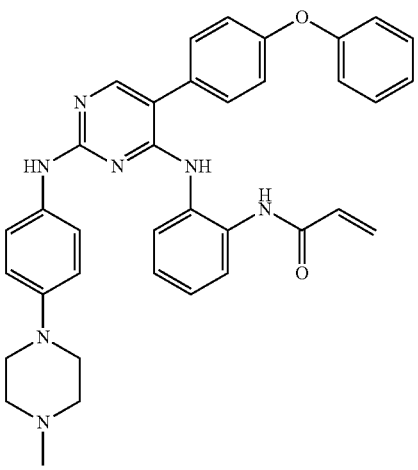 [SMILES: C=CC(=O)Nc1ccccc1Nc1nc(Nc2ccc(N3CCN(C)CC3)cc2)ncc1-c1ccc(Oc2ccccc2)cc1]

N-(2-((2-((4-(4-methylpiperazin-1-yl)phenyl)amino)-5-(4-phenoxyphenyl)pyrimidin-4-yl)amino)phenyl)acrylamide was synthesized using the same synthetic route as used for (6). LC/MS: m/z calculated for [M+H]+598.29, found 598.59. $^1$H NMR (500 MHz, DMSO-$d_6$) δ 10.10 (s, 1H), 9.77 (s, 2H), 8.41 (s, 1H), 7.86 (s, 1H), 7.75 (d, J=7.8 Hz, 1H), 7.39-7.31 (m, 6H), 7.30-7.23 (m, 2H), 7.22-7.15 (m, 1H), 7.15-7.09 (m, 1H), 7.07-7.00 (m, 4H), 6.81 (d, J=8.5 Hz, 2H), 6.32 (dd, J=17.0, 10.2 Hz, 1H), 6.01 (dd, J=17.0, 2.0 Hz, 1H), 5.65 (dd, J=10.1, 2.0 Hz, 1H), 3.68 (d, J=12.9 Hz, 2H), 3.46 (d, J=12.2 Hz, 2H), 3.17-3.03 (m, 2H), 2.89-2.77 (m, 5H).

Synthesis of N-(2-((5-(4-acetylphenyl)-2-((4-(4-methylpiperazin-1-yl)phenyl)amino)pyrimidin-4-yl)amino)phenyl)acrylamide (8)

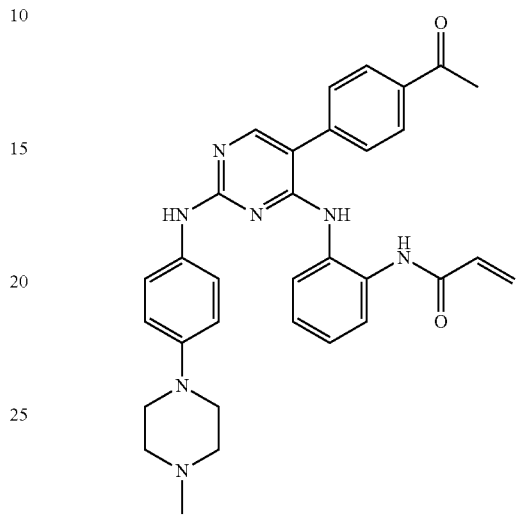

N-(2-((5-(4-acetylphenyl)-2-((4-(4-methylpiperazin-1-yl)phenyl)amino)pyrimidin-4-yl)amino)phenyl)acrylamide (8) was synthesized using the same synthetic route as used for (6). LC/MS: m/z calculated for [M+H]+548.27, found 548.49. $^1$H NMR (500 MHZ, DMSO-$d_6$) δ 10.13 (s, 1H), 9.85 (s, 1H) 9.82 (s, 1H), 8.50 (s, 1H), 8.05 (d, J=8.2 Hz, 2H), 8.01 (s, 1H), 7.82 (d, J=8.0 Hz, 1H), 7.63-7.58 (m, 2H), 7.44-7.36 (m, 3H), 7.35-7.30 (m, 1H), 7.29-7.21 (m, 1H), 6.87 (d, J=8.6 Hz, 2H), 6.40 (dd, J=16.9, 10.2 Hz, 1H), 6.01 (dd, J=17.1, 2.0 Hz, 1H), 5.75 (dd, J=10.1, 2.0 Hz, 1H), 3.75 (d, J=13.2 Hz, 2H), 3.54 (d, J=12.1 Hz, 2H), 3.17 (d, J=10.7 Hz, 2H), 2.92 (d, J=12.4 Hz, 2H), 2.88 (s, 3H), 2.64 (s, 3H).

Synthesis of N-(2-((5-(6-methoxypyridin-3-yl)-2-((4-(4-methylpiperazin-1-yl)phenyl)amino)pyrimidin-4-yl)amino)phenyl)acrylamide (9)

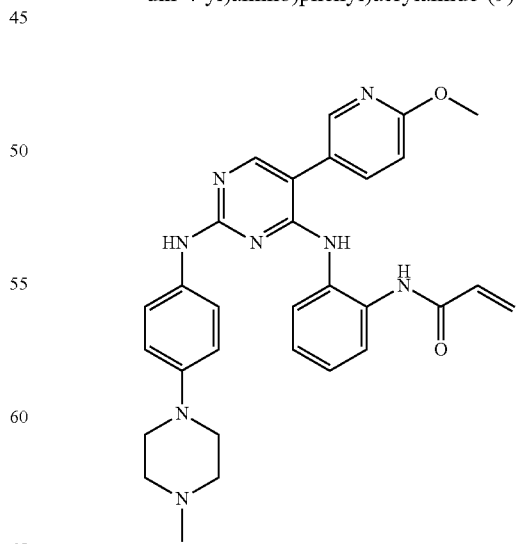

N-(2-((5-(6-methoxypyridin-3-yl)-2-((4-(4-methylpiperazin-1-yl)phenyl)amino)pyrimidin-4-yl)amino)phenyl)acrylamide (9) was synthesized using the same synthetic route as used for (6). LC/MS: m/z calculated for [M+H]+537.26, found 537.39. $^1$H NMR (500 MHZ, DMSO-$d_6$) δ 10.04 (s, 1H), 9.96 (s, 1H), 9.72 (s, 1H), 8.62 (s, 1H), 8.13 (d, J=2.4 Hz, 1H), 7.86 (s, 1H), 7.73-7.66 (m, 2H), 7.35 (dd, J=8.0, 1.7 Hz, 1H), 7.30 (d, J=8.4 Hz, 2H), 7.25 (td, J=7.7, 1.7 Hz, 1H), 7.20 (td, J=7.6, 1.6 Hz, 1H), 6.85 (d, J=8.6 Hz, 1H), 6.81 (d, J=8.6 Hz, 2H), 6.33 (dd, J=17.0, 10.2 Hz, 1H), 6.00 (dd, J=17.0, 2.0 Hz, 1H), 5.70 (dd, J=10.1, 2.0 Hz, 1H), 3.85 (s, 3H), 3.68 (d, J=13.3 Hz, 2H), 3.46 (d, J=12.2 Hz, 2H), 3.10 (d, J=10.9 Hz, 2H), 2.84 (d, J=12.2 Hz, 2H), 2.80 (s, 3H).

Synthesis of N-(2-((5-(furan-3-yl)-2-((4-(4-methylpiperazin-1-yl)phenyl)amino)pyrimidin-4-yl)amino)phenyl)acrylamide (10)

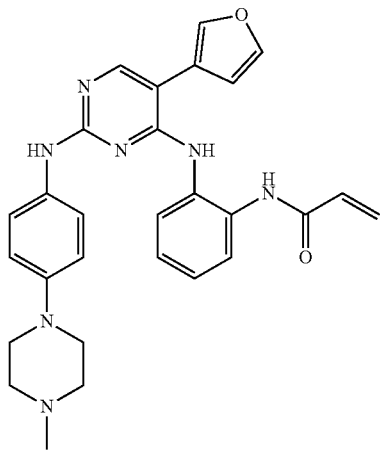 [SMILES: C=CC(=O)Nc1ccccc1Nc1nc(Nc2ccc(N3CCN(C)CC3)cc2)ncc1-c1ccoc1]

N-(2-((5-(furan-3-yl)-2-((4-(4-methylpiperazin-1-yl)phenyl)amino)pyrimidin-4-yl)amino)phenyl)acrylamide (10) was synthesized using the same synthetic route as used for (6). LC/MS: m/z calculated for [M+H]+496.24, found 496.38. $^1$H NMR (500 MHZ, DMSO-$d_6$) δ 10.16 (s, 1H), 9.94 (s, 1H), 9.81 (s, 1H), 8.57 (s, 1H), 8.02 (s, 1H), 7.94 (s, 1H), 7.85 (t, J=1.7 Hz, 1H), 7.78 (d, J=7.9 Hz, 1H), 7.44 (dd, J=7.8, 1.7 Hz, 1H), 7.39-7.31 (m, 3H), 7.29 (td, J=7.6, 1.6 Hz, 1H), 6.86 (d, J=8.6 Hz, 2H), 6.72 (d, J=1.8 Hz, 1H), 6.45 (dd, J=16.9, 10.2 Hz, 1H), 6.20 (dd, J=17.0, 2.0 Hz, 1H), 5.79 (dd, J=10.1, 2.0 Hz, 1H), 3.74 (d, J=13.1 Hz, 2H), 3.53 (d, J=12.2 Hz, 2H), 3.17 (s, 2H), 2.91 (d, J=11.5 Hz, 2H), 2.88 (s, 3H).

Synthesis of N-{2-[(2-{[4-(4-methylpiperazin-1-yl)phenyl]amino}thieno[3,2-d]pyrimidin-4-yl)amino]phenyl}prop-2-enamide (11)

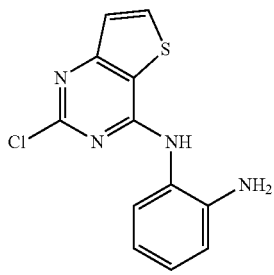 [SMILES: Nc1ccccc1Nc1nc(Cl)nc2ccsc12]

N1-(2-chlorothieno[3,2-d]pyrimidin-4-yl)benzene-1,2-diamine: 2,4-dichlorothieno[3,2-d]pyrimidine (205 mg, 1.0 mmol) was dissolved in methanol (5 mL), and 1,2-diaminobenzene (108 mg, 1.0 mmol) was added. After stirring overnight at rt, the solvent was evaporated and the residue purified by silica gel chromatography to provide the title compound. LC/MS: m/z calculated for [M+H]+277.02, found 277.07.

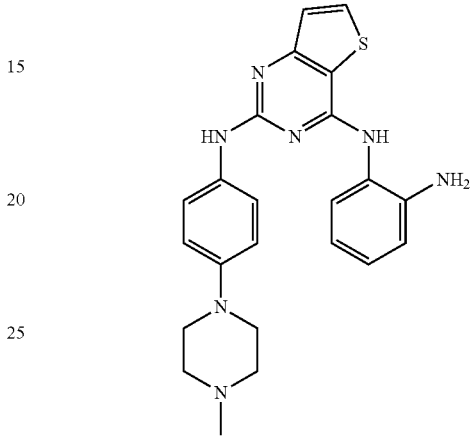

N4-(2-aminophenyl)-N2-(4-(4-methylpiperazin-1-yl)phenyl) thieno[3,2-d]pyrimidine-2,4-diamine: N1-(2-chlorothieno[3,2-d]pyrimidin-4-yl)benzene-1,2-diamine and 4-(4-methylpiperazin-1-yl) aniline were reacted and purified according to General Procedure 2. LC/MS: m/z calculated for [M+H]+432.19, found 431.97.

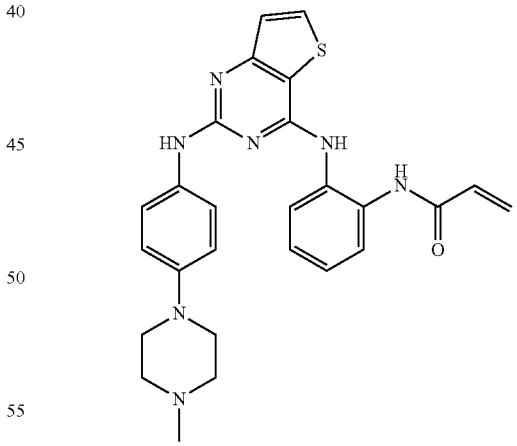

N-{2-[(2-{[4-(4-methylpiperazin-1-yl)phenyl]amino}thieno[3,2-d]pyrimidin-4-yl)amino]phenyl}prop-2-enamide (11): The acrylamide was installed on N4-(2-aminophenyl)-N2-(4-(4-methylpiperazin-1-yl)phenyl) thieno[3,2-d]pyrimidine-2,4-diamine as described in General Procedure Acryloyl, and the products purified by HPLC to obtain the title compound. LC/MS: m/z calculated for [M+H]+486.20, found 485.88.

Synthesis of N-{2-[(2-{[4-(4-methylpiperazin-1-yl)phenyl]amino}furo [3,2-d]pyrimidin-4-yl)amino]phenyl}prop-2-enamide (12)

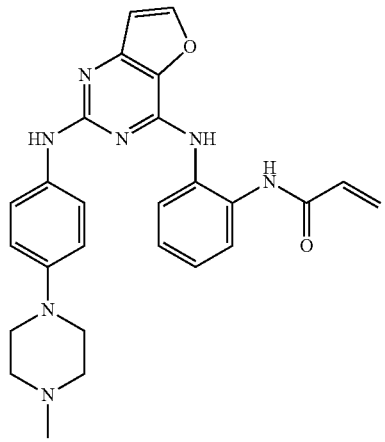 [SMILES: C=CC(=O)Nc1ccccc1Nc1nc(Nc2ccc(N3CCN(C)CC3)cc2)nc2ccsc12]

N-{2-[(2-{[4-(4-methylpiperazin-1-yl)phenyl]amino}furo[3,2-d]pyrimidin-4-yl)amino]phenyl}prop-2-enamide (12) was synthesized using the same synthetic route as used for (11). LC/MS: m/z calculated for [M+H]+470.22, found 469.88.

Synthesis of N-{2-[(6-amino-5-chloro-2-{[4-(4-methylpiperazin-1-yl)phenyl]amino}pyrimidin-4-yl)amino]phenyl}prop-2-enamide (13)

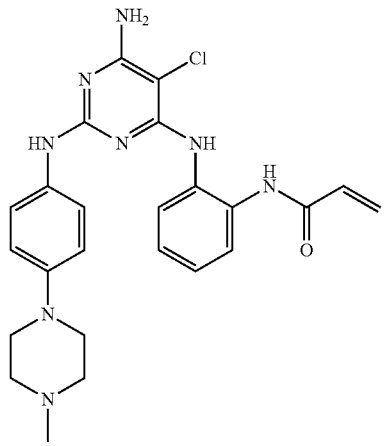 [SMILES: C=CC(=O)Nc1ccccc1Nc1nc(Nc2ccc(N3CCN(C)CC3)cc2)nc(N)c1Cl]

N-{2-[(6-amino-5-chloro-2-{[4-(4-methylpiperazin-1-yl)phenyl]amino}pyrimidin-4-yl)amino]phenyl}prop-2-enamide was synthesized using the same synthetic route as used for (1). LC/MS: m/z calculated for [M+H]+479.12, found 478.88.

Synthesis of N-{2-[(2-{[4-(4-methylpiperazin-1-yl)phenyl]amino}thieno[2,3-d]pyrimidin-4-yl)amino]phenyl}prop-2-enamide (14)

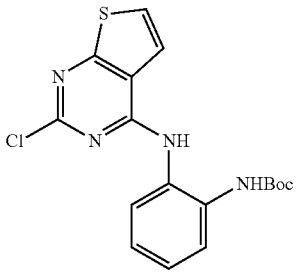 [SMILES: CC(C)(C)OC(=O)Nc1ccccc1Nc1nc(Cl)nc2sccc12]

tert-butyl (2-((2-chlorothieno[2,3-d]pyrimidin-4-yl)amino)phenyl)carbamate: 2,4-dichlorothieno[2,3-d]pyrimidine (205 mg, 1.0 mmol) and tert-butyl (2-aminophenyl)carbamate (208 mg, 1.0 mmol) were combined in isopropanol at room temperature and stirred for 2 days. The solvent was then evaporated, and the resulting residue purified by silica gel chromatography to provide the title compound (238 mg, 0.63 mmol, 63%). LC/MS: m/z calculated for [M+H]+377.08, found 377.39.

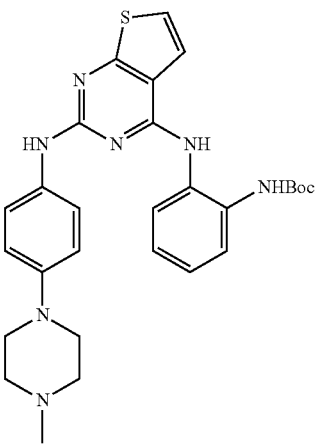 [SMILES: CN1CCN(c2ccc(Nc3nc(Nc4ccccc4NC(=O)OC(C)(C)C)c4ccsc4n3)cc2)CC1]

N4-(2-aminophenyl)-N2-(4-(4-methylpiperazin-1-yl)phenyl) thieno[2,3-d]pyrimidine-2,4-diamine: tert-butyl (2-((2-chlorothieno[2,3-d]pyrimidin-4-yl)amino)phenyl)carbamate (30 mg, 0.08 mmol), 4-(4-methylpiperazin-1-yl) aniline (23 mg, 0.12 mmol), $K_2CO_3$ (45 mg, 0.32 mmol), Brettphos (5 mg, 0.008 mmol) and Pd(Oac)$_2$ were combined in tert-butanol (1.5 mL). The mixture was degassed and stirred at 110° C. for 3 hours. Water was added and the aqueous mixture extracted with EtOAc. Combined extracts were washed with brine, dried with $Na_2SO_4$, concentrated and purified by silica gel chromatography to provide the title compound (40 mg, 0.075 mmol, 94%). LC/MS: m/z calculated for [M+H]+432.19, found 431.97.

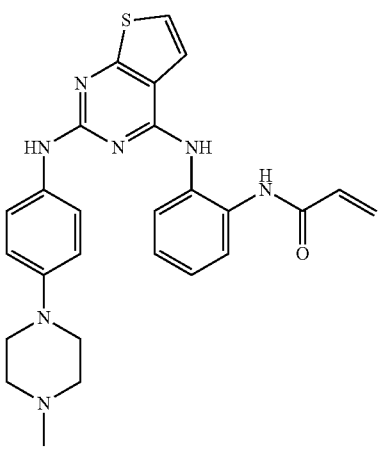 [SMILES: C=CC(=O)Nc1ccccc1Nc1nc(Nc2ccc(N3CCN(C)CC3)cc2)nc2sccc12]

N-{2-[(2-{[4-(4-methylpiperazin-1-yl)phenyl]amino}thieno[2,3-d]pyrimidin-4-yl)amino]phenyl}prop-2-enamide (14): N4-(2-aminophenyl)-N2-(4-(4-methylpiperazin-1-yl)phenyl)thieno[2,3-d]pyrimidine-2,4-diamine (40 mg, 0.075 mmol) was dissolved in a mixture of 1:1 DCM:TFA (2 mL) and stirred at rt for 2 hours. The solvent was then removed, and the unprotected aniline was transformed into the acrylamide by the General Procedure 3 (5.6 mg, 0.012 mmol, 15% over 2 steps). LC/MS: m/z calculated for [M+H]+ 486.20, found 485.88.

Synthesis of N-(2-((5-((4-methylbenzyl)oxy)-2-((4-(4-methylpiperazin-1-yl)phenyl)amino)pyrimidin-4-yl)amino)phenyl)acrylamide (15)

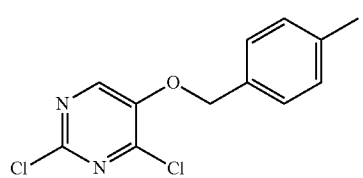 [SMILES: Cc1ccc(COc2cnc(Cl)nc2Cl)cc1]

2,4-dichloro-5-((4-methylbenzyl)oxy)pyrimidine: 2,4-dichloropyrimidin-5-ol (100 mg, 0.61 mmol) and 4-methylbenzylbromide (169 mg, 0.91 mmol) were dissolved in acetone. NaI (10 mg, 0.061 mmol) and $K_2CO_3$ (210 mg, 1.52 mmol) were added, and the reaction stirred at rt for 3 hours. Water was added and the mixture extracted with EtOAc. Combined extracts were washed with brine, dried with $Na_2SO_4$, concentrated and purified by silica gel chromatography to obtain the title compound (150 mg, 0.56, 92%). LC/MS: m/z calculated for [M+H]+269.02, found 269.17.

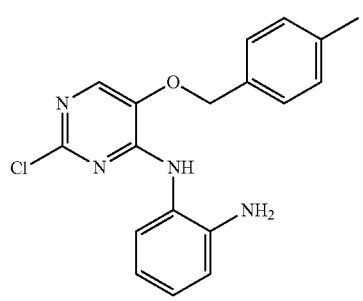 [SMILES: Cc1ccc(COc2cnc(Cl)nc2Nc2ccccc2N)cc1]

N1-(2-chloro-5-((4-methylbenzyl)oxy)pyrimidin-4-yl)benzene-1,2-diamine: 2,4-dichloro-5-((4-methylbenzyl)oxy)pyrimidine and 1,2-diaminobenzene were reacted according to General Procedure 1A. LC/MS: m/z calculated for [M+H]+341.11, found 341.27.

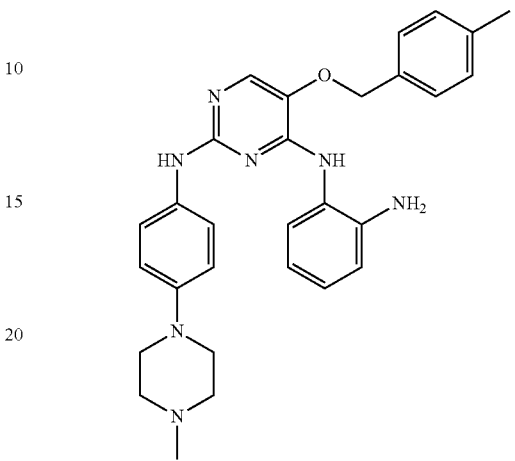

N4-(2-aminophenyl)-5-((4-methylbenzyl)oxy)-N2-(4-(4-methylpiperazin-1-yl)phenyl)pyrimidine-2,4-diamine: N1-(2-chloro-5-((4-methylbenzyl)oxy)pyrimidin-4-yl)benzene-1,2-diamine and 4-(4-methylpiperazin-1-yl) aniline were reacted and purified according to General Procedure 2. LC/MS: m/z calculated for [M+H]+496.27, found 496.48.

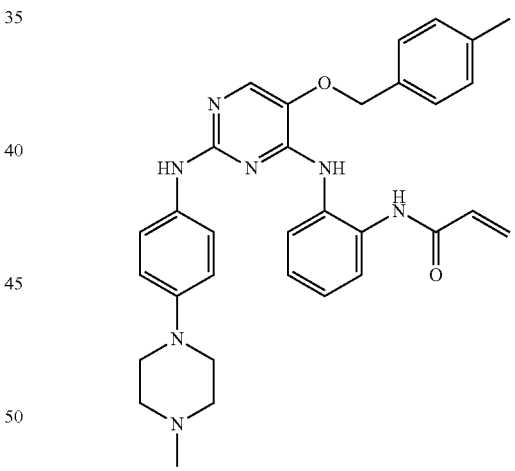

N-(2-((5-((4-methylbenzyl)oxy)-2-((4-(4-methylpiperazin-1-yl)phenyl)amino)pyrimidin-4-yl)amino)phenyl)acrylamide (15): The acrylamide was installed on N4-(2-aminophenyl)-5-((4-methylbenzyl)oxy)-N2-(4-(4-methylpiperazin-1-yl)phenyl)pyrimidine-2,4-diamine as described in General Procedure 3, and the products purified by HPLC to obtain the title compound. LC/MS: m/z calculated for [M+H]+550.29, found 550.29. $^1$H NMR (500 MHZ, DMSO-$d_6$) δ 10.24 (s, 1H), 9.81 (s, 2H), 9.24 (s, 1H), 7.88-7.66 (m, 1H), 7.39-7.32 (m, 2H), 7.31-7.24 (m, 2H), 7.24-7.19 (m, 1H), 7.18-7.12 (m, 3H), 7.06 (s, 1H), 6.96 (s, 1H), 6.85-6.77 (m, 2H), 6.42 (dd, J=17.0, 10.2 Hz, 1H), 6.16 (dd, J=17.0, 1.9 Hz, 1H), 5.74 (dd, J=10.2, 1.9 Hz, 1H), 5.05

(s, 2H), 3.73-3.62 (m, 2H), 3.51-3.39 (m, 2H), 3.15-3.04 (m, 2H), 2.88-2.76 (m, 5H), 2.26 (s, 3H).

Synthesis of N-(2-((2-((4-(4-methylpiperazin-1-yl)phenyl)amino)-5-((4-phenoxybenzyl)oxy)pyrimidin-4-yl)amino)phenyl)acrylamide (16)

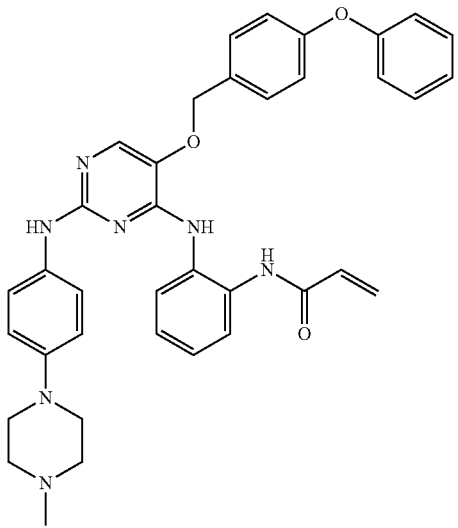 [SMILES: C=CC(=O)Nc1ccccc1Nc1nc(Nc2ccc(N3CCN(C)CC3)cc2)ncc1OCc1ccc(Oc2ccccc2)cc1]

N-(2-((2-((4-(4-methylpiperazin-1-yl)phenyl)amino)-5-((4-phenoxybenzyl)oxy)pyrimidin-4-yl)amino)phenyl)acrylamide (16) was synthesized using the same synthetic route as used for (15). LC/MS: m/z calculated for [M+H]+628.30, found 628.50. ¹H NMR (500 MHz, DMSO-d₆) δ 10.24 (s, 1H), 9.88 (s, 2H), 9.33 (s, 1H), 7.79-7.73 (m, 2H), 7.51-7.46 (m, 2H), 7.40-7.31 (m, 3H), 7.28 (ddd, J=11.2, 6.3, 2.4 Hz, 3H), 7.22 (td, J=7.6, 1.6 Hz, 1H), 7.11 (t, J=7.5 Hz, 1H), 7.02-6.93 (m, 4H), 6.86-6.79 (m, 2H), 6.41 (dd, J=16.9, 10.2 Hz, 1H), 6.12 (dd, J=17.0, 1.9 Hz, 1H), 5.68 (dd, J=10.1, 2.0 Hz, 1H), 5.08 (s, 2H), 3.71-3.64 (m, 2H), 3.45 (d, J=12.0 Hz, 2H), 3.09 (s, 2H), 2.85 (d, J=12.5 Hz, 2H), 2.80 (s, 3H).

Synthesis of N-(2-((5-((2-chloro-6-methylbenzyl)oxy)-2-((4-(4-methylpiperazin-1-yl)phenyl)amino)pyrimidin-4-yl)amino)phenyl)acrylamide (17)

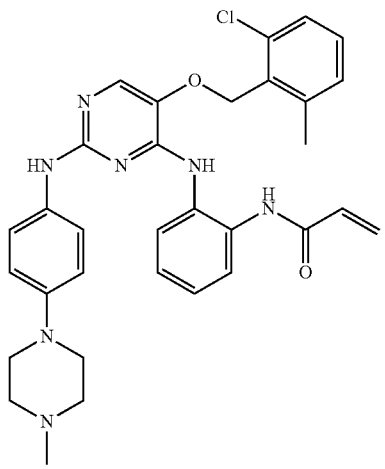 [SMILES: C=CC(=O)Nc1ccccc1Nc1nc(Nc2ccc(N3CCN(C)CC3)cc2)ncc1OCc1c(C)cccc1Cl]

N-(2-((5-((2-chloro-6-methylbenzyl)oxy)-2-((4-(4-methylpiperazin-1-yl)phenyl)amino)pyrimidin-4-yl)amino)phenyl)acrylamide (17) was synthesized using the same synthetic route as used for (15). LC/MS: m/z calculated for [M+H]+584.25, found 583.89. ¹H NMR (500 MHz, DMSO-d₆) δ 10.14 (s, 1H), 9.96 (s, 1H), 9.77 (s, 1H), 9.17 (s, 1H), 7.82 (s, 1H), 7.78 (d, J=8.0 Hz, 1H), 7.33-7.25 (m, 5H), 7.25 (d, J=7.8 Hz, 1H), 7.23-7.14 (m, 2H), 6.84 (d, J=8.7 Hz, 2H), 6.28 (dd, J=17.0, 10.2 Hz, 1H), 5.81 (dd, J=16.9, 1.9 Hz, 1H), 5.60 (dd, J=10.1, 1.9 Hz, 1H), 5.17 (s, 2H), 3.68 (d, J=13.1 Hz, 2H), 3.46 (d, J=12.2 Hz, 2H), 3.10 (s, 2H), 2.84 (d, J=12.8 Hz, 2H), 2.80 (s, 3H), 2.34 (s, 3H).

Synthesis of 4-((2-acrylamidophenyl)amino)-N-(2-chloro-6-methylphenyl)-2-((4-(4-methylpiperazin-1-yl)phenyl)amino)pyrimidine-5-carboxamide (18)

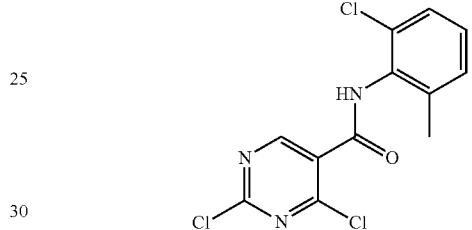

2,4-dichloro-N-(2-chloro-6-methylphenyl)pyrimidine-5-carboxamide: 2,4-dichloropyrimidine-5-carbonyl chloride (100 mg, 0.47 mmol) was dissolved in THF (1 mL). At rt, a solution of 2-chloro-6-methylaniline (67 mg, 0.47 mmol) in THF (1 mL) was then added and a white precipitate quickly formed. The mixture was stirred overnight before the solvent was removed and the crude solid purified by silica gel chromatography to obtain the title compound as a white solid (119 mg, 0.38 mmol, 80%). LC/MS: m/z calculated for [M+H]+315.97, found 316.07.

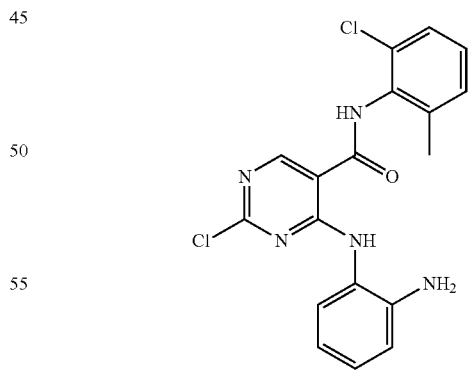

4-((2-aminophenyl)amino)-2-chloro-N-(2-chloro-6-methylphenyl)pyrimidine-5-carboxamide: 2,4-dichloro-N-(2-chloro-6-methylphenyl)pyrimidine-5-carboxamide and 1,2-diaminobenzene were reacted according to General Procedure 1B, and the products purified by silica gel chromatography to afford the title compound. LC/MS: m/z calculated for [M+H]+388.07, found 388.27.

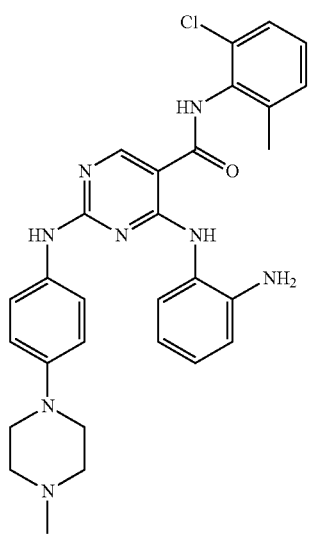 [SMILES: Cc1cccc(Cl)c1NC(=O)c1cnc(Nc2ccc(N3CCN(C)CC3)cc2)nc1Nc1ccccc1N]

4-((2-aminophenyl)amino)-N-(2-chloro-6-methylphenyl)-2-((4-(4-methylpiperazin-1-yl)phenyl)amino)pyrimidine-5-carboxamide: 4-((2-aminophenyl)amino)-2-chloro-N-(2-chloro-6-methylphenyl)pyrimidine-5-carboxamide and 4-(4-methylpiperazin-1-yl) aniline were reacted as described in General Procedure 2. LC/MS: m/z calculated for [M+H]+543.23, found 543.29.

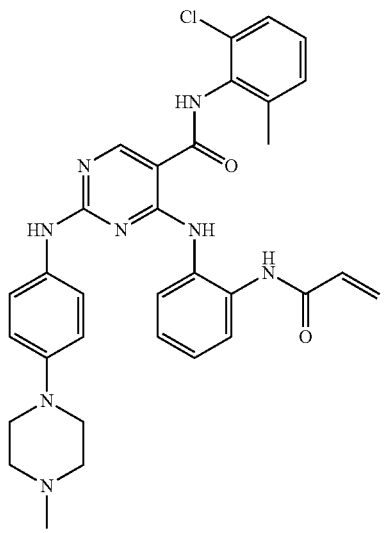 [SMILES: C=CC(=O)Nc1ccccc1Nc1nc(Nc2ccc(N3CCN(C)CC3)cc2)ncc1C(=O)Nc1c(C)cccc1Cl]

4-((2-acrylamidophenyl)amino)-N-(2-chloro-6-methylphenyl)-2-((4-(4-methylpiperazin-1-yl)phenyl)amino)pyrimidine-5-carboxamide (18): The acrylamide was installed upon 4-((2-aminophenyl)amino)-N-(2-chloro-6-methylphenyl)-2-((4-(4-methylpiperazin-1-yl)phenyl)amino)pyrimidine-5-carboxamide using the General Procedure 3. LC/MS: m/z calculated for [M+H]+597.24, found 597.39. $^1$H NMR (500 MHZ, DMSO-$d_6$) δ 10.75 (s, 1H), 9.83 (s, 1H), 9.69 (s, 3H), 8.82 (s, 1H), 8.04 (s, 1H), 7.46 (d, J=8.3 Hz, 2H), 7.36-7.26 (m, 2H), 7.26-7.16 (m, 3H), 7.09 (t, J=7.5 Hz, 1H), 6.83 (d, J=8.5 Hz, 2H), 6.27 (dd, J=17.1, 10.3 Hz, 1H), 6.06 (dd, J=17.1, 2.0 Hz, 1H), 5.56 (dd, J=10.2, 2.0 Hz, 1H), 3.68 (d, J=13.1 Hz, 2H), 3.46 (d, J=12.2 Hz, 2H), 3.11 (d, J=11.2 Hz, 2H), 2.82-2.77 (m, 5H), 2.16 (s, 3H).

Synthesis of 2-{[4-(4-methylpiperazin-1-yl)phenyl]amino}-N-[(4-phenoxyphenyl)methyl]-4-{[2-(prop-2-enamido)phenyl]amino}pyrimidine-5-carboxamide (19)

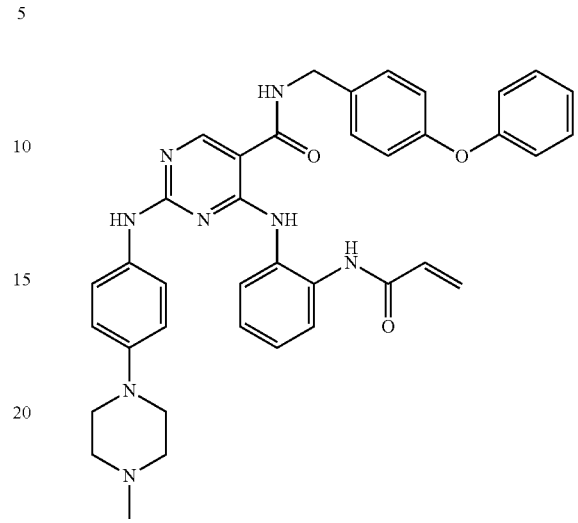

2-{[4-(4-methylpiperazin-1-yl)phenyl]amino}-N-[(4-phenoxyphenyl)methyl]-4-{[2-(prop-2-enamido)phenyl]amino}pyrimidine-5-carboxamide (19) was synthesized using the same route as described for (18). LC/MS: m/z calculated for [M+H]+655.31, found 655.6.

Synthesis of 4-((2-acrylamidophenyl)amino)-2-((4-(4-methylpiperazin-1-yl)phenyl)amino)-N-(4-phenoxyphenyl)pyrimidine-5-carboxamide (20)

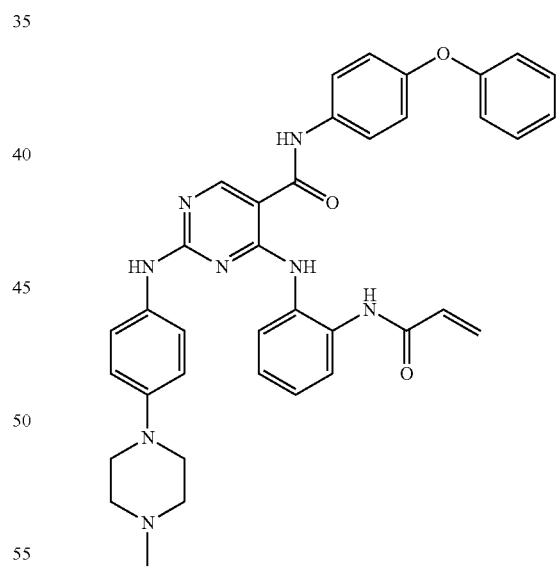

4-((2-acrylamidophenyl)amino)-2-((4-(4-methylpiperazin-1-yl)phenyl)amino)-N-(4-phenoxyphenyl)pyrimidine-5-carboxamide (20) was synthesized using the same route as described for (18). LC/MS: m/z calculated for [M+H]+ 641.29, found 641.50. $^1$H NMR (500 MHZ, DMSO-$d_6$) δ 10.89 (s, 1H), 10.12 (s, 1H), 9.81 (s, 1H), 9.61 (brs, 2H), 8.82 (s, 1H), 7.78-7.65 (m, 2H), 7.62-7.49 (m, 2H), 7.47-7.36 (m, 3H), 7.27 (t, J=7.8 Hz, 1H), 7.21-7.08 (m, 2H), 7.08-6.96 (m, 4H), 6.91 (d, J=8.4 Hz, 2H), 6.48 (dd, J=17.1, 10.2 Hz, 1H), 6.22 (dd, J=17.2, 2.0 Hz, 1H), 5.77-5.71 (m, 1H), 3.80-3.73 (m, 2H), 3.59-3.51 (m, 2H), 3.25-3.12 (m, 2H), 2.96-2.85 (m, 5H).

Synthesis of 4-((2-acrylamidophenyl)amino)-N-(2,4-dichloro-6-methylphenyl)-2-((4-(4-methylpiperazin-1-yl)phenyl)amino)pyrimidine-5-carboxamide (21)

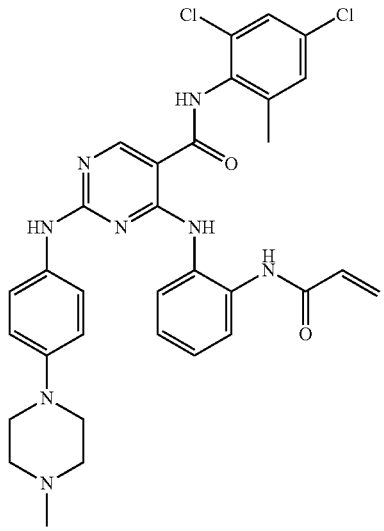 [SMILES: C=CC(=O)Nc1ccccc1Nc1nc(Nc2ccc(N3CCN(C)CC3)cc2)ncc1C(=O)Nc1c(C)cc(Cl)cc1Cl]

4-((2-acrylamidophenyl)amino)-N-(2,4-dichloro-6-methylphenyl)-2-((4-(4-methylpiperazin-1-yl)phenyl)amino)pyrimidine-5-carboxamide (21) was synthesized using the same route as described for (18). LC/MS: m/z calculated for [M+H]+611.26, found 610.79. $^1$H NMR (500 MHZ, DMSO-$d_6$) § 10.69 (s, 1H), 9.85 (s, 1H), 9.70 (s, 1H), 9.65 (s, 2H), 8.82 (s, 1H), 8.00 (s, 1H), 7.51 (dd, J=9.8, 2.4 Hz, 1H), 7.45 (s, 2H), 7.37 (dd, J=11.0, 2.4 Hz, 1H), 7.29 (d, J=7.8 Hz, 1H), 7.20 (d, J=7.6 Hz, 1H), 7.09 (t, J=7.6 Hz, 1H), 6.83 (d, J=8.5 Hz, 2H), 6.28 (dd, J=17.1, 10.3 Hz, 1H), 6.06 (dd, J=17.1, 2.0 Hz, 1H), 5.57 (dd, J=10.2, 2.0 Hz, 1H), 3.68 (d, J=13.2 Hz, 2H), 3.46 (d, J=12.0 Hz, 2H), 3.11 (d, J=12.8 Hz, 2H), 2.85 (d, J=12.6 Hz, 2H), 2.80 (s, 3H), 2.16 (s, 3H).

Synthesis of 4-((2-acrylamidophenyl)amino)-N-(2-chloro-4,6-dimethylphenyl)-2-((4-(4-methylpiperazin-1-yl)phenyl)amino)pyrimidine-5-carboxamide (22)

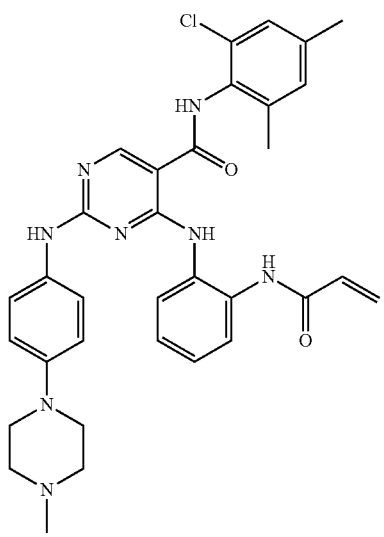 [SMILES: C=CC(=O)Nc1ccccc1Nc1nc(Nc2ccc(N3CCN(C)CC3)cc2)ncc1C(=O)Nc1c(C)cc(C)cc1Cl]

4-((2-acrylamidophenyl)amino)-N-(2-chloro-4,6-dimethylphenyl)-2-((4-(4-methylpiperazin-1-yl)phenyl)amino)pyrimidine-5-carboxamide (22) was synthesized using the same route as described for (18). LC/MS: m/z calculated for [M+H]+631.20, found 630.70. $^1$H NMR (500 MHZ, DMSO-$d_6$) δ 10.78 (s, 1H), 9.75 (s, 1H), 9.69 (s, 3H), 8.82 (s, 1H), 8.00 (s, 1H), 7.48-7.41 (m, 2H), 7.29 (d, J=7.9 Hz, 1H), 7.23-7.13 (m, 2H), 7.09 (t, J=7.7 Hz, 1H), 7.04 (d, J=11.2 Hz, 1H), 6.83 (d, J=8.5 Hz, 2H), 6.28 (dd, J=17.1, 10.2 Hz, 1H), 6.06 (dd, J=17.1, 1.9 Hz, 1H), 5.57 (dd, J=10.2, 2.0 Hz, 1H), 3.68 (d, J=13.3 Hz, 2H), 3.46 (d, J=12.0 Hz, 2H), 3.11 (d, J=10.8 Hz, 2H), 2.88-2.78 (m, 5H), 2.23 (d, J=3.3 Hz, 3H), 2.11 (s, 3H).

Synthesis of 4-((2-acrylamidophenyl)amino)-N-(4,5-dimethoxy-2-methylphenyl)-2-((4-(4-methylpiperazin-1-yl)phenyl)amino)pyrimidine-5-carboxamide (23)

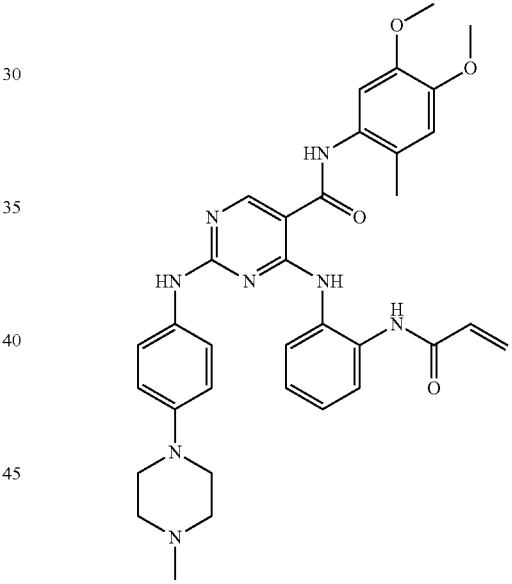

4-((2-acrylamidophenyl)amino)-N-(4,5-dimethoxy-2-methylphenyl)-2-((4-(4-methylpiperazin-1-yl)phenyl)amino)pyrimidine-5-carboxamide (23) was synthesized using the same route as described for (18). LC/MS: m/z calculated for [M+H]+623.30, found 622.99. $^1$H NMR (500 MHz, DMSO-$d_6$) δ 10.92 (s, 1H), 9.73 (s, 1H), 9.69 (s, 1H), 9.60 (s, 1H), 9.56 (s, 1H), 8.76 (s, 1H), 8.02 (s, 1H), 7.47 (s, 2H), 7.32 (d, J=7.9 Hz, 1H), 7.19 (t, J=7.5 Hz, 1H), 7.07 (t, J=7.5 Hz, 1H), 6.86-6.80 (m, 3H), 6.78 (s, 1H), 6.34 (dd, J=17.1, 10.3 Hz, 1H), 6.10 (dd, J=17.1, 2.0 Hz, 1H), 5.59 (dd, J=10.3, 2.0 Hz, 1H), 3.69 (s, 3H), 3.67 (s, 2H), 3.65 (s, 3H), 3.46 (d, J=12.1 Hz, 2H), 3.11 (d, J=10.6 Hz, 2H), 2.85 (d, J=12.6 Hz, 2H), 2.80 (d, J=2.9 Hz, 3H), 2.08 (s, 3H).

Synthesis of 4-((2-acrylamidophenyl)amino)-N-(2-chloro-4-cyano-6-methylphenyl)-2-((4-(4-methylpiperazin-1-yl)phenyl)amino)pyrimidine-5-carboxamide (24)

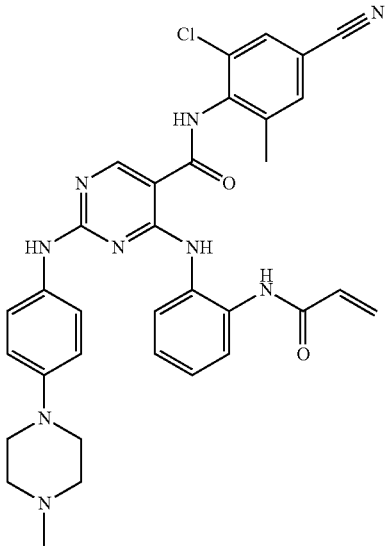 [SMILES: C=CC(=O)Nc1ccccc1Nc1nc(Nc2ccc(N3CCN(C)CC3)cc2)ncc1C(=O)Nc1c(C)cc(C#N)cc1Cl]

4-((2-acrylamidophenyl)amino)-N-(2-chloro-4-cyano-6-methylphenyl)-2-((4-(4-methylpiperazin-1-yl)phenyl)amino)pyrimidine-5-carboxamide (24) was synthesized using the same route as described for (18). LC/MS: m/z calculated for [M+H]+622.24, found 621.89. $^1$H NMR (500 MHz, DMSO-$d_6$) § 10.61 (s, 1H), 10.05 (s, 1H), 9.70 (s, 1H), 9.68 (s, 2H), 8.82 (s, 1H), 7.96 (s, 2H), 7.76 (s, 1H), 7.48-7.43 (m, 2H), 7.29 (d, J=7.9 Hz, 1H), 7.20 (t, J=7.5 Hz, 1H), 7.10 (t, J=7.6 Hz, 1H), 6.82 (d, J=8.1 Hz, 2H), 6.27 (dd, J=17.1, 10.3 Hz, 1H), 6.05 (dd, J=17.1, 2.0 Hz, 1H), 5.57 (dd, J=10.2, 2.0 Hz, 1H), 3.68 (d, J=13.2 Hz, 2H), 3.46 (d, J=12.0 Hz, 2H), 3.11 (q, J=11.0 Hz, 2H), 2.88-2.78 (m, 5H), 2.21 (s, 3H).

Synthesis of 4-((2-acrylamidophenyl)amino)-N-(3-chloro-5-methylphenyl)-2-((4-(4-methylpiperazin-1-yl)phenyl)amino)pyrimidine-5-carboxamide (25)

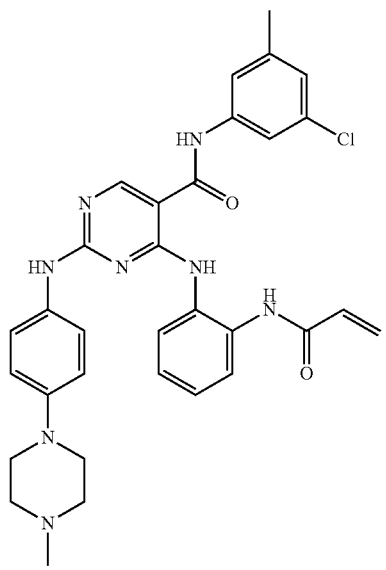 [SMILES: C=CC(=O)Nc1ccccc1Nc1nc(Nc2ccc(N3CCN(C)CC3)cc2)ncc1C(=O)Nc1cc(C)cc(Cl)c1]

4-((2-acrylamidophenyl)amino)-N-(3-chloro-5-methylphenyl)-2-((4-(4-methylpiperazin-1-yl)phenyl)amino)pyrimidine-5-carboxamide (25) was synthesized using the same route as described for (18). LC/MS: m/z calculated for [M+H]+597.24, found 596.89. $^1$H NMR (500 MHz, DMSO-$d_6$) δ 10.86 (s, 1H), 10.08 (s, 1H), 9.78 (s, 1H), 9.68 (s, 2H), 8.75 (s, 1H), 8.12 (s, 1H), 7.68-7.62 (m, 1H), 7.47-7.43 (m, 2H), 7.39 (s, 1H), 7.31 (d, J=7.9 Hz, 1H), 7.20 (t, J=7.8 Hz, 1H), 7.08 (t, J=7.7 Hz, 1H), 6.94 (s, 1H), 6.86 (d, J=8.5 Hz, 2H), 6.44 (dd, J=17.1, 10.3 Hz, 1H), 6.18 (dd, J=17.1, 2.0 Hz, 1H), 5.68 (dd, J=10.2, 2.0 Hz, 1H), 3.70 (d, J=13.0 Hz, 2H), 3.47 (d, J=12.0 Hz, 2H), 3.10 (t, J=10.9 Hz, 2H), 2.86 (d, J=12.7 Hz, 2H), 2.81 (s, 3H), 2.24 (s, 3H).

Synthesis of 4-((2-acrylamidophenyl)amino)-N-(2-ethylphenyl)-2-((4-(4-methylpiperazin-1-yl)phenyl)amino)pyrimidine-5-carboxamide (26)

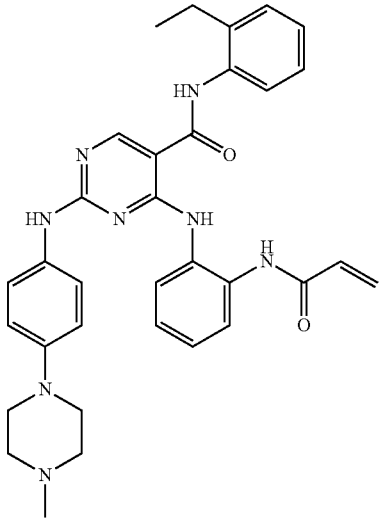 [SMILES: C=CC(=O)Nc1ccccc1Nc1nc(Nc2ccc(N3CCN(C)CC3)cc2)ncc1C(=O)Nc1ccccc1CC]

4-((2-acrylamidophenyl)amino)-N-(2-ethylphenyl)-2-((4-(4-methylpiperazin-1-yl)phenyl)amino)pyrimidine-5-carboxamide (26) was synthesized using the same route as described for (18). LC/MS: m/z calculated for [M+H]+ 577.30, found 576.89. $^1$H NMR (500 MHz, DMSO-$d_6$) δ 10.87 (s, 1H), 9.73 (s, 1H), 9.72 (s, 1H), 9.70 (s, 1H), 9.61 (s, 1H), 8.76 (s, 1H), 8.05 (s, 1H), 7.46 (d, J=8.8 Hz, 2H), 7.31 (d, J=8.0 Hz, 1H), 7.27-7.21 (m, 1H), 7.23-7.12 (m, 4H), 7.08 (t, J=7.7 Hz, 1H), 6.84 (d, J=8.6 Hz, 2H), 6.31 (dd, J=17.1, 10.3 Hz, 1H), 6.08 (dd, J=17.1, 2.0 Hz, 1H), 5.59 (dd, J=10.2, 2.0 Hz, 1H), 3.69 (d, J=13.2 Hz, 2H), 3.46 (d, J=12.0 Hz, 2H), 3.11 (d, J=11.1 Hz, 2H), 2.85 (d, J=12.6 Hz, 2H), 2.80 (d, J=2.9 Hz, 3H), 2.55 (q, J=7.5 Hz, 2H), 1.07 (t, J=7.5 Hz, 3H).

Synthesis of N-(2,6-dichlorophenyl)-2-{[4-(4-methylpiperazin-1-yl)phenyl]amino}-4-{[2-(prop-2-enamido)phenyl]amino}pyrimidine-5-carboxamide (27)

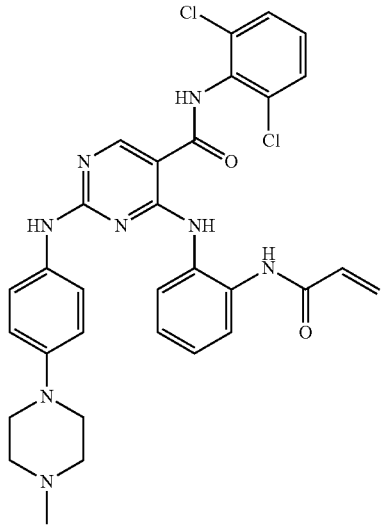 [SMILES: C=CC(=O)Nc1ccccc1Nc1nc(Nc2ccc(N3CCN(C)CC3)cc2)ncc1C(=O)Nc1c(Cl)cccc1Cl]

N-(2,6-dichlorophenyl)-2-{[4-(4-methylpiperazin-1-yl)phenyl]amino}-4-{[2-(prop-2-enamido)phenyl]amino}pyrimidine-5-carboxamide (27) was synthesized using the same route as described for (18). LC/MS: m/z calculated for [M+H]+617.19, found 616.79.

Synthesis of N-(2,6-dimethylphenyl)-2-{[4-(4-methylpiperazin-1-yl)phenyl]amino}-4-{[2-(prop-2-enamido)phenyl]amino}pyrimidine-5-carboxamide (28)

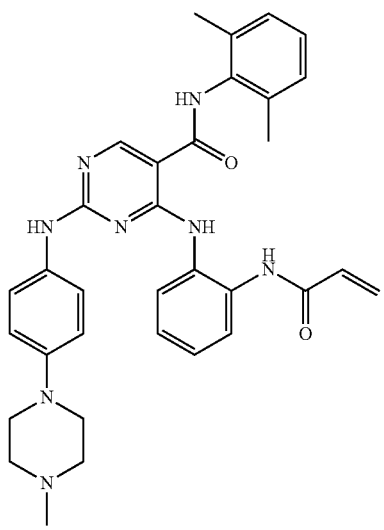 [SMILES: C=CC(=O)Nc1ccccc1Nc1nc(Nc2ccc(N3CCN(C)CC3)cc2)ncc1C(=O)Nc1c(C)cccc1C]

N-(2,6-dimethylphenyl)-2-{[4-(4-methylpiperazin-1-yl)phenyl]amino}-4-{[2-(prop-2-enamido)phenyl]amino}pyrimidine-5-carboxamide (28) was synthesized using the same route as described for (18). LC/MS: m/z calculated for [M+H]+577.30, found 576.99.

Synthesis of 4-((2-acrylamidophenyl)amino)-N-(2,6-dichloro-3,5-dimethoxyphenyl)-2-((4-(4-methylpiperazin-1-yl)phenyl)amino)pyrimidine-5-carboxamide (29)

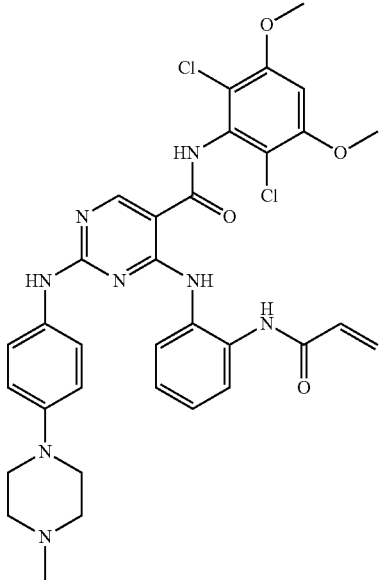 [SMILES: C=CC(=O)Nc1ccccc1Nc1nc(Nc2ccc(N3CCN(C)CC3)cc2)ncc1C(=O)Nc1c(Cl)c(OC)cc(OC)c1Cl]

4-((2-acrylamidophenyl)amino)-N-(2,6-dichloro-3,5-dimethoxyphenyl)-2-((4-(4-methylpiperazin-1-yl)phenyl)amino)pyrimidine-5-carboxamide (29) was synthesized using the same route as described for (18). LC/MS: m/z calculated for [M+H]+677.21, found 676.8. $^1$H NMR (500 MHZ, DMSO-d$_6$) δ 10.59 (s, 1H), 10.01 (s, 1H), 9.67 (s, 3H), 8.81 (s, 1H), 7.93 (s, 1H), 7.44 (d, J=8.5 Hz, 2H), 7.31 (d, J=7.9 Hz, 1H), 7.20 (t, J=7.8 Hz, 1H), 7.10 (t, J=7.6 Hz, 1H), 6.88 (s, 1H), 6.83-6.78 (m, 2H), 6.27 (dd, J=17.1, 10.2 Hz, 1H), 6.05 (dd, J=17.1, 1.9 Hz, 1H), 5.55 (dd, J=10.2, 2.0 Hz, 1H), 3.89 (s, 6H), 3.68 (d, J=13.2 Hz, 2H), 3.46 (d, J=12.1 Hz, 2H), 3.16-3.05 (m, 2H), 2.84 (d, J=12.3 Hz, 2H), 2.80 (s, 3H).

Synthesis of 3-chloro-5-methyl-4-(2-{[4-(4-methylpiperazin-1-yl)phenyl]amino}-4-{[2-(prop-2-enamido)phenyl]amino}pyrimidine-5-amido)benzoic acid (30)

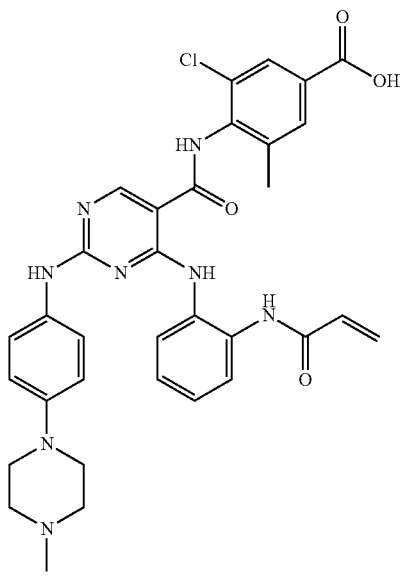 [SMILES: C=CC(=O)Nc1ccccc1Nc1nc(Nc2ccc(N3CCN(C)CC3)cc2)ncc1C(=O)Nc1c(C)cc(C(=O)O)cc1Cl]

3-chloro-5-methyl-4-(2-{[4-(4-methylpiperazin-1-yl)phenyl]amino}-4-{[2-(prop-2-enamido)phenyl]amino}pyrimidine-5-amido)benzoic acid (30) was synthesized using the same route as described for (18). LC/MS: m/z calculated for [M+H]+641.23, found 640.90.

Synthesis of N-{2-[(5-chloro-2-{[4-(4-methylpiperazin-1-yl)phenyl]amino}pyrimidin-4-yl)amino]-3-methylphenyl}prop-2-enamide (31)

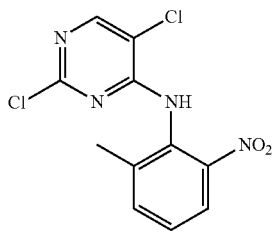 [SMILES: Cc1cccc([N+](=O)[O-])c1Nc1nc(Cl)ncc1Cl]

2,5-dichloro-N-(2-methyl-6-nitrophenyl)pyrimidin-4-amine: NaH (44 mg, 1.1 mmol, 60%) was added to a solution of 2-methyl-6-nitroaniline in DMF at 0° C., and the mixture was stirred for 30 minutes. 2,4,5-trichloropyrimidine was then added to the mixture at 0° C. After 5 hours, the reaction was quenched with water and the aqueous mixture extracted with EtOAc. Combined extracts were washed with brine, dried with Na₂SO₄, concentrated and purified by silica gel chromatography to afford the title compound (110 mg, 0.37 mmol, 37%). LC/MS: m/z calculated for [M+H]+299.00, found 299.17.

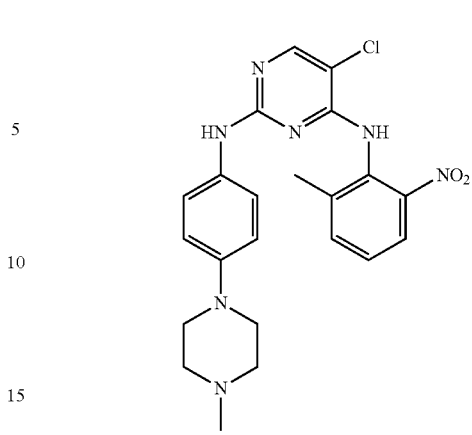

5-chloro-N4-(2-methyl-6-nitrophenyl)-N2-(4-(4-methylpiperazin-1-yl)phenyl)pyrimidine-2,4-diamine: 2,5-dichloro-N-(2-methyl-6-nitrophenyl)pyrimidin-4-amine was reacted with 4-(4-methylpiperazin-1-yl) aniline as per General Procedure 2 (97%). LC/MS: m/z calculated for [M+H]+ 454.17, found 454.27.

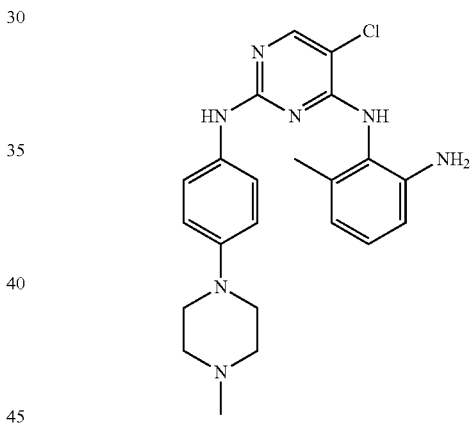

N4-(2-amino-6-methylphenyl)-5-chloro-N2-(4-(4-methylpiperazin-1-yl)phenyl)pyrimidine-2,4-diamine: 5-chloro-N4-(2-methyl-6-nitrophenyl)-N2-(4-(4-methylpiperazin-1-yl)phenyl)pyrimidine-2,4-diamine (163 mg, 0.36 mmol) was dissolved in EtOH (5 mL). NH₄Cl (154 mg, 2.88 mmol) dissolved in water (1 mL) was then added, and the mixture heated to 60° C. Then, Fe (80 mg, 1.44 mmol) was added and the reaction heated to 80° C. for 4 hours. The reaction mixture was then filtered, diluted with water, basified with NaHCO₃, and extracted with EtOAc. Combined extracts were washed with brine, dried with Na₂SO₄, concentrated and purified by silica gel chromatography to provide the title compound (50 mg, 0.12 mmol, 33%). LC/MS: m/z calculated for [M+H]+424.19, found 424.29.

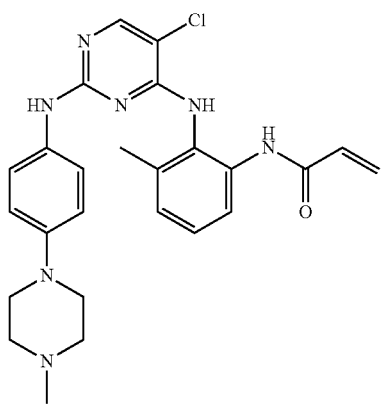 [SMILES: C=CC(=O)Nc1cccc(C)c1Nc1nc(Nc2ccc(N3CCN(C)CC3)cc2)ncc1Cl]

N-{2-[(5-chloro-2-{[4-(4-methylpiperazin-1-yl)phenyl]amino}pyrimidin-4-yl)amino]-3-methylphenyl}prop-2-enamide (31): The acrylamide was installed on N4-(2-amino-6-methylphenyl)-5-chloro-N2-(4-(4-methylpiperazin-1-yl)phenyl)pyrimidine-2,4-diamine as described in General Procedure 3 (15 mg, 0.025 mmol, 21%). LC/MS: m/z calculated for [M+H]+478.20, found 478.38.

Synthesis of N-{2-[(5-chloro-2-{[4-(4-methylpiperazin-1-yl)phenyl]amino}pyrimidin-4-yl)amino]-4-methylphenyl}prop-2-enamide (32)

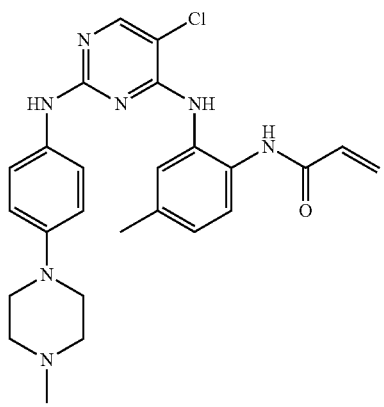 [SMILES: C=CC(=O)Nc1ccc(C)cc1Nc1nc(Nc2ccc(N3CCN(C)CC3)cc2)ncc1Cl]

N-{2-[(5-chloro-2-{[4-(4-methylpiperazin-1-yl)phenyl]amino}pyrimidin-4-yl)amino]-4-methylphenyl}prop-2-enamide (32) was synthesized using the same route as described for (31). LC/MS: m/z calculated for [M+H]+478.20, found 477.98.

Synthesis of N-{2-[(5-chloro-2-{[4-(4-methylpiperazin-1-yl)phenyl]amino}pyrimidin-4-yl)amino]-5-methylphenyl}prop-2-enamide (33)

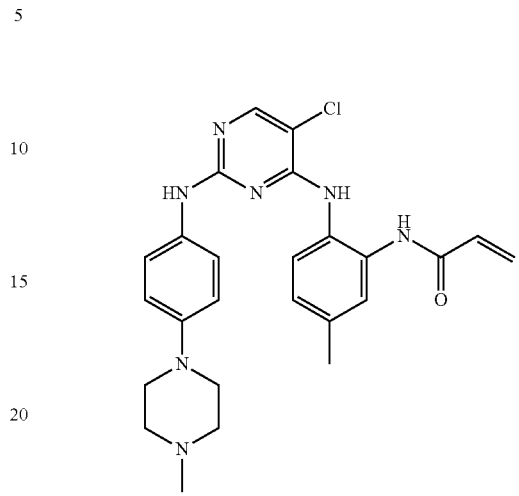

N-{2-[(5-chloro-2-{[4-(4-methylpiperazin-1-yl)phenyl]amino}pyrimidin-4-yl)amino]-5-methylphenyl}prop-2-enamide (33) was synthesized using the same route as described for (31). LC/MS: m/z calculated for [M+H]+478.20, found 478.08.

Synthesis of N-{2-[(5-chloro-2-{[4-(4-methylpiperazin-1-yl)phenyl]amino}pyrimidin-4-yl)amino]-6-methylphenyl}prop-2-enamide (34)

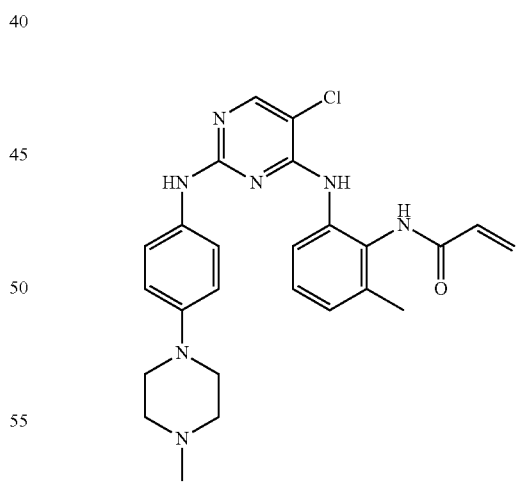

N-{2-[(5-chloro-2-{[4-(4-methylpiperazin-1-yl)phenyl]amino}pyrimidin-4-yl)amino]-6-methylphenyl}prop-2-enamide (34) was synthesized using the same route as described for (31). LC/MS: m/z calculated for [M+H]+478.20, found 477.88.

Synthesis of N-(2-chloro-6-methylphenyl)-4-{[5-methyl-2-(prop-2-enamido)phenyl]amino}-2-{[4-(4-methylpiperazin-1-yl)phenyl]amino}pyrimidine-5-carboxamide (35)

N-(4-methyl-2-nitrophenyl)acrylamide: 4-methyl-2-nitroaniline (152 mg, 1.0 mmol) was dissolved in CH$_3$CN (3 mL) and treated with DIEA (258 mg, 2.0 mmol). Acryloyl chloride (80.8 µL, 1.0 mmol) was then added at 0° C., and the reaction stirred for 20 minutes. Then the solvent was removed and the crude residue carried forward without purification. LC/MS: m/z calculated for [M+H]+207.07, found 207.39.

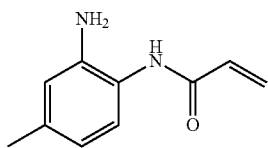

N-(2-amino-4-methylphenyl)acrylamide: N-(4-methyl-2-nitrophenyl)acrylamide (1.0 mmol) was dissolved in ethanol (5 mL) and NH$_4$Cl (428 mmol, 8.0 mmol) in water (1 mL) was added, and the solution heated to 60° C. Fe (222 mg, 4.0 mmol) was then added and the reaction stirred at 80° C. for 4 hours. Water was then added and the aqueous mixture extracted with EtOAc. Combined extracts were washed with brine, dried with Na$_2$SO$_4$, and concentrated to provide the title compound. LC/MS: m/z calculated for [M+H]+177.09, found 176.89.

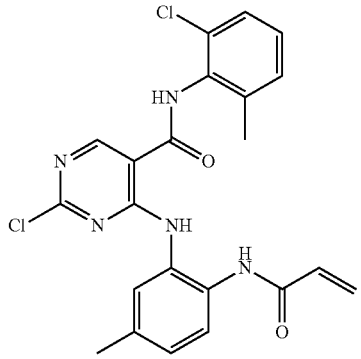 [SMILES: C=CC(=O)Nc1ccc(C)cc1Nc1nc(Cl)ncc1C(=O)Nc1c(C)cccc1Cl]

4-((2-acrylamido-5-methylphenyl)amino)-2-chloro-N-(2-chloro-6-methylphenyl)pyrimidine-5-carboxamide: N-(2-amino-4-methylphenyl)acrylamide (30 mg, 0.17 mmol), DIEA (44 mg, 0.34 mmol) and 2,4-dichloro-N-(2-chloro-6-methylphenyl)pyrimidine-5-carboxamide (54 mg, 0.17 mmol) were dissolved in n-butanol (1 mL) and stirred at room temperature overnight. The solvent was then evaporated and the residue purified by HPLC to afford the title compound. LC/MS: m/z calculated for [M+H]+456.09, found 455.80.

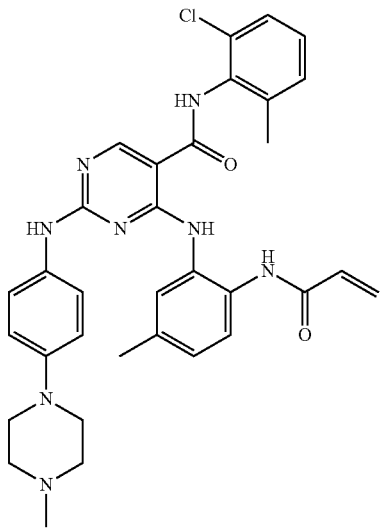 [SMILES: C=CC(=O)Nc1ccc(C)cc1Nc1nc(Nc2ccc(N3CCN(C)CC3)cc2)ncc1C(=O)Nc1c(C)cccc1Cl]

N-(2-chloro-6-methylphenyl)-4-{[5-methyl-2-(prop-2-enamido)phenyl]amino}-2-{[4-(4-methylpiperazin-1-yl)phenyl]amino}pyrimidine-5-carboxamide (35): 4-((2-acrylamido-5-methylphenyl)amino)-2-chloro-N-(2-chloro-6-methylphenyl)pyrimidine-5-carboxamide and 4-(4-methylpiperazin-1-yl) aniline were reacted as described in General Procedure 2, and purified by HPLC to obtain the title compound. LC/MS: m/z calculated for [M+H]+611.26, found 610.89.

Synthesis of N-(2-chloro-6-methylphenyl)-4-{[2-methyl-6-(prop-2-enamido)phenyl]amino}-2-{[4-(4-methylpiperazin-1-yl)phenyl]amino}pyrimidine-5-carboxamide (36)

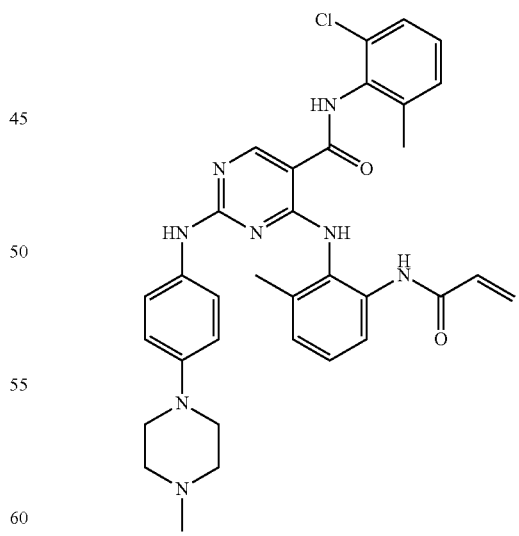

N-(2-chloro-6-methylphenyl)-4-{[2-methyl-6-(prop-2-enamido)phenyl]amino}-2-{[4-(4-methylpiperazin-1-yl)phenyl]amino}pyrimidine-5-carboxamide (36) was synthesized using the same route as described for (35). LC/MS: m/z calculated for [M+H]+611.26, found 611.49.

101

Synthesis of N-(2-chloro-6-methylphenyl)-2-{[4-(4-methylpiperazin-1-yl)phenyl]amino}-4-{[2-(prop-2-enamido)-5-(propan-2-yl)phenyl]amino}pyrimidine-5-carboxamide (37)

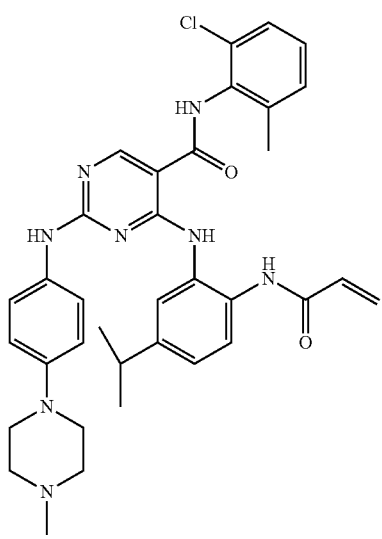 [SMILES: C=CC(=O)Nc1ccc(C(C)C)cc1Nc1nc(Nc2ccc(N3CCN(C)CC3)cc2)ncc1C(=O)Nc1c(C)cccc1Cl]

N-(2-chloro-6-methylphenyl)-2-{[4-(4-methylpiperazin-1-yl)phenyl]amino}-4-{[2-(prop-2-enamido)-5-(propan-2-yl)phenyl]amino}pyrimidine-5-carboxamide (37) was synthesized using the same route as described for (35). LC/MS: m/z calculated for [M+H]+639.29, found 638.89.

Synthesis of N-{2-[(5-chloro-2-{[4-(4-methylpiperazin-1-yl)phenyl]amino}pyrimidin-4-yl)amino]-3-fluorophenyl}prop-2-enamide (38)

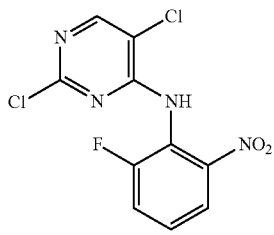 [SMILES: O=[N+]([O-])c1cccc(F)c1Nc1nc(Cl)ncc1Cl]

2,5-dichloro-N-(2-fluoro-6-nitrophenyl)pyrimidin-4-amine: 2-fluoro-6-nitroaniline (183 mg, 1.0 mmol) was dissolved in DMF (5 mL) and NaH (44 mg, 1.1 mmol, 60%) was added at 0° C. The suspension was stirred for 30 min and then 2,4,5-trichloropyrimidine was added to the mixture at 0° C. After stirring for 2 hours, water was added, followed by extraction with EtOAc. Combined extracts were washed with brine, concentrated and purified by silica gel chromatography to obtain the title compound (303 mg, 1.0 mmol, 100%). LC/MS: m/z calculated for [M+H]+302.89, found 303.15.

102

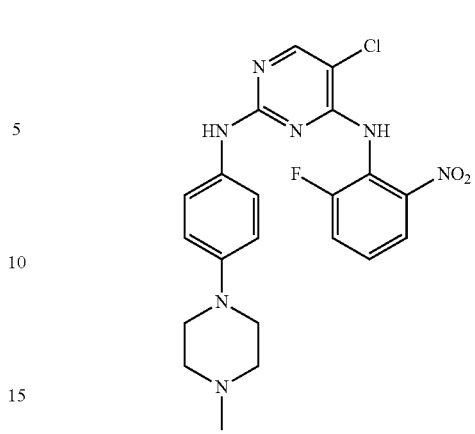

5-chloro-N4-(2-fluoro-6-nitrophenyl)-N2-(4-(4-methylpiperazin-1-yl)phenyl)pyrimidine-2,4-diamine: 2,5-dichloro-N-(2-fluoro-6-nitrophenyl)pyrimidin-4-amine and 4-(4-methylpiperazin-1-yl) aniline were reacted as described in General Procedure 2. LC/MS: m/z calculated for [M+H]+ 458.14, found 458.48.

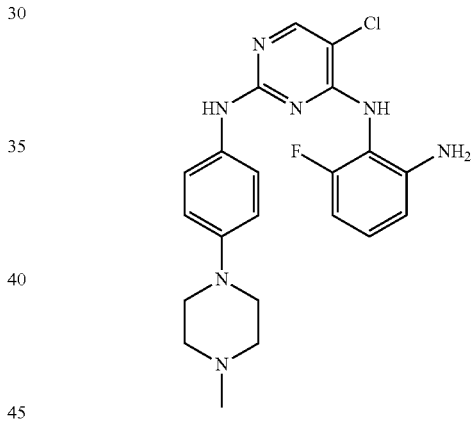

N4-(2-amino-6-fluorophenyl)-5-chloro-N2-(4-(4-methylpiperazin-1-yl)phenyl)pyrimidine-2,4-diamine: 5-chloro-N4-(2-fluoro-6-nitrophenyl)-N2-(4-(4-methylpiperazin-1-yl)phenyl)pyrimidine-2,4-diamine (457 mg, 1.0 mmol) was dissolved in EtOH (10 mL), and a solution of NH4Cl (428 mg, 8.0 mmol) in water (2 mL) was added. The solution was heated to 60 C, Fe (222 mg, 4.0 mmol) was added, and the reaction stirred at 80° C. for 4 hours. The mixture was filtered, diluted with water and basified using NaHCO3. The aqueous suspension was then extracted with EtOAc. Combined extracts were washed with brine, dried with Na2SO4, and concentrated to provide the title compound without further purification. LC/MS: m/z calculated for [M+H]+ 428.17, found 428.27.

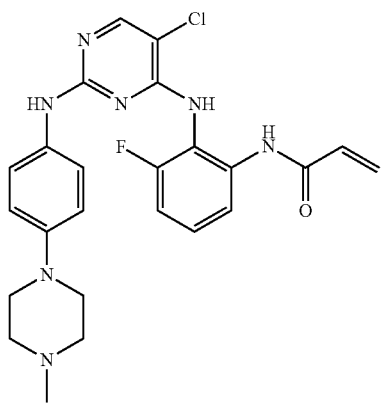 [SMILES: C=CC(=O)Nc1cccc(F)c1Nc1nc(Nc2ccc(N3CCN(C)CC3)cc2)ncc1Cl]

N-{2-[(5-chloro-2-{[4-(4-methylpiperazin-1-yl)phenyl]amino}pyrimidin-4-yl)amino]-3-fluorophenyl}prop-2-enamide (38): The acrylamide was installed on N4-(2-amino-6-fluorophenyl)-5-chloro-N2-(4-(4-methylpiperazin-1-yl)phenyl)pyrimidine-2,4-diamine as described in General Procedure Acryloyl, and the products purified by HPLC to obtain the title compound. LC/MS: m/z calculated for [M+H]+482.18, found 482.09.

Synthesis of N-{2-[(5-chloro-2-{[4-(4-methylpiperazin-1-yl)phenyl]amino}pyrimidin-4-yl)amino]-6-fluorophenyl}prop-2-enamide (39)

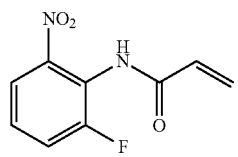

N-(6-fluoro-2-nitrophenyl)acrylamide: 2-fluoro-6-nitroaniline (50 mg, 0.23 mmol) was dissolved in THF (2 mL) and NaH (18 mg, 0.64 mmol, 60%) was added at 0° C. After stirring for 15 minutes, acryloyl chloride (26 μL, 0.32 mmol) in a small amount of THF was added. The reaction was quenched with water after 1 hour followed by extraction with EtOAc. Combined extracts were washed with brine, dried with Na₂SO₄, concentrated and purified by silica gel chromatography to provide the title compound (29 mg, 0.14 mmol, 43%). LC/MS: m/z calculated for [M+H]+211.04, found 211.29.

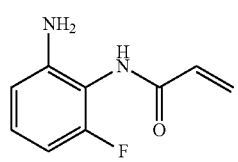

N-(2-amino-6-fluorophenyl)acrylamide: N-(6-fluoro-2-nitrophenyl)acrylamide (29 mg, 0.14 mmol) was dissolved in EtOH (2 mL), and a solution of NH₄Cl (59 mg, 1.1 mmol) in water (0.37 mL) was added. The solution was heated to 60° C., Fe (32 mg, 0.57 mmol) was added, and the reaction stirred at 80 C for 4 hours. The mixture was filtered, diluted with water and basified using NaHCO₃. The aqueous suspension was then extracted with EtOAc. Combined extracts were washed with brine, dried with Na₂SO₄, concentrated and purified by silica gel chromatography afford the title compound (12 mg, 0.067 mmol, 48%). LC/MS: m/z calculated for [M+H]+181.07, found 181.99.

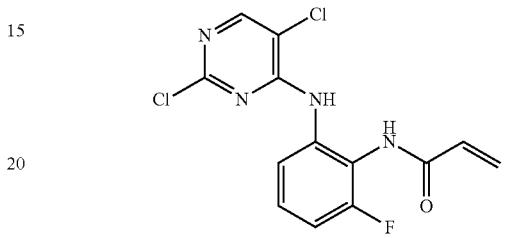

N-(2-((2,5-dichloropyrimidin-4-yl)amino)-6-fluorophenyl)acrylamide: N-(2-amino-6-fluorophenyl)acrylamide (12 mg, 0.067 mmol) was dissolved in 1-butanol (1 mL) and treated with DIEA (21 μL, 0.12 mmol). 2,4,5-trichloropyrimidine (15 μL, 0.13 mmol) was added, and the reaction stirred at 110° C. for 3 hours. The solvent was then evaporated and the crude product carried forward without further purification. LC/MS: m/z calculated for [M+H]+327.01, found 326.77.

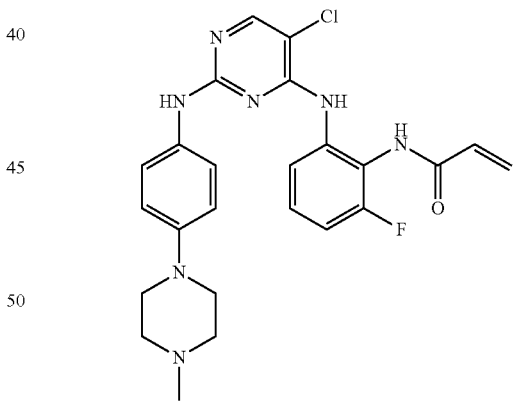

N-{2-[(5-chloro-2-{[4-(4-methylpiperazin-1-yl)phenyl]amino}pyrimidin-4-yl)amino]-6-fluorophenyl}prop-2-enamide (39): N-(2-((2,5-dichloropyrimidin-4-yl)amino)-6-fluorophenyl)acrylamide (~0.064 mmol) and 4-(4-methylpiperazin-1-yl) aniline were reacted as described in General Procedure 2, and the residue purified by HPLC to provide the title compound as a white solid (5.6 mg, 0.0094 mmol, 15% over 2 steps). LC/MS: m/z calculated for [M+H]+482.18, found 481.88.

Synthesis of N-{2-[(5-chloro-2-{[4-(4-methylpiper-azin-1-yl)phenyl]amino}pyrimidin-4-yl)amino]-5-fluorophenyl}prop-2-enamide (40)

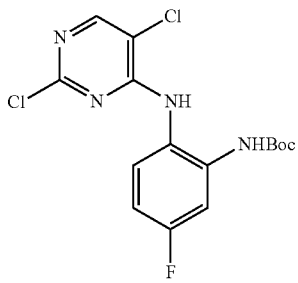 [SMILES: CC(C)(C)OC(=O)Nc1cc(F)ccc1Nc1nc(Cl)ncc1Cl]

tert-butyl (2-((2,5-dichloropyrimidin-4-yl)amino)-5-fluorophenyl)carbamate: 2,4,5-trichloropyrimidine and tert-butyl (2-amino-5-fluorophenyl)carbamate were reacted as described in General procedure 1A. (94%). LC/MS: m/z calculated for [M+H]+373.06, found 372.87.

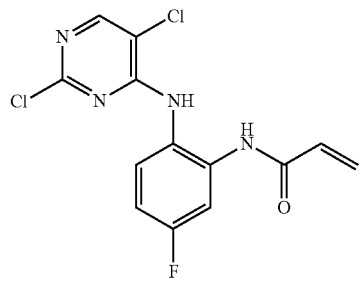 [SMILES: C=CC(=O)Nc1cc(F)ccc1Nc1nc(Cl)ncc1Cl]

N-(2-((2,5-dichloropyrimidin-4-yl)amino)-5-fluorophenyl)acrylamide: tert-butyl (2-((2,5-dichloropyrimidin-4-yl)amino)-5-fluorophenyl)carbamate was stirred in 2 mL of 1:1 TFA: DCM for 2 hours, before the solvent was evaporated. The resulting aniline was converted to the acrylamide using General Procedure 3, and the crude residue was purified by silica gel chromatography to obtain the title compound. (93% over 2 steps). LC/MS: m/z calculated for [M+H]+ 327.01, found 326.67.

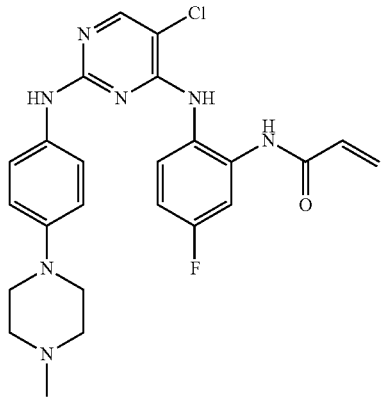 [SMILES: C=CC(=O)Nc1cc(F)ccc1Nc1nc(Nc2ccc(N3CCN(C)CC3)cc2)ncc1Cl]

N-{2-[(5-chloro-2-{[4-(4-methylpiperazin-1-yl)phenyl]amino}pyrimidin-4-yl)amino]-5-fluorophenyl}prop-2-enamide: N-(2-((2,5-dichloropyrimidin-4-yl)amino)-5-fluorophenyl)acrylamide and 4-(4-methylpiperazin-1-yl) aniline were reacted as described in General Procedure 2, and the residue purified by HPLC to provide the title compound as a white solid (16%). LC/MS: m/z calculated for [M+H]+ 482.18, found 481.88.

Synthesis of N-(2-chloro-6-methylphenyl)-4-{[5-fluoro-2-(prop-2-enamido)phenyl]amino}-2-{[4-(4-methylpiperazin-1-yl)phenyl]amino}pyrimidine-5-carboxamide (41)

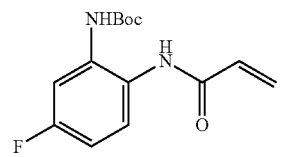

tert-butyl (2-acrylamido-5-fluorophenyl)carbamate: tert-butyl (2-amino-5-fluorophenyl)carbamate (50 mg, 0.22 mmol) was converted to the acrylamide by way of General Procedure 3. The crude residue was purified by silica gel chromatography to provide the title compound (38 mg, 0.14 mmol, 62%). LC/MS: m/z found 180.99.

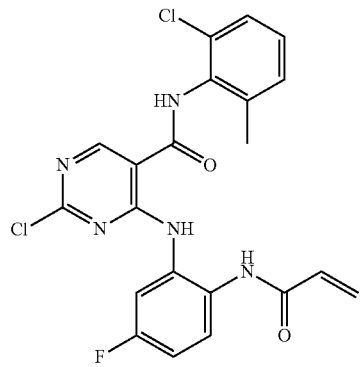 [SMILES: C=CC(=O)Nc1ccc(F)cc1Nc1nc(Cl)ncc1C(=O)Nc1c(C)cccc1Cl]

4-((2-acrylamido-4-fluorophenyl)amino)-2-chloro-N-(2-chloro-6-methylphenyl)pyrimidine-5-carboxamide: tert-butyl (2-acrylamido-5-fluorophenyl)carbamate (38 mg, 0.14 mmol) was stirred in 2 mL of 1:1 TFA: DCM for 2 hours, before the solvent was evaporated. The resulting residue was dissolved in 1-butanol (2 mL), treated with DIEA (115 μL, 0.66 mmol), and 2,4-dichloro-N-(2-chloro-6-methylphenyl)pyrimidine-5-carboxamide (35 mg, 0.11 mmol) was added. The reaction was stirred at 100 C for 3 hours before the solvent was evaporated and the residue purified by silica gel chromatography to provide the title compound (32 mg, 0.07 mmol, 63%). LC/MS: m/z calculated for [M+H]+460.07, found 459.87.

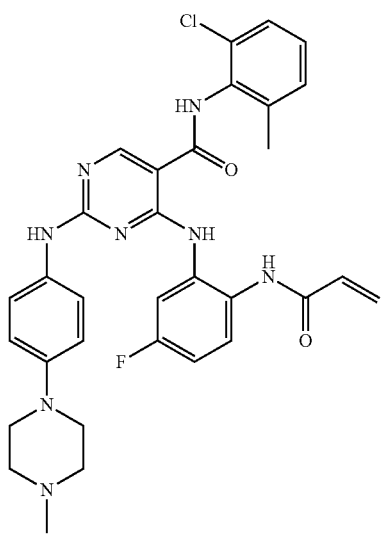 [SMILES: C=CC(=O)Nc1ccc(F)cc1Nc1nc(Nc2ccc(N3CCN(C)CC3)cc2)ncc1C(=O)Nc1c(C)cccc1Cl]

N-(2-chloro-6-methylphenyl)-4-{[5-fluoro-2-(prop-2-enamido)phenyl]amino}-2-{[4-(4-methylpiperazin-1-yl)phenyl]amino}pyrimidine-5-carboxamide (41): 4-((2-acrylamido-4-fluorophenyl)amino)-2-chloro-N-(2-chloro-6-methylphenyl)pyrimidine-5-carboxamide and 4-(4-methylpiperazin-1-yl) aniline were reacted as described in General Procedure 2, and the crude residue purified by HPLC to provide the title compound as a white solid (15%). LC/MS: m/z calculated for [M+H]+615.23, found 614.99.

Synthesis of N-(2-chloro-6-methylphenyl)-4-{[2-fluoro-6-(prop-2-enamido)phenyl]amino}-2-{[4-(4-methylpiperazin-1-yl)phenyl]amino}pyrimidine-5-carboxamide (42)

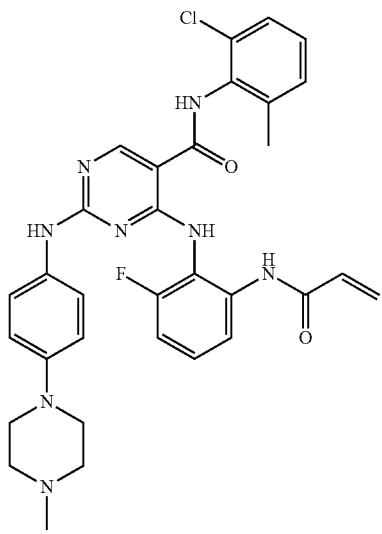 [SMILES: C=CC(=O)Nc1cccc(F)c1Nc1nc(Nc2ccc(N3CCN(C)CC3)cc2)ncc1C(=O)Nc1c(C)cccc1Cl]

N-(2-chloro-6-methylphenyl)-4-{[2-fluoro-6-(prop-2-enamido)phenyl]amino}-2-{[4-(4-methylpiperazin-1-yl)phenyl]amino}pyrimidine-5-carboxamide (42) was synthesized using the same route as described for (41). LC/MS: m/z calculated for [M+H]+639.29, found 638.89.

Synthesis of 4-((2-acrylamidophenyl)amino)-N-(2-chloro-6-methylphenyl)-2-((2-(4-methylpiperazin-1-yl)phenyl)amino)pyrimidine-5-carboxamide (43)

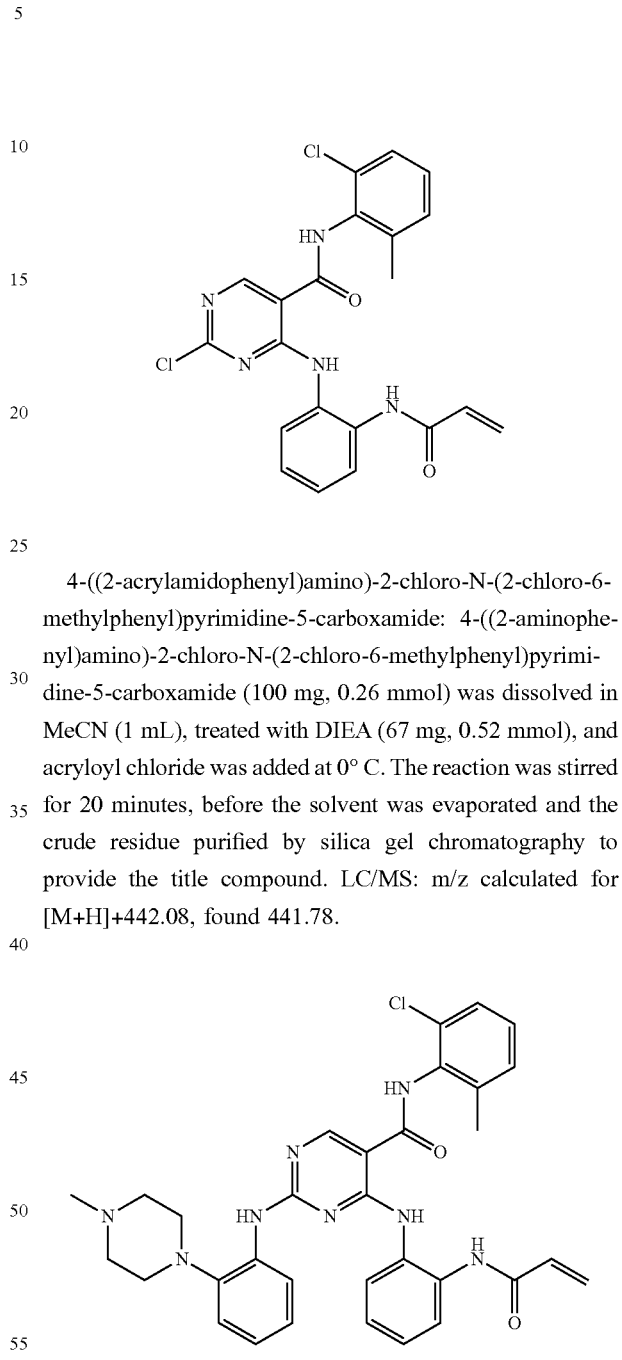

4-((2-acrylamidophenyl)amino)-2-chloro-N-(2-chloro-6-methylphenyl)pyrimidine-5-carboxamide: 4-((2-aminophenyl)amino)-2-chloro-N-(2-chloro-6-methylphenyl)pyrimidine-5-carboxamide (100 mg, 0.26 mmol) was dissolved in MeCN (1 mL), treated with DIEA (67 mg, 0.52 mmol), and acryloyl chloride was added at 0° C. The reaction was stirred for 20 minutes, before the solvent was evaporated and the crude residue purified by silica gel chromatography to provide the title compound. LC/MS: m/z calculated for [M+H]+442.08, found 441.78.

4-((2-acrylamidophenyl)amino)-N-(2-chloro-6-methylphenyl)-2-((2-(4-methylpiperazin-1-yl)phenyl)amino)pyrimidine-5-carboxamide (43): 4-((2-acrylamidophenyl)amino)-2-chloro-N-(2-chloro-6-methylphenyl)pyrimidine-5-carboxamide and 2-(4-methylpiperazin-1-yl) aniline were reacted as described in General Procedure 2, and the crude residue purified by HPLC to provide the title compound. LC/MS: m/z calculated for [M+H]+597.24, found 596.89.

Synthesis of 4-((2-acrylamidophenyl)amino)-N-(2-chloro-6-methylphenyl)-2-((3-(4-methylpiperazin-1-yl)phenyl)amino)pyrimidine-5-carboxamide (44)

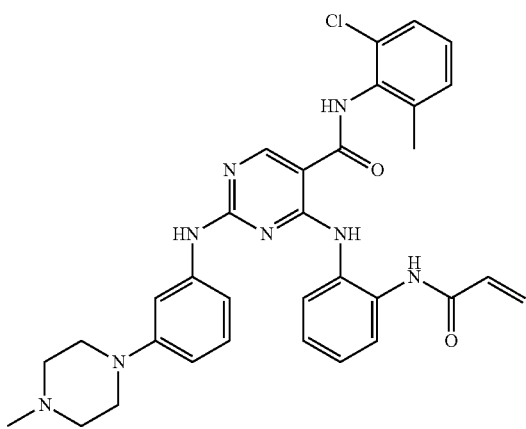 [SMILES: C=CC(=O)Nc1ccccc1Nc1nc(Nc2cccc(N3CCN(C)CC3)c2)ncc1C(=O)Nc1c(C)cccc1Cl]

4-((2-acrylamidophenyl)amino)-N-(2-chloro-6-methylphenyl)-2-((3-(4-methylpiperazin-1-yl)phenyl)amino)pyrimidine-5-carboxamide (44) was synthesized using the same route as described for (43). LC/MS: m/z calculated for [M+H]+597.24, found 597.29. $^1$H NMR (500 MHZ, DMSO-d$_6$) δ 10.73 (s, 1H), 9.88 (s, 1H), 9.72 (s, 1H), 9.67 (s, 1H), 9.61 (s, 1H), 8.86 (s, 1H), 8.00 (s, 1H), 7.36-7.28 (m, 2H), 7.25-7.12 (m, 5H), 7.09 (td, J=7.6, 1.6 Hz, 1H), 7.04 (t, J=8.1 Hz, 1H), 6.60 (d, J=8.9 Hz, 1H), 6.29 (dd, J=17.1, 10.3 Hz, 1H), 6.07 (dd, J=17.1, 2.0 Hz, 1H), 5.57 (dd, J=10.2, 2.0 Hz, 1H), 3.55 (d, J=13.3 Hz, 2H), 3.39 (d, J=11.9 Hz, 2H), 3.06-3.00 (m, 2H), 2.84-2.76 (m, 5H), 2.16 (s, 3H).

Synthesis of 4-((2-acrylamidophenyl)amino)-N-(2-chloro-6-methylphenyl)-2-((3-methyl-4-(4-methylpiperazin-1-yl)phenyl)amino)pyrimidine-5-carboxamide (45)

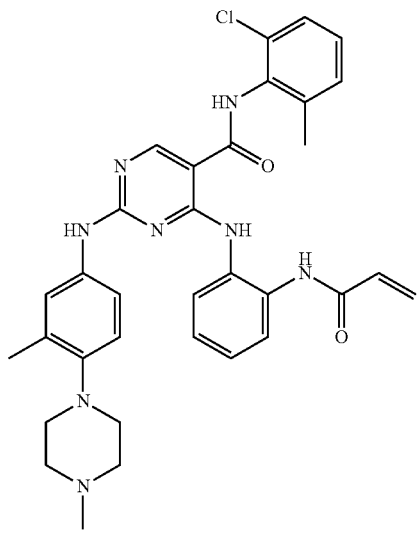 [SMILES: C=CC(=O)Nc1ccccc1Nc1nc(Nc2ccc(N3CCN(C)CC3)c(C)c2)ncc1C(=O)Nc1c(C)cccc1Cl]

4-((2-acrylamidophenyl)amino)-N-(2-chloro-6-methylphenyl)-2-((3-methyl-4-(4-methylpiperazin-1-yl)phenyl)amino)pyrimidine-5-carboxamide (45) was synthesized using the same route as described for (43). LC/MS: m/z calculated for [M+H]+611.26, found 611.39. $^1$H NMR (500 MHZ, DMSO-d$_6$) δ 10.77 (s, 1H), 9.85 (s, 1H), 9.69 (s, 1H), 9.66 (s, 1H), 9.61 (s, 1H), 8.84 (s, 1H), 8.01 (s, 1H), 7.46 (d, J=2.6 Hz, 1H), 7.37-7.29 (m, 3H), 7.26-7.14 (m, 3H), 7.09 (t, J=7.6 Hz, 1H), 6.87 (d, J=8.6 Hz, 1H), 6.28 (dd, J=17.1, 10.2 Hz, 1H), 6.06 (dd, J=17.1, 2.0 Hz, 1H), 5.56 (dd, J=10.3, 2.0 Hz, 1H), 3.43 (d, J=11.7 Hz, 2H), 3.19-3.11 (m, 2H), 3.08 (d, J=13.6 Hz, 2H), 2.88-2.80 (m, 5H), 2.16 (s, 3H), 2.11 (s, 3H).

Synthesis of N-{4-methyl-2-[(2-{[4-(4-methylpiperazin-1-yl)phenyl]amino}thieno[3,2-d]pyrimidin-4-yl)amino]phenyl}prop-2-enamide (46)

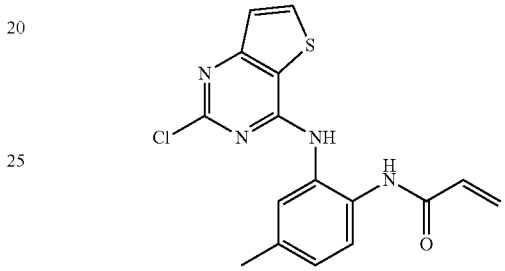

N-(2-((2-chlorothieno[3,2-d]pyrimidin-4-yl)amino)-4-methylphenyl)acrylamide: N-(2-amino-4-methylphenyl)acrylamide (83 mg, 0.47 mmol) was dissolved in isopropanol (2 mL) and 2,4-dichlorothieno[3,2-d]pyrimidine (96 mg, 0.47 mmol) was added. The suspension was stirred for 2 days at rt before the solvent was evaporated and the residue purified by silica gel chromatography to provide the title compound (61 mg, 0.18 mmol, 38%). LC/MS: m/z calculated for [M+H]+345.05, found 344.97.

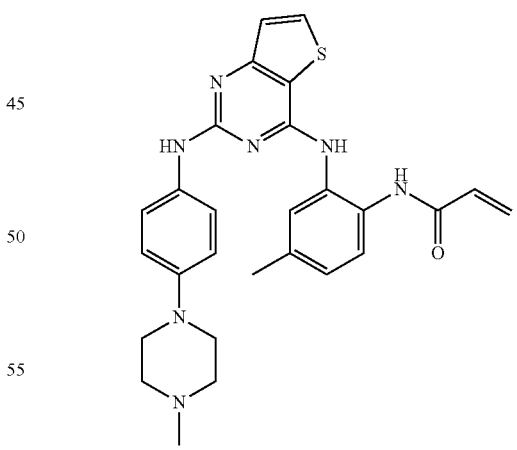

N-{4-methyl-2-[(2-{[4-(4-methylpiperazin-1-yl)phenyl]amino}thieno[3,2-d]pyrimidin-4-yl)amino]phenyl}prop-2-enamide (46): N-(2-((2-chlorothieno[3,2-d]pyrimidin-4-yl)amino)-4-methylphenyl)acrylamide and 4-(4-methylpiperazin-1-yl) aniline were reacted as described in General Procedure 2, and the products purified by HPLC to provide the title compound (60%). LC/MS: m/z calculated for [M+H]+500.22, found 500.28.

Synthesis of N-{4-methyl-2-[(2-{[4-(4-methylpiperazin-1-yl)phenyl]amino}furo [3,2-d]pyrimidin-4-yl)amino]phenyl}prop-2-enamide (47)

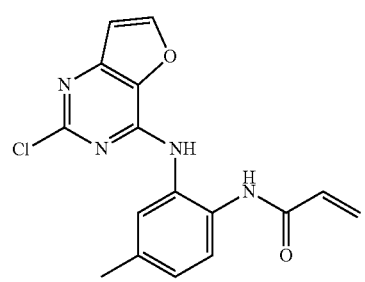 [SMILES: C=CC(=O)Nc1ccc(C)cc1Nc1nc(Cl)nc2ccsc12]

N-(2-((2-chlorofuro[3,2-d]pyrimidin-4-yl)amino)-4-methylphenyl)acrylamide: N-(2-amino-4-methylphenyl)acrylamide (83 mg, 0.47 mmol) was dissolved in methanol (2 mL) and 2,4-dichlorothieno[3,2-d]pyrimidine (96 mg, 0.47 mmol) was added. The suspension was stirred for 2 days at rt before the solvent was evaporated and the residue purified by silica gel chromatography to provide the title compound (95 mg, 0.29 mmol, 61%). LC/MS: m/z calculated for [M+H]+329.07, found 329.07.

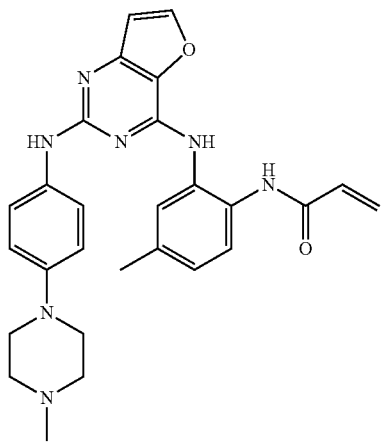 [SMILES: C=CC(=O)Nc1ccc(C)cc1Nc1nc(Nc2ccc(N3CCN(C)CC3)cc2)nc2ccoc12]

N-{4-methyl-2-[(2-{[4-(4-methylpiperazin-1-yl)phenyl]amino}furo [3,2-d]pyrimidin-4-yl)amino]phenyl}prop-2-enamide (47): N-(2-((2-chlorofuro[3,2-d]pyrimidin-4-yl)amino)-4-methylphenyl)acrylamide and 4-(4-methylpiperazin-1-yl) aniline were reacted as described in General Procedure 2, and the crude residue purified by HPLC to provide the title compound (36%). LC/MS: m/z calculated for [M+H]+484.24, found 484.28.

Synthesis of N-(2-chloro-6-methylphenyl)-2-{[4-(4-methylpiperazin-1-yl)phenyl]amino}-4-[(2-propanamidophenyl)amino]pyrimidine-5-carboxamide (48)

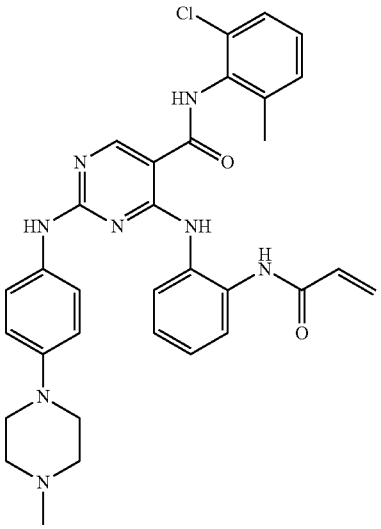 [SMILES: C=CC(=O)Nc1ccccc1Nc1nc(Nc2ccc(N3CCN(C)CC3)cc2)ncc1C(=O)Nc1c(C)cccc1Cl]

N-(2-chloro-6-methylphenyl)-2-{[4-(4-methylpiperazin-1-yl)phenyl]amino}-4-[(2-propanamidophenyl)amino]pyrimidine-5-carboxamide (48): N4-(2-amino-6-fluorophenyl)-5-chloro-N2-(4-(4-methylpiperazin-1-yl)phenyl)pyrimidine-2,4-diamine (54 mg, 0.10 mmol) was dissolved in THF (1 mL) and sat. aqueous $NaHCO_3$ (1 mL), and propionyl chloride in a small amount of THF was slowly titrated in until the starting material was consumed. Water was then added, followed by extraction by EtOAc. Combined extracts were washed with brine, dried over $Na_2SO_4$, concentrated, and purified by HPLC to obtain the title compound (13 mg, 0.021 mmol, 21%). LC/MS: m/z calculated for [M+H]+599.26, found 598.69. $^1$H NMR (500 MHZ, DMSO-$d_6$) δ 10.92 (s, 1H), 9.86 (s, 1H), 9.64 (s, 2H), 9.39 (s, 1H), 8.84 (s, 1H), 8.30-8.00 (s, 1H), 7.48 (d, J=8.2 Hz, 2H), 7.34 (dd, J=7.6, 1.8 Hz, 1H), 7.27-7.11 (m, 4H), 7.03 (t, J=7.6 Hz, 1H), 6.86 (d, J=8.4 Hz, 2H), 3.70 (d, J=13.2 Hz, 2H), 3.47 (d, J=12.1 Hz, 2H), 3.12 (d, J=11.2 Hz, 2H), 2.89-2.79 (m, 5H), 2.18 (s, 3H), 2.14 (q, J=7.6 Hz, 2H), 0.87 (t, J=7.6 Hz, 3H).

Example 2: In Vitro Test of Exemplary Compounds

All examples described herein possessed activity in a commercial assay from SelectScreen Kinase Profiling Services in ThermoFisher Scientific company as listed unless otherwise noted. $IC_{50}$<1 nM (+++++), $IC_{50}$ 1 nM-10 nM (++++), $IC_{50}$ 10 nM-100 nM (+++), $IC_{50}$ 100 nM-1 μM (++), $IC_{50}$ 1 μM-10 μM (+), $IC_{50}$>10 μM (−), or not determined (ND).

| Compound No. | SRC $IC_{50}$ | YES1 (nM) |
|---|---|---|
| SM1-71 | ++++ | ++++ |
| 1 | ++++ | ++++ |
| 2 | ++++ | ++++ |
| 3 | ++++ | ++++ |
| 4 | ++++ | ++++ |

-continued

| Compound No. | SRC IC$_{50}$ | YES1 (nM) |
|---|---|---|
| 5 | ++++ | ++++ |
| 6 | ++++ | ++++ |
| 7 | ++++ | ++++ |
| 8 | ++++ | ++++ |
| 9 | ++++ | ++++ |
| 10 | ++++ | +++++ |
| 11 | ++++ | ++++ |
| 12 | +++ | ++++ |
| 13 | +++ | ++++ |
| 14 | ++ | +++ |
| 15 | ++++ | ++++ |
| 16 | ++++ | ++++ |
| 17 | ++++ | ND |
| 18 | ++++ | +++++ |
| 19 | − | − |
| 20 | + | + |
| 21 | ++++ | ND |
| 22 | ++++ | ND |
| 23 | + | ND |
| 24 | +++ | ND |
| 25 | + | ND |
| 26 | +++ | ND |
| 27 | ++++ | +++++ |
| 28 | ++++ | +++++ |
| 29 | ++ | ND |
| 30 | − | ND |
| 31 | + | ++ |
| 32 | +++ | ++++ |
| 33 | ++++ | ++++ |
| 34 | ++++ | ++++ |
| 35 | +++ | ND |
| 36 | ++ | ++++ |
| 37 | ++ | ++++ |
| 38 | ++++ | ++++ |
| 39 | ++++ | ND |
| 40 | ++++ | ND |
| 41 | ++++ | +++++ |
| 42 | ++++ | +++++ |
| 43 | − | ND |
| 44 | +++ | +++++ |
| 45 | ++++ | +++++ |
| 46 | ++ | +++ |
| 47 | ++ | +++ |
| 48 | ++++ | +++++ |
| 49 | +++ | ND |
| 50 | ++++ | ND |
| 51 | +++ | ND |
| 52 | ++++ | ND |
| 53 | ++ | ND |
| 54 | ++++ | ND |
| 55 | ++++ | ND |
| 56 | ++ | ND |
| − | − | − |

Figure 3A:
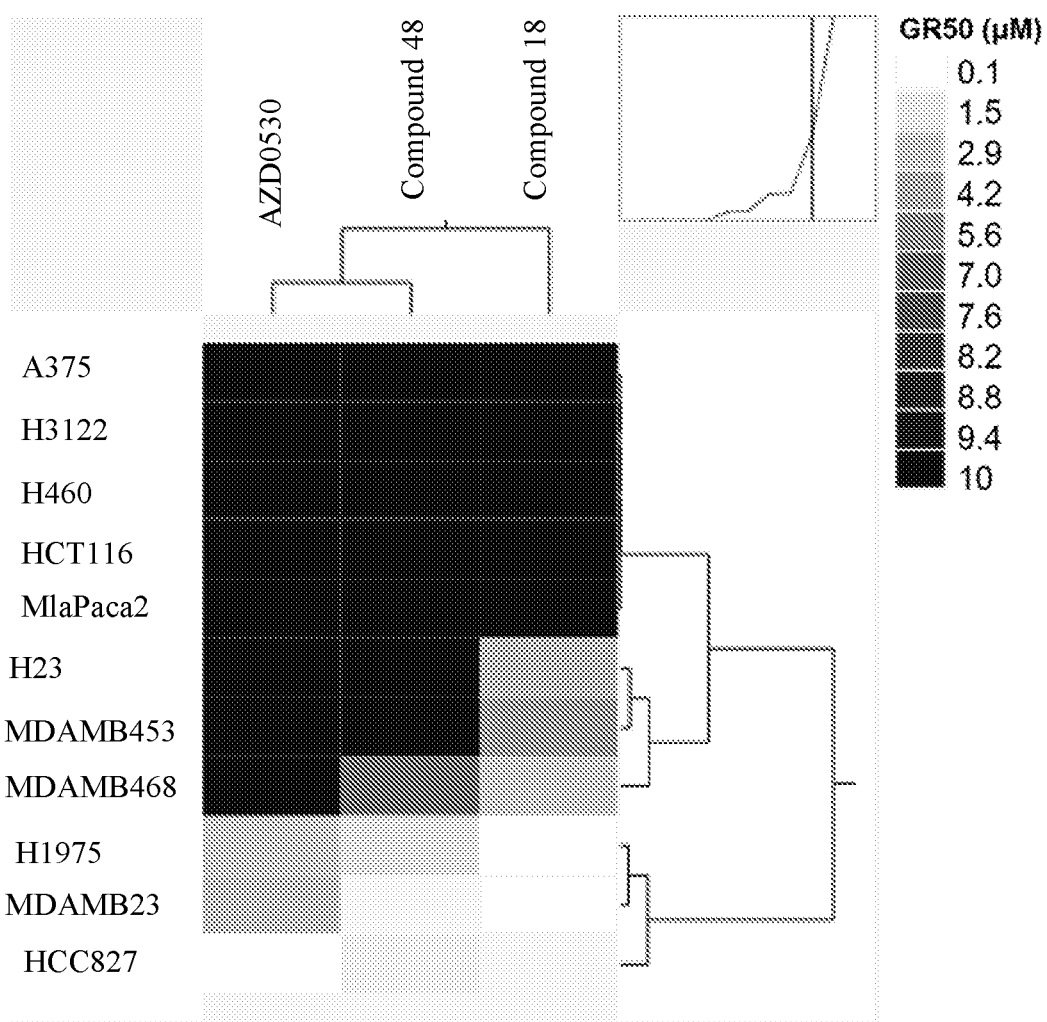
FIG. 3A shows the $GR_{50}$ of a range of cancer cell lines that were treated with varying doses of 18, 48, or AZD0530 for a period of 72 h and cell viability was assessed using the Cell TiterGlo reagent. Growth inhibition was calculated using the growth-rate adjusted metrics, where $GR_{50}$ is similar to $IC_{50}$, but has been corrected for variable cell division times. Each experiment was conducted in technical triplicate and repeated twice.
Figure 3B:
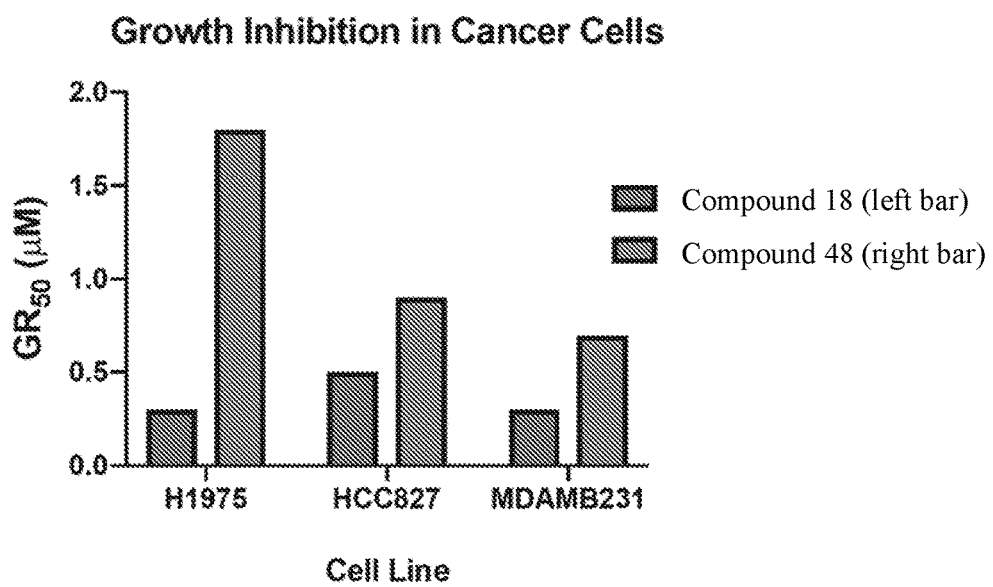
FIG. 3B. depicts the growth inhibitory potency of 18 and 48 that was compared across the three sensitive cell lines. Values used to plot the bar graphs are the average $GR_{50}$ values from two independent experiments.

Example 3: Biological Characterization of Exemplary Compounds 18, 48, and AZD0530 (control) were screened for their growth inhibitory potency against a range of cancer cell lines. The cell lines consisted of melanoma (A375), non-small cell lung cancer (H31222, H460, H23, H1975, HCC827), colorectal (HCT116), pancreatic (MiaPaca2) and triple negative breast cancer (MDA-MB-231, MDA-MB-453, MDA-MB-468) cells. Each of these cell lines bear distinct genetic mutations and oncogenic drivers. To account for confounding effects arising from differing doubling times amongst cell types, we utilized recently described growth rate (GR) corrected calculations, which resulted in GR$_{50}$. The results from the growth inhibitory assay show that among the cell lines screened, MDA-MB-231, H1975 and HCC827 cells were most sensitive to inhibition by SRC-targeting compounds, and demonstrated sub-micromolar to low micromolar GR$_{50}$ values (FIG. 3A). Furthermore, 18 showed slightly more potent inhibition across the three cell lines, compared to its reversible analogue, 48 (FIG. 3B).

Figure 4A:
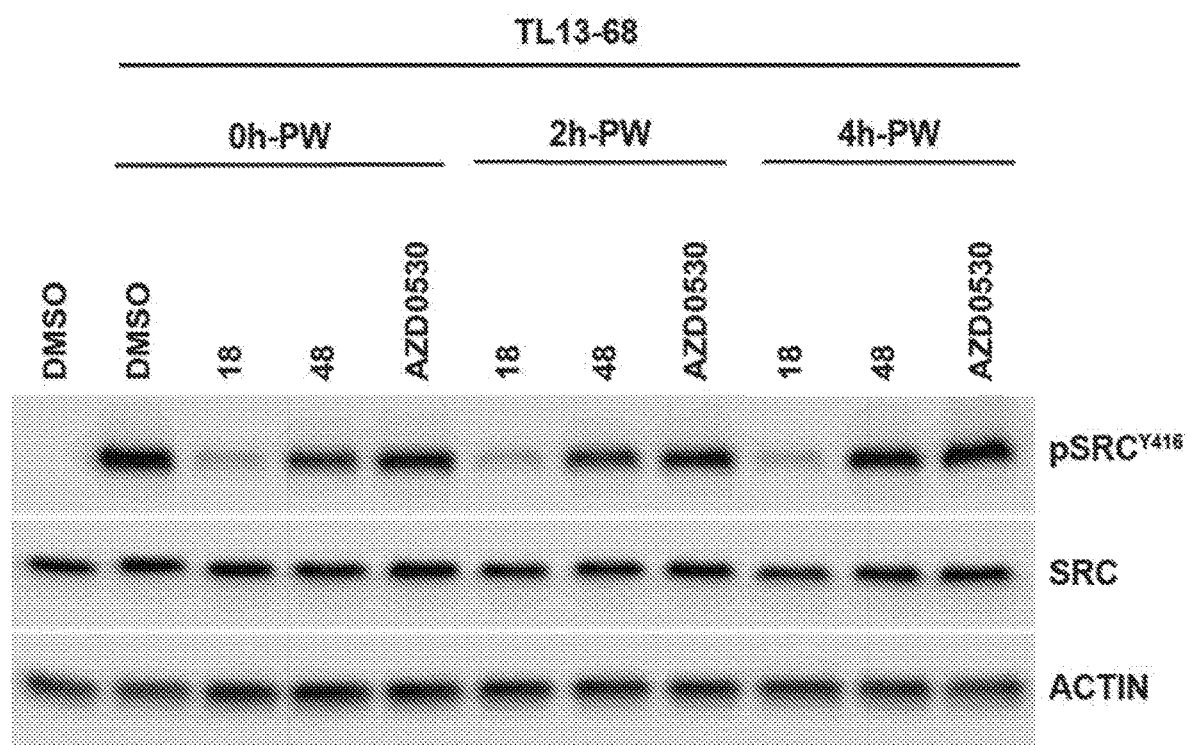
FIG. 4A. shows a western blot of H1975 cells were treated with 1 μM of 18 or 48 or AZ0530 for a period of 2 h, followed by drug washout, where drug-containing medium was replaced by fresh drug-free medium. Cells were subsequently collected and lysed 0 h, 2 h and 4 h post-washout. For cellular target engagement, lysate samples were incubated with a biotinylated compound (TL13-68) capable of competing for SRC binding. Proteins bound by TL13-68 were pulled down using streptavidin beads and visualized using Western blotting.
Figure 4B:
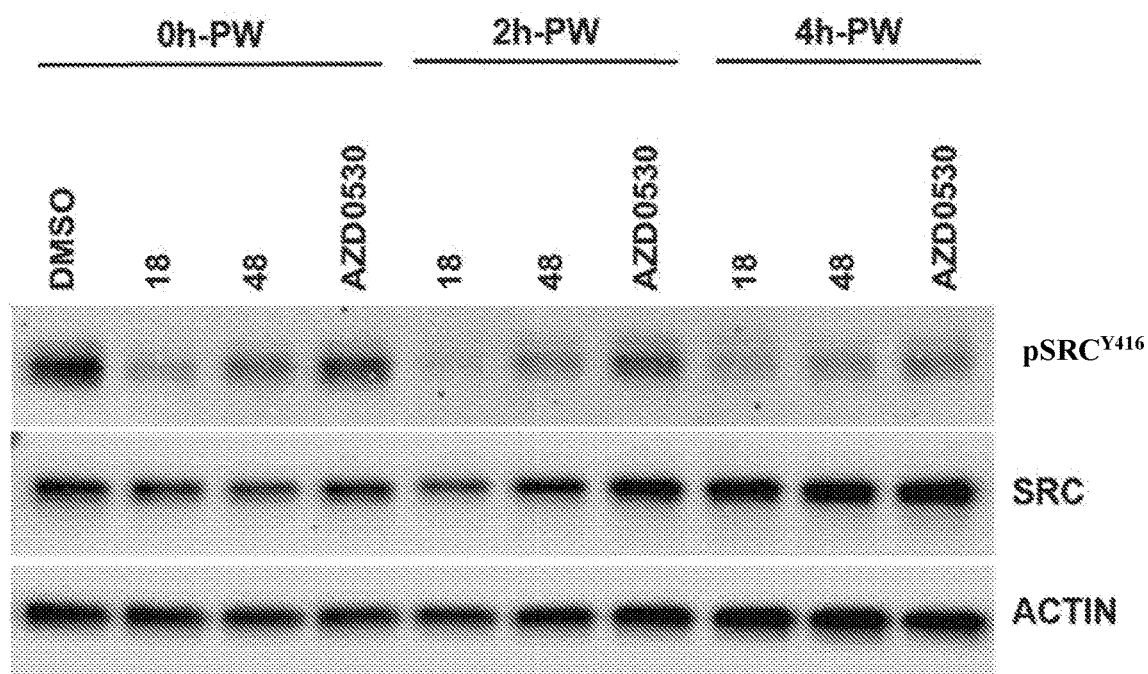
FIG. 4B. shows a western blot of H1975 cells were treated with 1 μM of 18 or 48 or AZ0530 for a period of 2 h, followed by drug washout, where drug-containing medium was replaced by fresh drug-free medium. Cells were subsequently collected and lysed 0 h, 2 h and 4 h post-washout. Signaling analysis was carried out using Western blotting, where phosphorylation signal was measured using the pSRC$^{Y416}$ antibody. Each experiment was carried out in biological duplicates and the above blots represent a single experiment conducted.

In order to discern the binding kinetics of the covalent and non-covalent compounds towards SRC, cellular target engagement and signaling analyses was conducted using washout conditions. Briefly, H1975 cells were treated with 1 µM of 18, 48 or AZD0530 for 2 h followed by drug-removal and replacement with drug-free medium. Cells were subsequently extracted and lysed 0 h, 2 h and 4 h post-washout. For the cellular target engagement assay, lysates were further incubated with 1 µM of a biotinylated-compound (TL13-68), also capable of binding SRC. Western blotting was used to determine the level of SRC inhibition in both the target engagement and signaling assays. The results showed that 18 resulted in potent and sustained binding of SRC up to 4 h post-washout, unlike 48 or AZD0530, the reversible compounds (FIG. 4A). Similarly, 18 also demonstrated potent and sustained inhibition of p-SRC$^{Y416}$ signaling up to 4 h post-washout (FIG. 4B). Despite not binding SRC covalently, 48 also showed moderate inhibition p-SRC$^{Y416}$ up to 4 h post-washout (FIG. 4B). These results demonstrate the ability of the covalent SRC inhibitor to induce potent and sustained inhibition of SRC along with growth inhibition in SRC-expressing cancer cell lines.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of Formula (I):

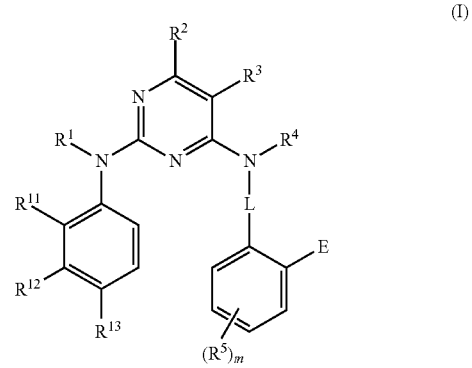

or a pharmaceutically acceptable salt thereof, wherein:

E is an electrophile;

L is a bond or alkylenyl;

each $R^1$ is independently selected from hydrogen and alkyl;

$R^2$ is selected from hydrogen and amino;

$R^3$ is selected from alkyl, —C(=O)NR$^1$-alkyl, —C(=O)NR$^1$-aryl, alkoxy, aryl, heteroaryl, cycloalkyl, halogen, and aralkyloxy; or $R^2$ and $R^3$, taken together with the carbon atoms to which they are attached, combine to form a heteroaryl;

$R^4$ is selected from hydrogen and alkyl;

each $R^5$ is independently selected from alkyl and halogen;

m is 0 or 1;

two of $R^{11}$, $R^{12}$, and $R^{13}$ are independently hydrogen or alkyl;

one of $R^{11}$, $R^{12}$, and $R^{13}$ is selected from

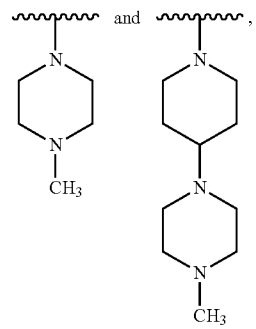

provided that if $R^1$ is hydrogen, $R^2$ is hydrogen, $R^3$ is chloro, $R^4$ is hydrogen, m is 0, E is

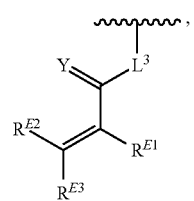

L is a bond, Y is O, $L^3$ is —NR$^{L3a}$—, $R^{L3a}$, $R^{E1}$, $R^{E2}$, and $R^{E3}$ are hydrogen, $R^{11}$ is hydrogen, and $R^{12}$ is hydrogen, then $R^{13}$ is not

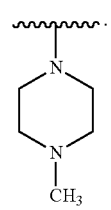

2. The compound of claim 1, wherein the electrophile is selected from:

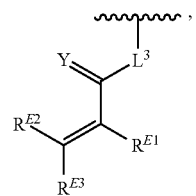 (i-1)

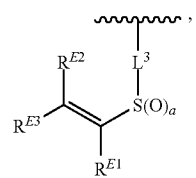 (i-2)

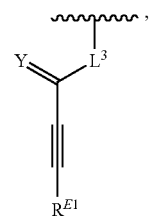 (i-3)

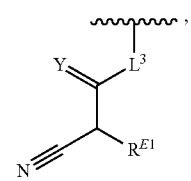 (i-4)

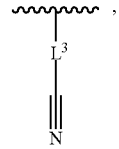 (i-5)

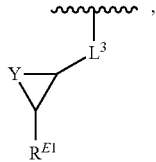 (i-6)

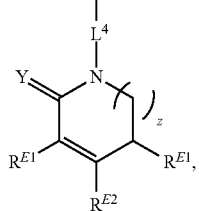 (i-7)

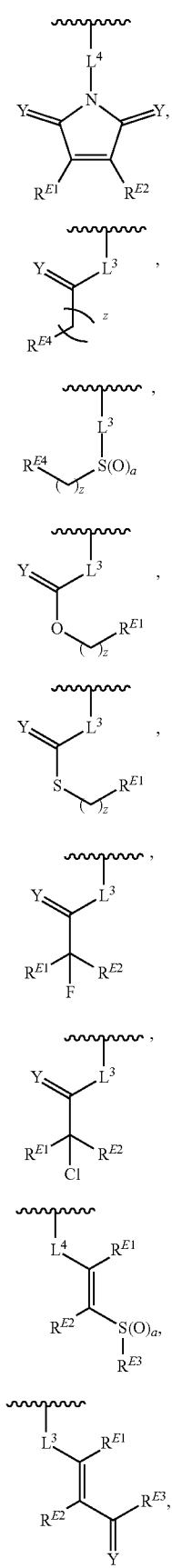
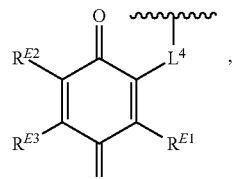
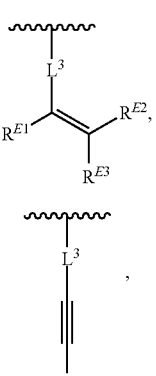
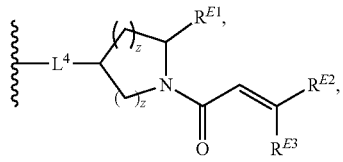

-continued
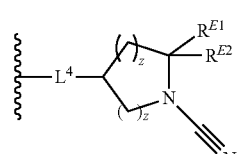 (i-25)
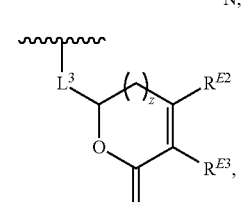 (i-26)
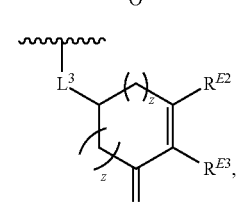 (i-27)
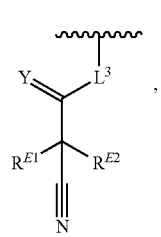 (i-28)
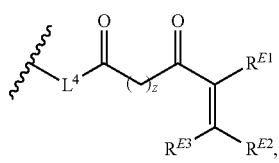 (i-29)
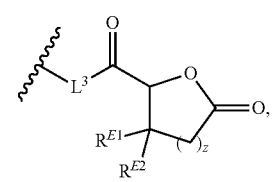 (i-30)
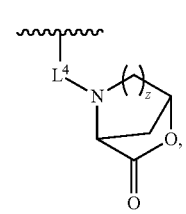 (i-31)
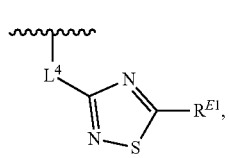 (i-32)
-continued
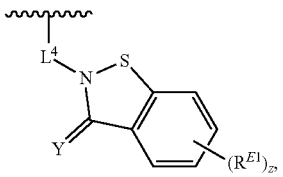 (i-33)
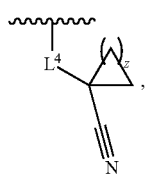 (i-34)
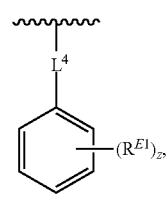 (i-35)
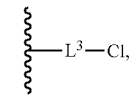 (i-36)
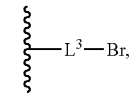 (i-37)
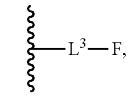 (i-38)
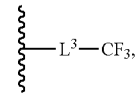 (i-39)
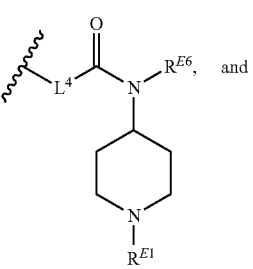 (i-40) and
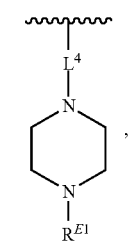 (i-41)
wherein,
⟨ indicates the position of attachment to the compound of Formula (I);
$L^3$ is a bond or an optionally substituted $C_{1-4}$ hydrocarbon chain, optionally wherein one or more carbon units of the hydrocarbon chain are independently replaced with —C—O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S) NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group or alkyl;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2;

each instance of z is independently 0, 1, 2, 3, 4, 5, or 6, as valency permits; and each instance of R$^8$, if present, is independently selected from hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of R$^{D1a}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or optionally two instances of R$^{D1a}$ are taken together with their intervening atoms to form a substituted or unsubstituted heterocyclic or substituted or unsubstituted heteroaryl ring; or two R$^8$ groups are joined to form an optionally substituted carbocyclyl, optionally substituted heterocyclyl, optionally substituted aryl, or optionally substituted heteroaryl ring.

3. The compound of claim 2, wherein the electrophile is of formula:

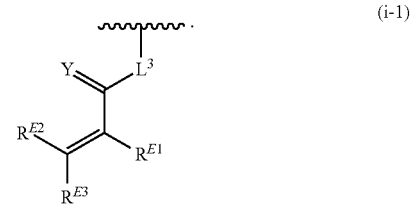

(i-1)

4. The compound of claim 3, wherein R$^{E1}$, R$^{E2}$, and R$^{E3}$ are each hydrogen or R$^{E1}$ and R$^{E2}$ are each hydrogen and R$^{E3}$ is aminoalkyl.

5. The compound of claim 4, wherein Y is O.

6. The compound of claim 5, wherein L$^3$ is —NR$^{L3a}$— and R$^{L3a}$ is hydrogen.

7. The compound of claim 2, wherein the electrophile is of formula:

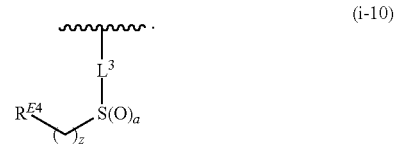

(i-10)

8. The compound of claim 7, wherein L$^3$ is a bond.

9. The compound of claim 7, wherein R$^{E4}$ is alkyl.

10. The compound of claim 2, wherein the electrophile is of formula:

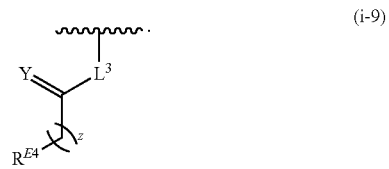

(i-9)

11. The compound of claim 10, wherein L$^3$ is a bond.

12. The compound of claim 11, wherein z is 1 and R$^{E4}$ is halo.

13. The compound of claim 2, wherein the electrophile is of formula:

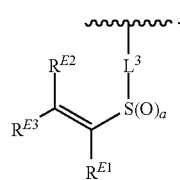
(i-2)

14. The compound of claim 13, wherein $L^3$ is a bond.
15. The compound of claim 14, wherein $R^{E1}$, $R^{E2}$, and $R^{E3}$ are each hydrogen.
16. The compound of claim 1, wherein L is alkylenyl.
17. The compound of claim 1, wherein the compound is represented by Formula (Ia), (Ib), (Ic) or (Id):

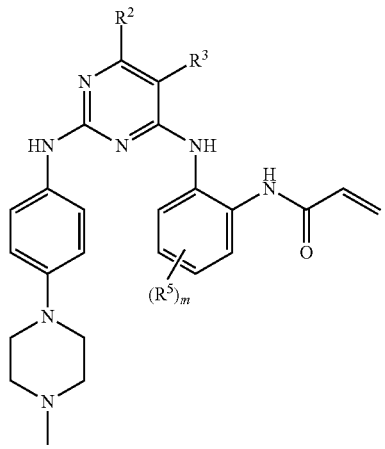
(Ia)

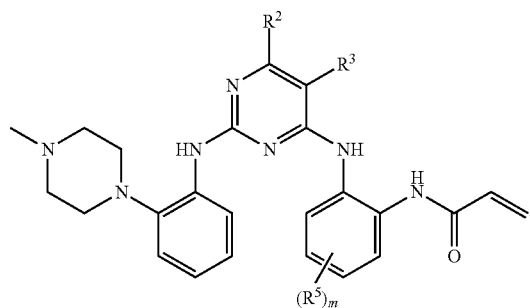
(Ib)

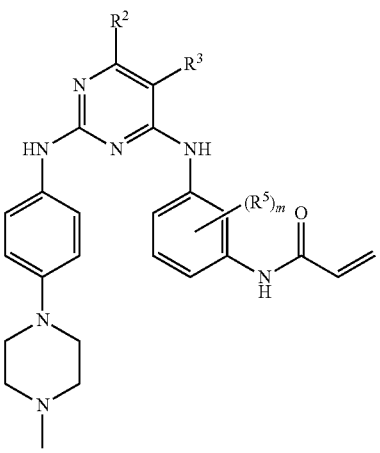
(Ic)

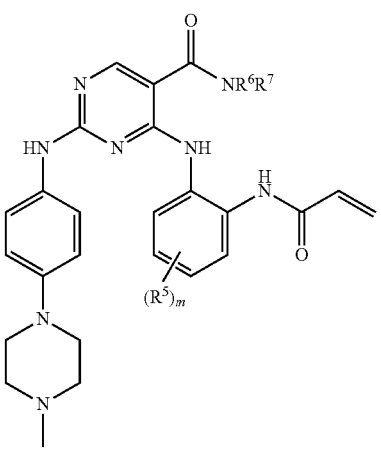
(Id)

or a pharmaceutically acceptable salt thereof.

18. The compound of claim 1, wherein $R^3$ is halo, alkyl, cycloalkyl, aryl, heteroaryl, or aralkyloxy.
19. The compound of claim 1, wherein the compound is represented by Formula (Ie) or (If):

(Ie)

-continued
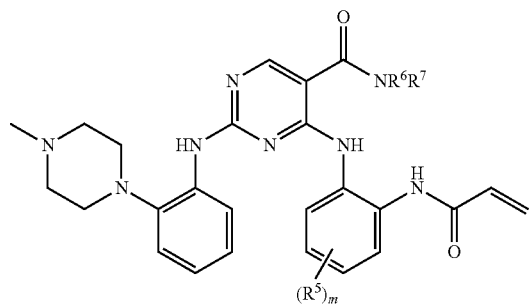
(If)
or a pharmaceutically acceptable salt thereof, wherein:
$R^6$ is hydrogen or alkyl; and
$R^7$ is alkyl or aryl.
20. The compound of claim 19, wherein $R^7$ is substituted with alkyl, aryloxy, halo, carboxyl, alkoxy, or cyano.
21. The compound of claim 1, wherein $R^2$ and $R^3$ combine to form a heteroaryl.
22. A compound selected from:
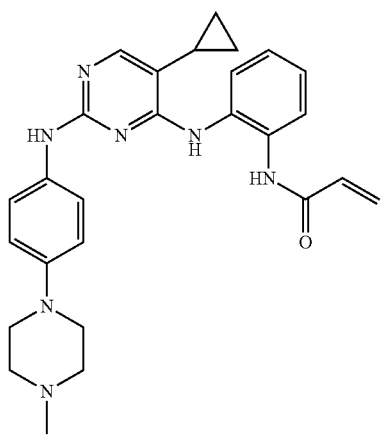
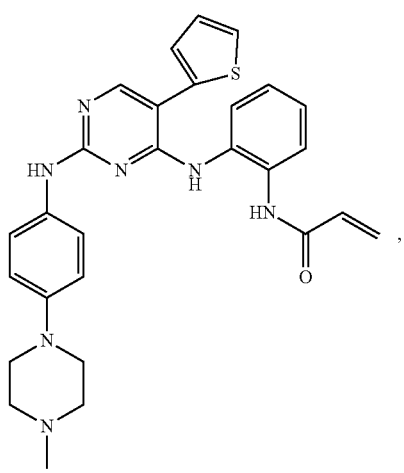
-continued
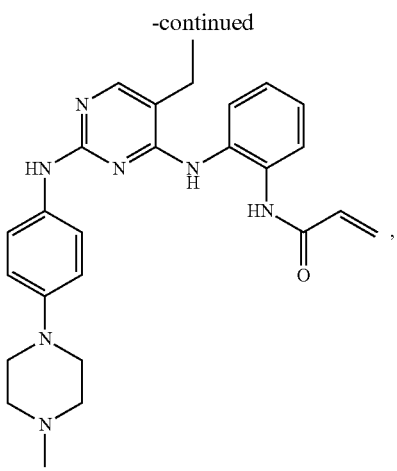
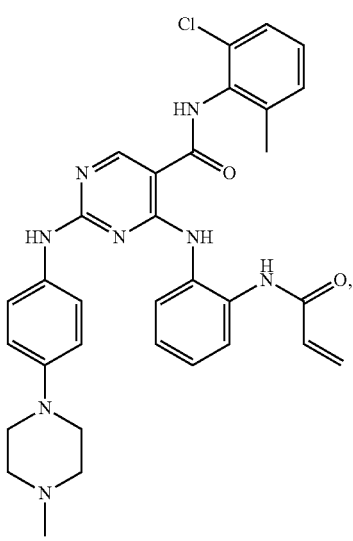
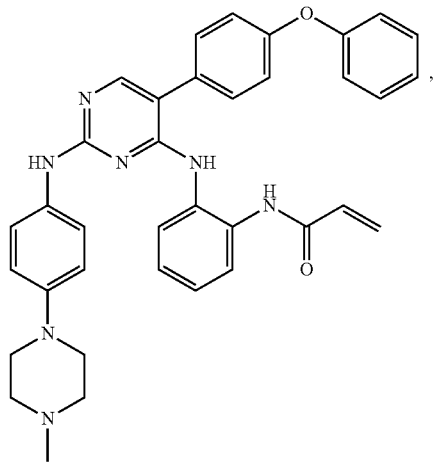

127
-continued
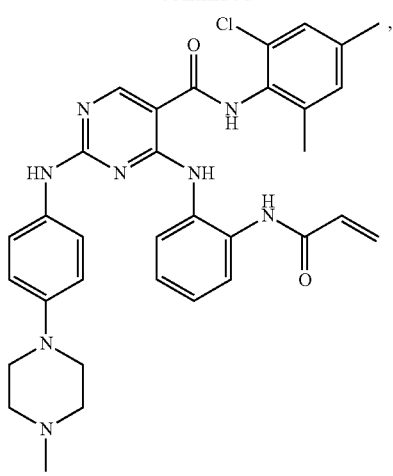
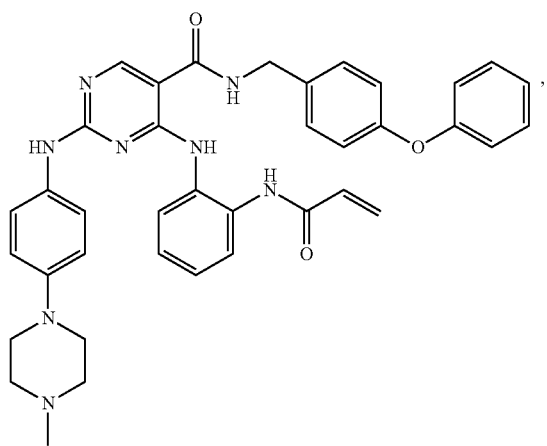
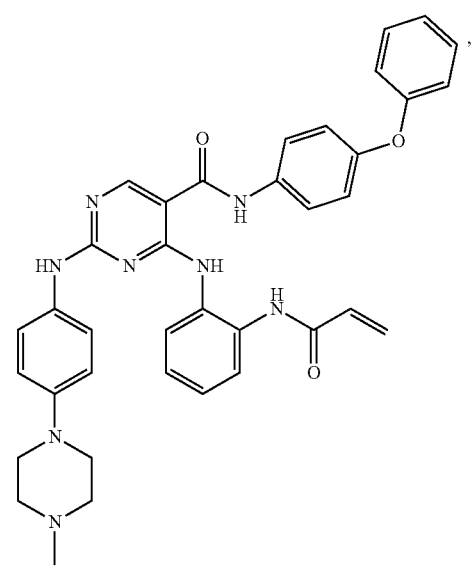
128
-continued
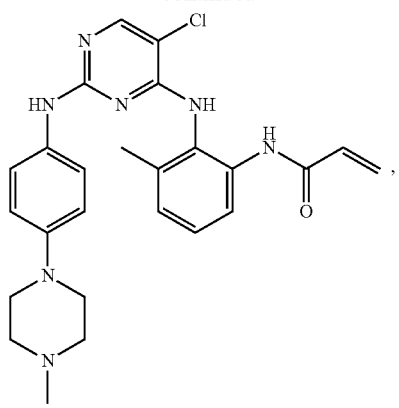
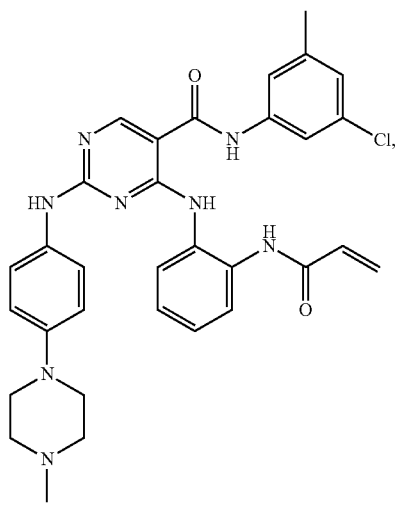
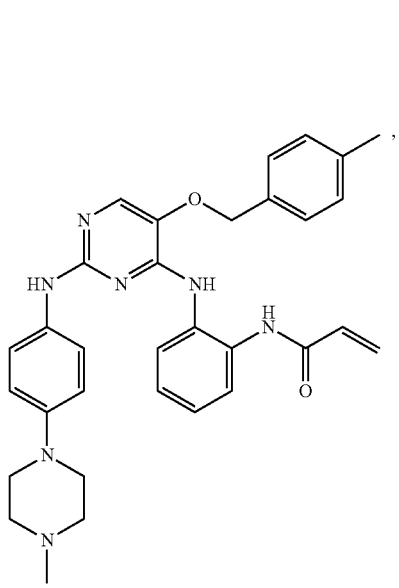

129
-continued
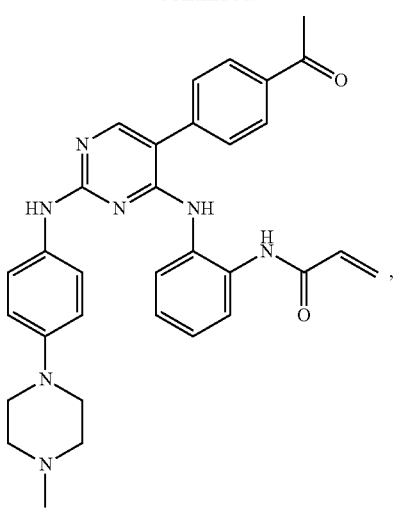
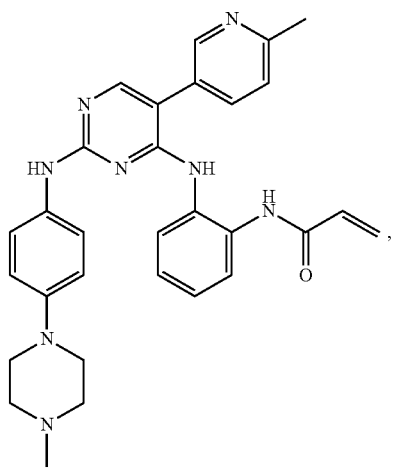
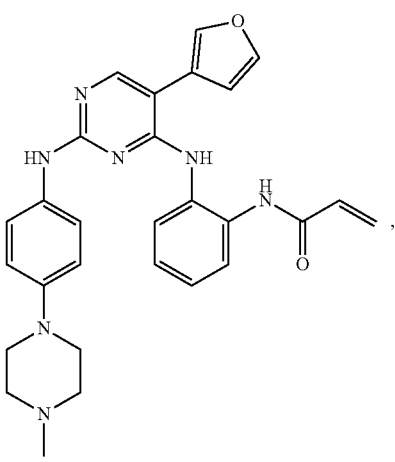
130
-continued
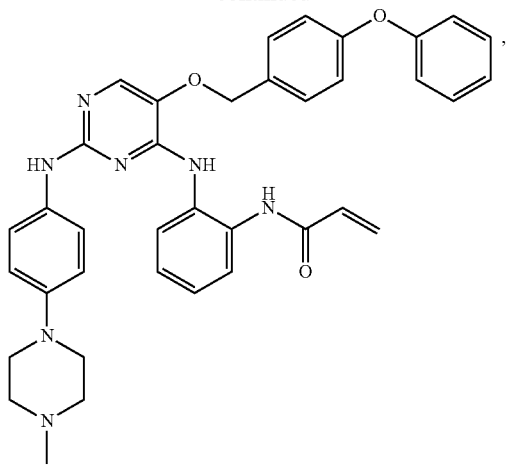
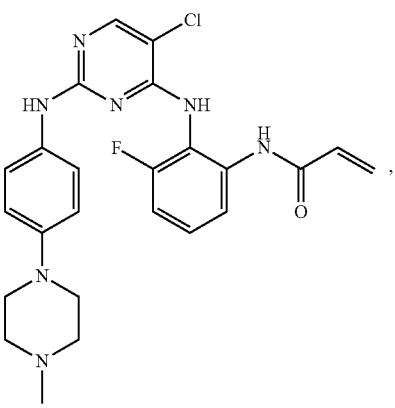
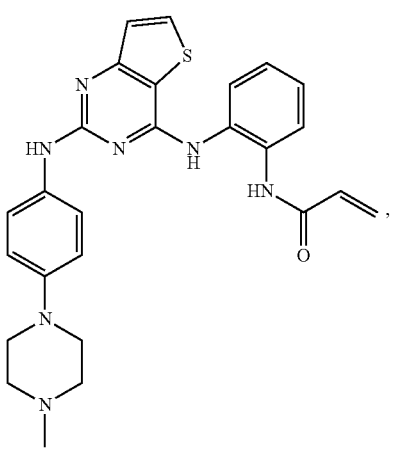

131
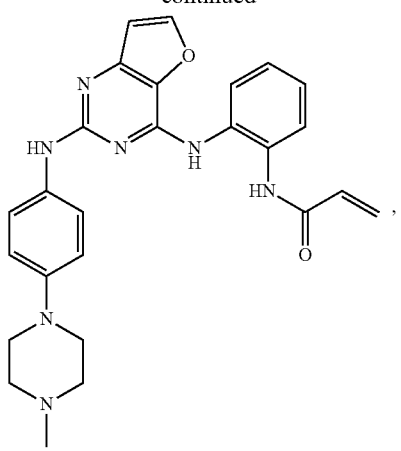
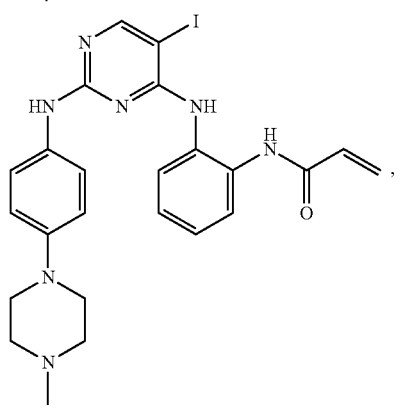
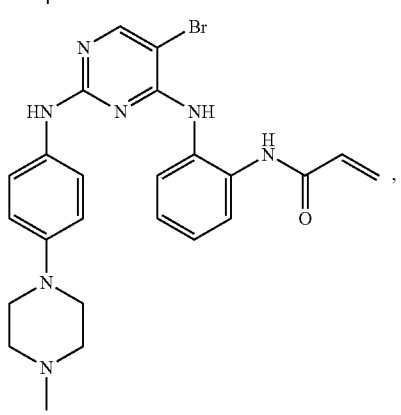
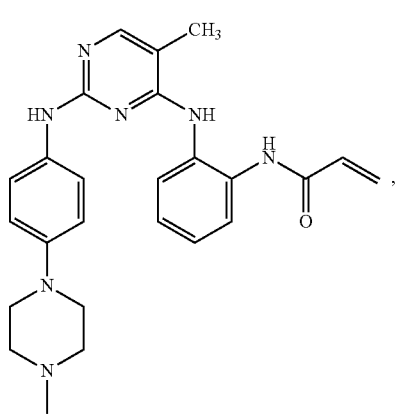
132
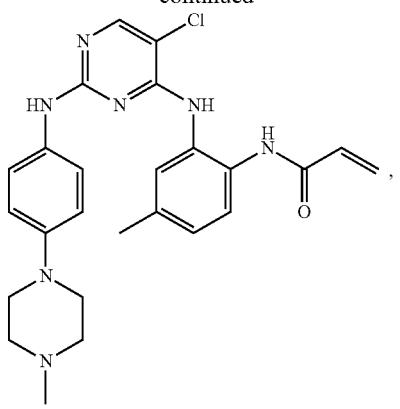
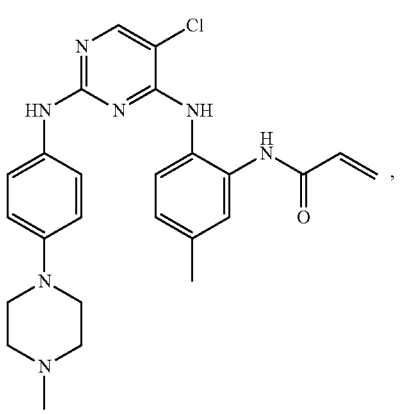
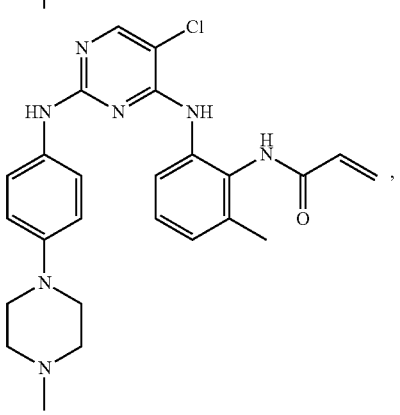
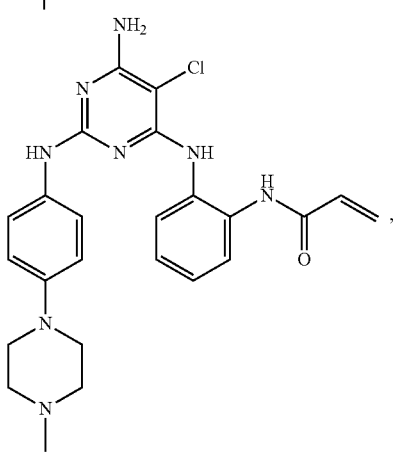

133
-continued
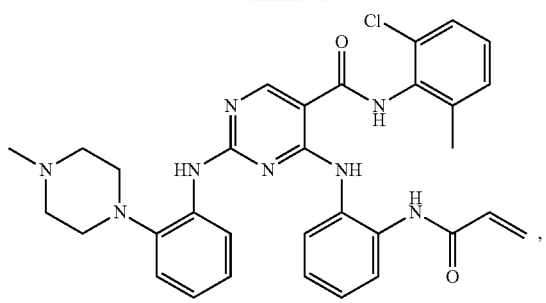
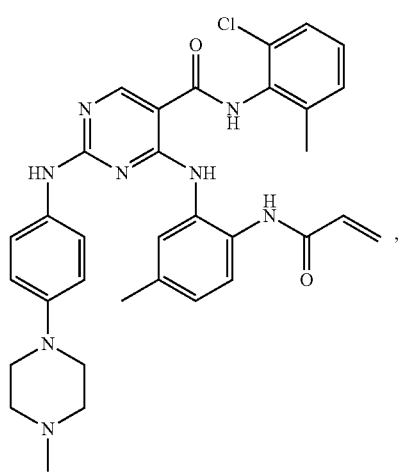
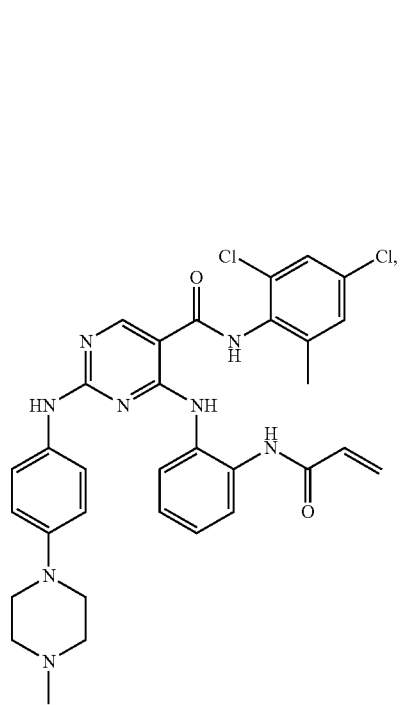
134
-continued
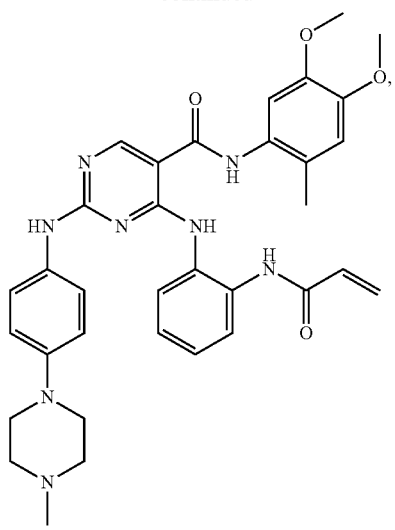
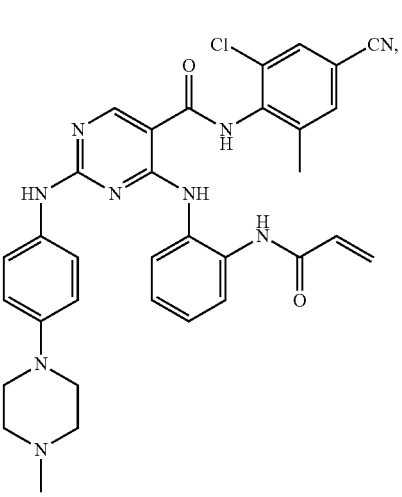
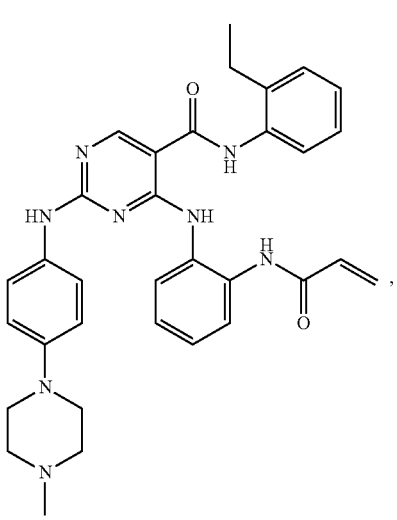

135
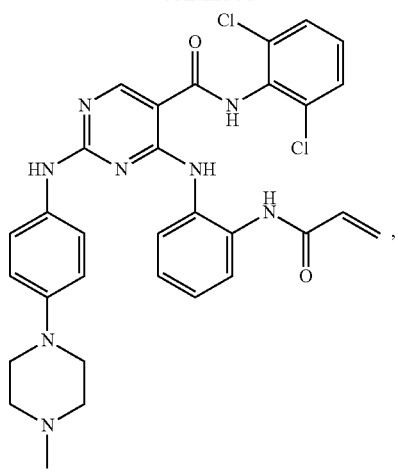
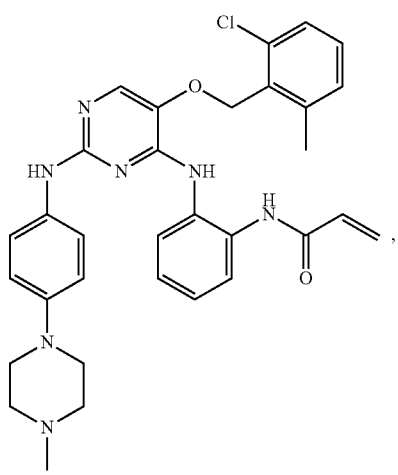
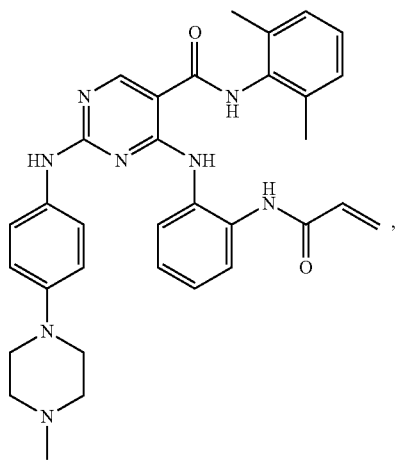
136
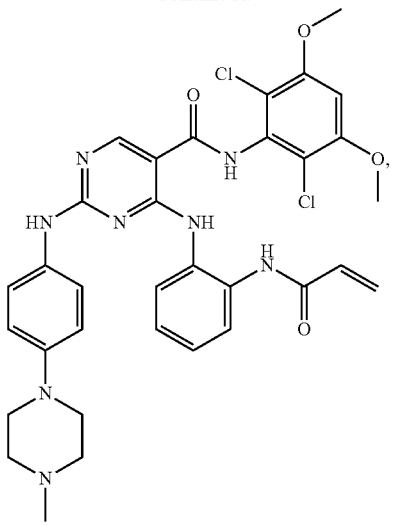
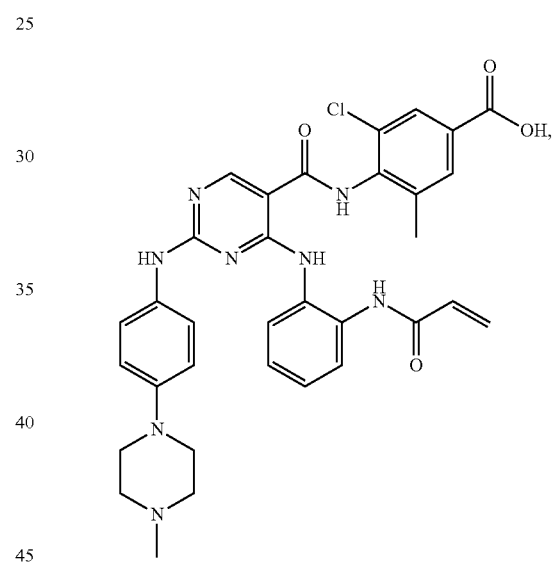
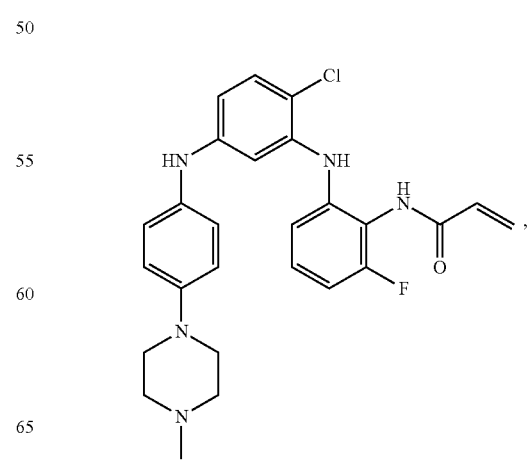

137
-continued
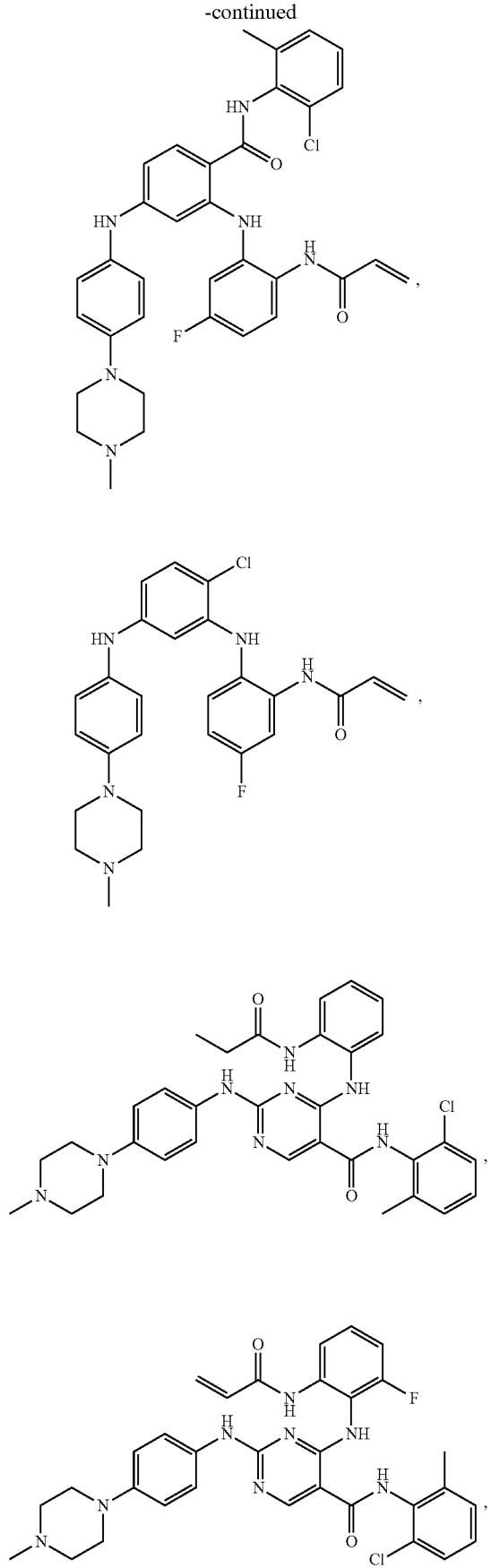
138
-continued
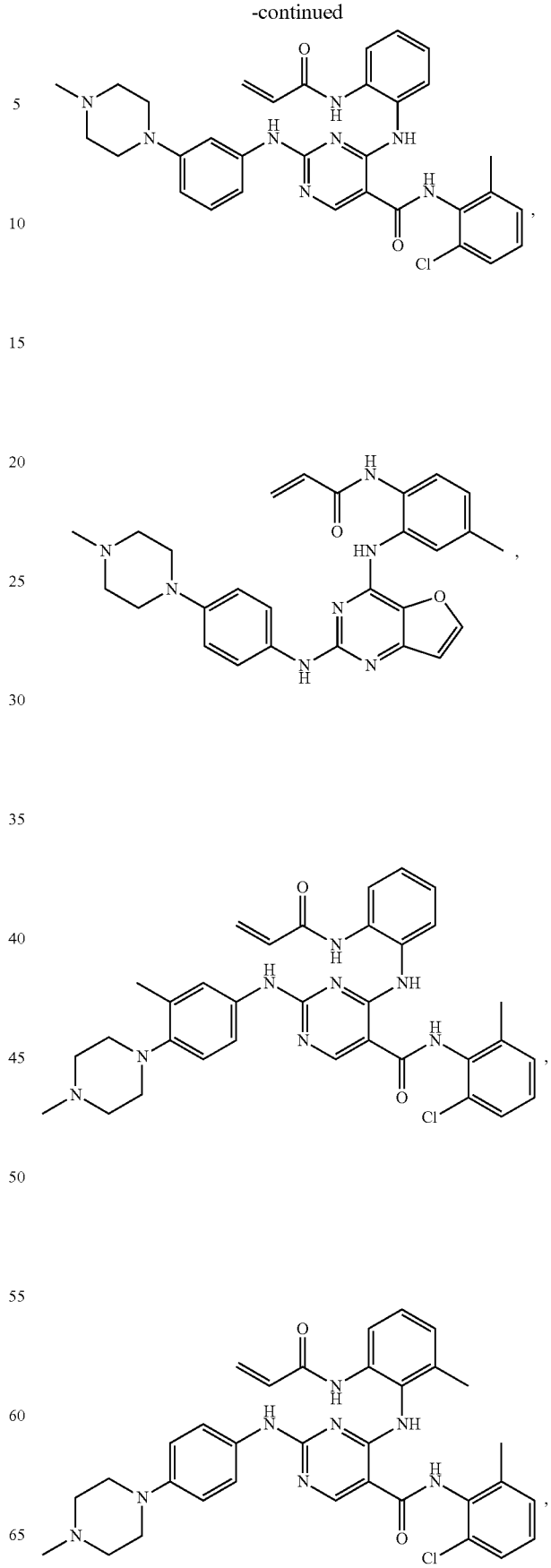

-continued
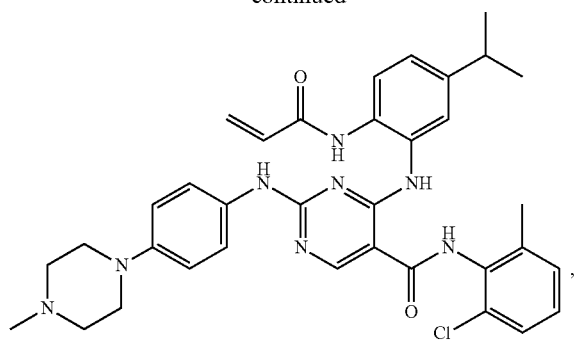
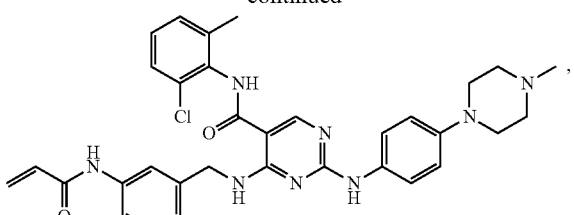
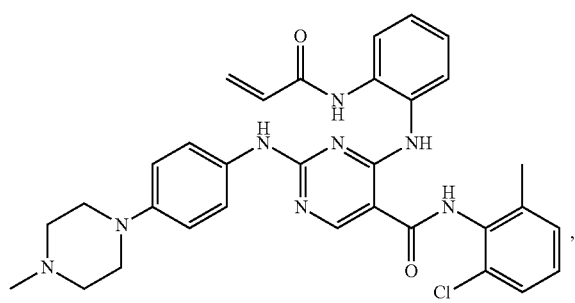
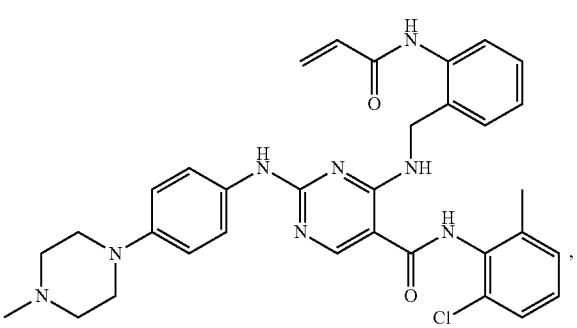
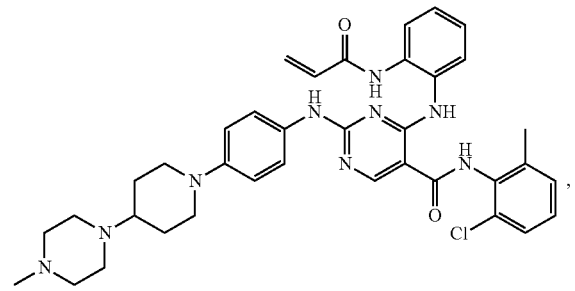
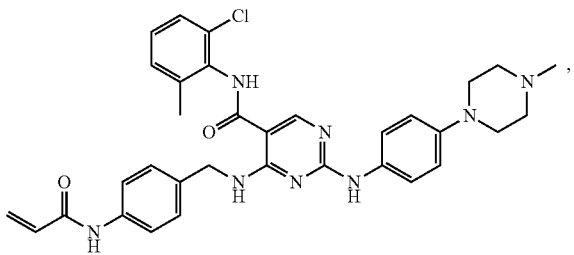
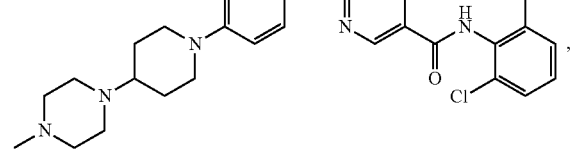
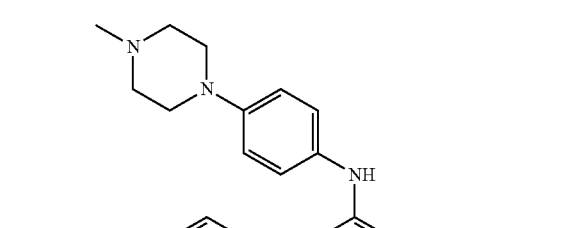
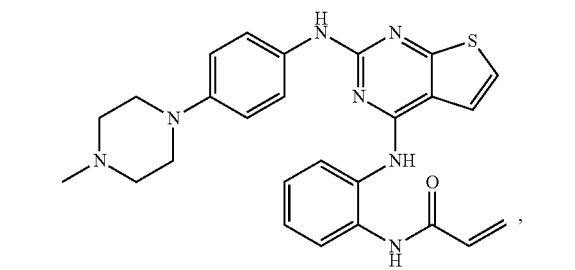
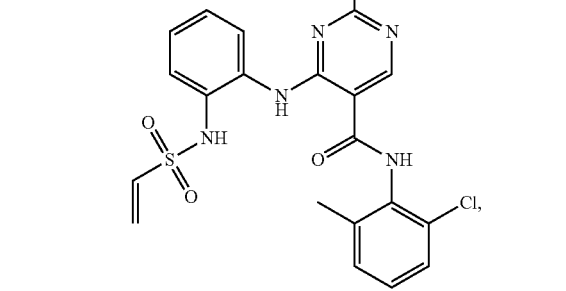

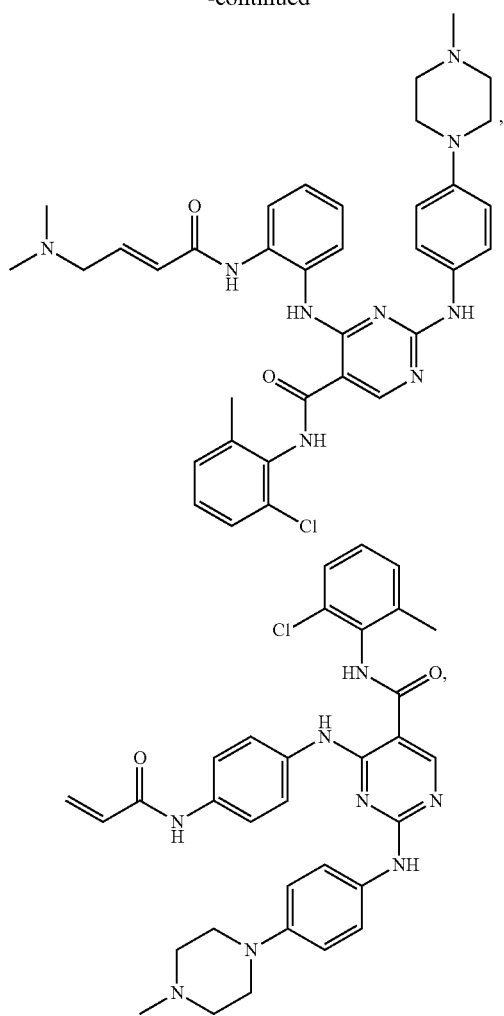
,

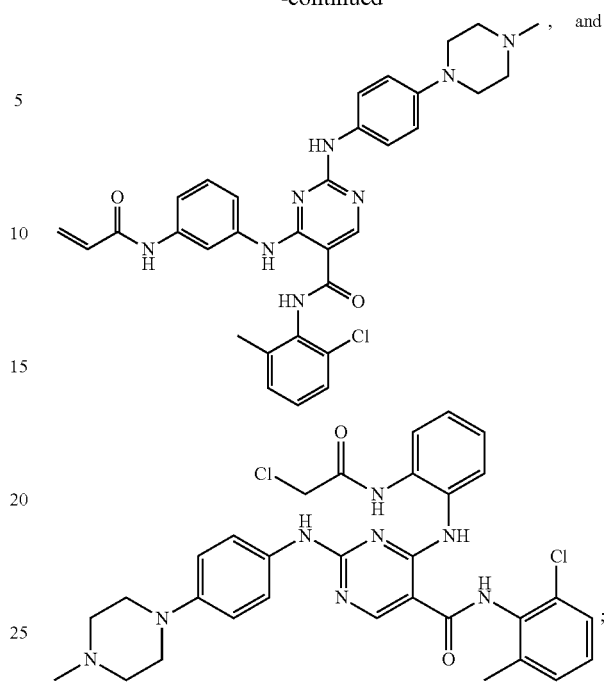

or a pharmaceutically acceptable salt thereof.

23. A pharmaceutical composition comprising the compound of claim 1 and a pharmaceutically acceptable excipient.

24. A method of treating melanoma, non-small cell lung cancer, colorectal cancer, pancreatic cancer, or breast cancer in a subject in need thereof comprising administering to the subject an effective amount of a compound of claim 1.

* * * * *